US006909001B2

(12) United States Patent
Anderson et al.

(10) Patent No.: US 6,909,001 B2
(45) Date of Patent: Jun. 21, 2005

(54) METHOD OF MAKING TRICYCLIC AMINOCYANOPYRIDINE COMPOUNDS

(75) Inventors: David R. Anderson, Lake St. Louis, MO (US); Shridhar G. Hegde, Ballwin, MO (US); Stephen A. Kolodziej, Ballwin, MO (US); William F. Vernier, Oceanside, CA (US); Emily J. Reinhard, Ridgewood, NJ (US)

(73) Assignee: Pharmacia Corporation, Chesterfield, MO (US)

( * ) Notice: Subject to any disclaimer, the term of this patent is extended or adjusted under 35 U.S.C. 154(b) by 0 days.

(21) Appl. No.: 10/729,794

(22) Filed: Dec. 5, 2003

(65) Prior Publication Data

US 2004/0127714 A1 Jul. 1, 2004

Related U.S. Application Data

(60) Provisional application No. 60/432,783, filed on Dec. 12, 2002.

(51) Int. Cl.$^7$ .................. C07D 491/052; C07D 495/04; C07D 471/04
(52) U.S. Cl. ............................. 546/89; 546/80; 546/81; 546/92; 546/66; 544/126
(58) Field of Search ............................. 546/89, 65, 80, 546/81, 92; 544/126

(56) References Cited

U.S. PATENT DOCUMENTS

| | | | |
|---|---|---|---|
| 4,299,963 A | 11/1981 | Nohara et al. | |
| 5,192,768 A | 3/1993 | Suzuki et al. | 514/293 |
| 5,561,100 A | 10/1996 | Hagen et al. | |
| 6,046,208 A | 4/2000 | Adams et al. | 514/274 |
| 6,218,136 B1 | 4/2001 | Kumar et al. | 435/15 |
| 6,268,163 B1 | 7/2001 | Kongsbak et al. | 435/15 |
| 6,335,340 B1 | 1/2002 | Gallagher et al. | 514/252.05 |
| 6,432,962 B2 | 8/2002 | Horneman | 514/255.06 |
| 2003/0139435 A1 | 7/2003 | Ahmed et al. | |

FOREIGN PATENT DOCUMENTS

| | | | | |
|---|---|---|---|---|
| WO | WO 99/51735 | 10/1999 | ........... | C12N/15/11 |
| WO | WO 01/29037 A2 | 4/2001 | ......... | C07D/471/00 |
| WO | WO 01/47892 A1 | 7/2001 | ......... | C07D/215/54 |

OTHER PUBLICATIONS

O'Callaghan et al.: Reactions of 2–oxo–2H–1–benzopyran–3–carbonitrile. J. Chem. Res., synopses, vol. 9, pp. 312–313, 1997.*
Article from Bioorganic & Medicinal Chemistry Letters, vol. 5, No. 23, pp. 2783–2788, 1995 by C. W. Smith et al., entitled The Anti–Rheumatic Potential o f a Series of 2,4–Di–substituted–4H–Naphtho[1,2–b] Pyran–3–Carbonitriles.
Abstract No. 132:260099 entitled "Anti–Inflammatory Substances" by N. Hirasawa et al., *Tanpakushitsu Kakusan Koso*, 45(6): 1199–1203 (2000).

Abstract from J. Biol. Chem., Jan. 2003, vol. 278(3), pp. 1450–1456 by J.R. Burke et al. entitled BMS–34551 is a highly selective inhibitor of I kappa B kinase that binds at an allosteric site of the enzyme and blocks NF–kappa B–dependent transcription in mice.
Abstract from The Journal of Biochemical Chemistry, Oct. 2002, vol. 367(Pt2): pp. 525–532 by A. Knebel, et al. entitled Stress–induced regulation of eukaryotic elongation factor 2 kinase by SB 203580 –sensitive and—insensitive pathways.
Abstract from Biochim Biophys. Acts., Jul. 2002, vol. 1598(1–2): pp. 88–97 by J.F. Schindler et al. entitled Examination of the kinetic mechanism of mitogen–activated protein kinase activated protein kinase–2.
Article from FEBS Letters 392 (1996), pp. 209–214 by A. Clifton et al. entitled A comparison of the substrate specificity of MAPKAP kinase–2 and MAPKAP kinase–3 and their activation by cytokines and cellular stress.
Article from FEBS Letters 364 (1995), pp. 229–233 by A. Cuenda et al. entitled SB 203580 is a specific inhibitor of a MAP kinase homologue which is stimulated by cellular stresses and interleukin–1.
Article from The Journal of Immunology, Jul. 2000, 165: pp. 3951–3958, by A. K. De et al. entitled Exaggerated Human Monocyte IL–10 Concomitant to Minimal TNA–α Induction by Heat Shock Protein 27 (Hsp27) Suggests Hsp27 is Primarily an Antiinflammatory Stimulus.
Article from The American Society for Biochemistry and Molecular Biology, Inc., Nov. 1995, vol. 270(45), pp. 27213–27221 by K. Engel et al. entitled Constitutive Activation of Mitogen–activated Protein Kinase–activated Protein Kinase 2 by Mutation of Phosphorylation Sites and an A–helix Motif(*).
Article from The Journal of Biological Chemistry, Feb. 1997, vol. 272(6): pp. 3296–3301 by I.N. Foltz et al. entitled Hemopoietic Growth Factors with the Exception of Interleukin–4 Activate the p38 Mitogen–activated Protein Kinase Pathway.
Article from The Journal of Biological Chemistry, Feb. 1997, vol. 272(6): pp. 3296–3301 by I.N. Foltz et al. entitled Hemopoietic Growth Factors with the Exception of Interleukin–4 Activate the p38 Mitogen–activated Protein Kinase Pathway.
Article from The Journal of Immunology, Jul. 2001, 167: pp. 3953–3961 by M. O. Hannigan et al. entitled Abnormal Migration Phenotype of Mitogen–Activated Protein Kinase–Activated Protein Kinase 2$^{-/-}$ Neutrophils in Zigmond Chambers Containing Formyl–Methionyl–Leucyl–Phenylalanine Gradients.

(Continued)

*Primary Examiner*—Charanjit S. Aulakh
(74) *Attorney, Agent, or Firm*—Patricia G. Keller

(57) ABSTRACT

A method of making aminocyanopyridine compounds which are capable of inhibiting mitogen activated protein kinase-activated protein kinase-2 is described.

17 Claims, No Drawings

OTHER PUBLICATIONS

Article from The Journal of Biological Chemistry, May 1999, vol. 274(20): pp. 14434–14443 by O. Heidenreich et al. entitled MAPKAP Kinase 2 Phosphorylates Serum Response Factor in Vitro and in Vivo*.

Article from The Journal of Biological Chemistry, Jul. 2001, vol. 276(45): pp. 41856–41861 by R. Janknecht entitled Cell Type–specific inhibition of the ETS Transcription Factor ER81 by Mitogen–activated Protein Kinase–activated Protein Kinase 2*.

Article from Biochemical Society Transactions, 2002, vol. 30(6): pp. 959–963 by A. Kotlyarov et al. entitled Is MK2 (mitogen–activated protein kinase–activated protein kinase 2) the key for understanding post–transcriptional regulation of gene expression?.

Article from Nature Cell Biology Jun. 1999, vol. 1: pp. 94–97 by A. Kotlyarov et al. entitled MAPKAP kinase 2 is essential for LPS–induced TNF–α biosynthesis.

Article from The Journal of Immunology, Mar. 2002, vol. 168(9): pp. 4667–4673 by M. D. Lehner et al. entitled Mitogen–Activated Protein Kinase–Activated Protein Kinase 2–Deficient Mice Show Increased Suseptibility to *Listeria monocytogenes* infection.

Article from Molecular Endocrinology, 2001, vol. 15(5): pp. 716–733 by E. T. Maizels et al. entitled Developmental Regulation of Mitogen–Activated Protein Kinase–Activated Kinase–2 and –3 (MAPKAPK–2/3) in Vivo during Corpus Luteum Formation in the Rat.

Article from The Journal of Biochemical Chemistry, Sep. 1998, vol. 273(38): pp. 24832–24838 by K. Miyazawa et al entitled Regulation of Interleukin–1β–induced Interleukia–6 Gene Expression in Human Fibroblast–like Synoviocytes by p38 Mitogen–activated Protein Kinase.

Article from Circulation Research, Feb. 2000: pp. 144–151 by N. Nakano et al. entitled ischemic Preconditioning Activates MAPKAPK2 in the Isolated Rabbit Heart.

Article from The Journal of Neuroscience, Mar. 1998, vol. 18(5): pp. 1633–1641 by N. Bhat et al. entitled Extracellular Signal–Regulated Kinase and p38 Subgroups of Mitogen–Activated Protein Kinases Regulate Inducible Nitric Oxide Synthase and Tumor Necrosis Factor–α Gene Expression in Endotoxin–Stimulated Primary Glial Cultures.

Article from The Journal of Biological Chemistry, Feb. 2002, vol. 277(5): pp. 3065–3068 by A. Neininger et al. entitled MK2 Targets AU–rich Elements and Regulates Biosynthesis of Tumor Necrosis Factor and Interleukin–6 Independently at Different Post–transcriptional Levels*.

Article from The Journal of Biological Chemistry, Apr. 2000, vol. 275(15): pp. 11284–11290 by E. Paine et al. entitled Arachidonic Acid Activates Mitogen–activated Protein (MAP) Kinase–activated Protein Kinase 2 and Mediates Adhesion of a Human Breast Carcinoma Cell Line to Collagen Type IV through a p38 MAP Kinase–dependent Pathway.

Article from Blood, Jan. 1999, vol. 93(1): pp. 217–225 by M. P. Scheid et al. entitled Ceramide and Cyclic Adenosine Monophosphate (cAMP) Induce cAMP Response Element Binding Protein Phosphorylation via Distinct Signaling Pathways While Having Opposite Effects on Myeloid Cell Survival.

Article from Proc. Natl. Acad. Sci, May 2000, vol. 97(10): pp. 5261–5266 by O. Werz et al. entitled 5–Lipoxygenase is phosphorylated by p38 kinase–dependent MAPKAP kinases.

Article from Kidney International, Mar. 2001, vol. 60: pp. 858–871 by W. A. Wilmer et al. entitled Chronic exposure of human mesangial cells to high glucose environments activates the p38 MAPK pathway.

Article: Conor N. O'Callaghan,, et al., University Chemical Laboratory, Trinity College, Dublin 2, Ireland, entitled: Synthetic Reactions of 2–(2–Amino–3–cyano–4H–[1] benzopyran–4–yl)propane–1.3–dinitrile with Reactive Methylene Compounds.

PCT International Search Report, International PCT Application No. PCT/US03/38980.

PCT International Search Report, International PCT Application No. PCT/US03/38999.

PCT International Search Report, International PCT Application No. PCT/US03/39166.

* cited by examiner

METHOD OF MAKING TRICYCLIC AMINOCYANOPYRIDINE COMPOUNDS

CROSS REFERENCE TO RELATED PATENTS AND PATENT APPLICATIONS

This application claims the benefit of U.S. Provisional Patent Application Ser. No. 60/432,783, filed Dec. 12, 2002, which is incorporated by reference herein in its entirety. This application is related to commonly assigned and copending applications having the titles "Method of using aminocyanopyridine compounds as mitogen activated protein kinase-activated protein kinase-2 inhibitors" (and having Provisional Application Ser. No. 60/432,807), and "Tricyclic aminocyanopyridine inhibitors of mitogen activated protein kinase-activated protein kinase-2" (and having Provisional Application Ser. No. 60/432,844), each of which was filed on the same date as the present application.

BACKGROUND OF THE INVENTION (1) Field of the Invention

The present invention relates to aminocyanopyridine compounds, and in particular, to tricyclic aminocyanopyridine compounds which inhibit mitogen-activated protein kinase-activated protein kinase-2 (MAPKAP-kinase 2, or MK-2), and compositions containing those aminocyanopyridine compounds.

(2) Description of the Related Art

Mitogen-activated protein kinases (MAPKs) are members of conserved signal transduction pathways that activate transcription factors, translation factors and other target molecules in response to a variety of extracellular signals. MAPKs are activated by phosphorylation at a dual phosphorylation motif with the sequence Thr-X-Tyr by mitogen-activated protein kinase kinases (MAPKKs). In higher eukaryotes, the physiological role of MAPK signaling has been correlated with cellular events such as proliferation, oncogenesis, development and differentiation. Accordingly, the ability to regulate signal transduction via these pathways could lead to the development of treatments and preventive therapies for human diseases associated with MAPK signaling, such as inflammatory diseases, autoimmune diseases and cancer.

In mammalian cells, three parallel MAPK pathways have been described. The best characterized pathway leads to the activation of the extracellular-signal-regulated kinase (ERK). Less well understood are the signal transduction pathways leading to the activation of the cJun N-terminal kinase (JNK) and the p38 MAPK. See, e.g., Davis, *Trends Biochem. Sci.* 19:470–473 (1994); Cano, et al., *Trends Biochem. Sci.* 20:117–122(1995).

The p38 MAPK pathway is potentially activated by a wide variety of stresses and cellular insults. These stresses and cellular insults include heat shock, UV irradiation, inflammatory cytokines (such as TNF and IL-1), tunicamycin, chemotherapeutic drugs (i.e., cisplatinum), anisomycin, sorbitol/hyperosmolarity, gamma irradiation, sodium arsenite, and ischaemia. See, Ono, K., et al, *Cellular Signalling* 12, 1–13 (2000). Activation of the p38 pathway is involved in (1) production of proinflammatory cytokines, such as TNF-α; (2) induction of enzymes, such as Cox-2; (3) expression of an intracellular enzyme, such as iNOS, which plays an important role in the regulation of oxidation; (4) induction of adherent proteins, such as VCAM-1 and many other inflammatory-related molecules. Furthermore, the p38 pathway functions as a regulator in the proliferation and differentiation of cells of the immune system. See, Ono, K., et al., Id. at 7.

The p38 kinase is an upstream kinase of mitogen-activated protein kinase-activated protein kinase-2 (MAPKAP kinase-2 or MK-2). (See, Freshney, N. W., et al., *J. Cell,* 78:1039–1049 (1994)). MK-2 is a protein that appears to be predominantly regulated by p38 in cells. Indeed, MK-2 was the first substrate of p38α to be identified. For example, in vitro phosphorylation of MK-2 by p38α activates MK-2. The substrates that MK-2 acts upon, in turn, include heat shock protein 27, lymphocyte-specific protein 1 (LAP1), cAMP response element-binding protein (CREB), ATF1, serum response factor (SRF), and tyrosine hydroxylase. The substrate of MK-2 that has been best characterized is small heat shock protein 27 (hsp27).

The role of the p38 pathway in inflammatory-related diseases has been studied in several animal models. The pyridinyl imidazole compound SB203580 has been shown to be a specific inhibitor of p38 in vivo, and also has been shown to inhibit activation of MK-2, (See, Rouse, J., et al, *Cell,* 78:1027–1037 (1994); Cuenda, A., et al, *Biochem. J.,* 333:11–15 (1998)), as well as a MAP kinase homologue termed reactivating kinase (RK). (See, Cuenda, A., et al., *FEBS Lett.,* 364(2):229-233 (1995)). Inhibition of p38 by SB203580 can reduce mortality in a murine model of endotoxin-induced shock and inhibit the development of mouse collagen-induced arthritis and rat adjuvant arthritis. See, e.g., Badger, A. M., et al., *J. Pharmacol Exp. Ther.,* 279:1453–1461 (1996). Another p38 inhibitor that has been utilized in an animal model that is believed to be more potent than SB203580 in its inhibitory effect on p38 is SB 220025. A recent animal study has demonstrated that SB 220025 caused a significant dose-dependent decrease in vascular density of granulomas in laboratory rats. (See Jackson, J. R., et al, *J. Pharmacol. Exp. Ther.,* 284:687–692 (1998)). The results of these animal studies indicated that p38, or the components of the p38 pathway, can be useful therapeutic targets for the prevention or treatment of inflammatory disease.

Due to its integral role in the p38 signaling pathway, MK-2 has been used as a monitor for measuring the level of activation in the pathway. Because of its downstream location in the pathway, relative to p38, MK-2 has been measured as a more convenient, albeit indirect, method of assessing p38 activation. However, so far, research efforts exploring therapeutic strategies associated with the modulation of this pathway have focused mainly on the inhibition of p38 kinase.

Several compounds that inhibit the activity of p38 kinase have been described in U.S. Pat. Nos. 6,046,208, 6,251,914, and 6,335,340. These compounds have been suggested to be useful for the treatment of CSBP/RK/p38 kinase mediated disease. Commercial efforts to apply p38 inhibitors have centered around two p38 inhibitors, the pyridinylimidazole inhibitor SKF 86002, and the 2,4,5 triaryl imidazole inhibitor SB203580. See, Lee, J. C., et al, *Immunopharmacology* 47, 185–192 (2000). Compounds possessing a similar structure have also been investigated as potential p38 inhibitors. Indeed, p38 MSP kinase's role in various disease states has been elucidated through the use of inhibitors.

Kotlyarov, A. et al, in *Nat. Cell Biol.,* 1(2):94–97 (1999) introduced a targeted mutation into a mouse MK-2 gene, resulting in MK-2-deficient mice. It was shown that mice lacking MK-2 possessed increased stress resistance and survived LPS-induced endotoxic shock better than MK-2$^+$ mice. The authors concluded that MK-2 was an essential component in the inflammatory response that regulates biosynthesis of TNFα at a post-transcriptional level. More recently, Lehner, M. D., et al, in *J. Immunol.,* 168(9)

:4667–4673 (2002), reported that MK-2-deficient mice showed increased susceptibility to *Listeria monocytogenes* infection, and concluded that MK-2 had an essential role in host defense against intracellular bacteria, probably via regulation of TNF and IFN-gamma production required for activation of antibacterial effector mechanisms.

The location of MK-2 in the p38 signaling pathway at a point that is downstream of p38 offers the potential that MK-2 could act as a focal point for modulating the pathway without affecting as many substrates as would the regulation of an enzyme further upstream in the signaling cascade— such as p38 MAP kinase.

Accordingly, it would be useful to provide compounds that could serve to modulate the activity of MK-2—in particular, to act as inhibitors of MK-2 activity. It would be useful to provide a method of making such aminocyanopyridine compounds which was simple and straightforward. It would be even more useful if such method could be formulated as a "single pot" method, wherein all reactions that are required for the production of a tricyclic aminocyanopyridine MK-2 inhibitor can be carried out in a single vessel without removal or transfer of the contents to a separate vessel at some point during the production process.

SUMMARY OF THE INVENTION

Briefly, therefore the present invention is directed to a novel method of making a tricyclic aminocyanopyridine MK-2 inhibiting compound, the method comprising:

reacting a substituted benzaldehyde having the structure:

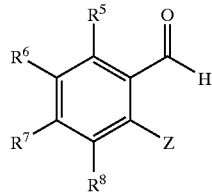

with a tricarbonitrile having the structure:

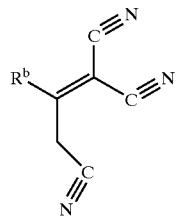

to form an aminocyanopyridine compound having the structure:

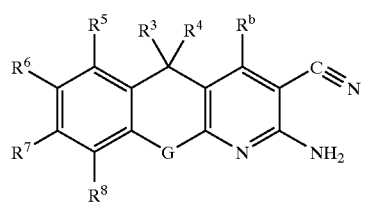

wherein:

Z is selected from the group consisting of —OH, —SH, and —NR$^a$Y;

R$_a$ is selected from the group consisting of alkyl, aryl, and heteroaryl;

Y is a protecting group for nitrogen that is selected from the group consisting of benzyl, allyl, alkyl carbamates and benzyl carbamate;

G is selected from the group consisting of oxygen, sulfur, and nitrogen;

when G is oxygen, it has no substituent groups;

when G is sulfur, it is either unsubstituted, or is substituted with one or two oxo groups;

when G is nitrogen, it is substituted with $C_1$–$C_4$ alkyl;

R$^b$ is selected from the group consisting of furyl and —NH—R$^2$;

R$^2$ is selected from the group consisting of hydrogen, alkyl, alkenyl, alkynyl, alkoxy, hydroxyalkyl, alkylaryl, arylalkyl, alkoxyaryl, aminoalkyl, alkylaminoalkyl, arylaminoalkyl, alkoxyalkyl, alkylcarboxy, and carboxyalkyl;

R$^3$ and R$^4$ are each independently selected from the group consisting of hydrogen, dicyanoalkyl, and substituted or unsubstituted heterocyclyl and cyclyl, where substituents, if any, comprise halo moieties; and R$^5$, R$^6$, R$^7$ and R$^8$ are each independently selected from the group consisting of hydrogen, hydroxy, alkoxy, halo, alkyl, alkenyl, alkylyl, arylalkyl, alkylaryl, amino, alkylamino, arylamino, alkylaminoalkyl, carboxy, aminoalkoxy, alkylcarboxyalkyl, alkylamino, aminoalkyl, nitro, aryl, arylamino, alkenoxy, hydroxyalkoxy, alkoxyalkoxy, heterocyclylalkyl, heterocyclylalkoxy, carboxyalkoxy, alkylaminoalkoxy, alkylcarboxyalkoxy, pyrrolidylethoxy, hydroxyalkoxy, and alkylcarboxy, where R$^6$ and R$^7$ are such that they optionally join to form a six membered heterocyclic ring.

The present invention is also directed to a novel method of making a tricyclic aminocyanopyridine MK-2 inhibiting compound, the method comprising:

reacting a substituted benzaldehyde having the structure:

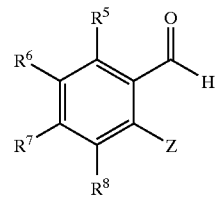

with a tricarbonitrile having the structure:

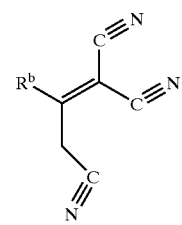

to form an aminocyanopyridine compound having the structure:

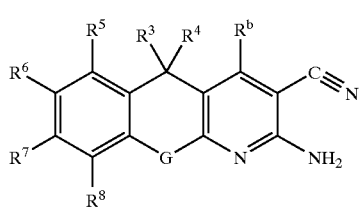

wherein:
- Z is selected from the group consisting of —OH, —SH, and —NR$^a$Y;
- R$_a$ is selected from the group consisting of alkyl, aryl, and heteroaryl;
- Y is a protecting group for nitrogen that is selected from the group consisting of benzyl, allyl, alkyl carbamates and benzyl carbamate;
- G is selected from the group consisting of oxygen, sulfur, and nitrogen;
- when G is oxygen, it has no substituent groups;
- when G is sulfur, it is either unsubstituted, or is substituted with one or two oxo groups;
- when G is nitrogen, it is substituted with $C_1$–$C_4$ alkyl;
- R$^b$ is selected from the group consisting of furyl and —NH—R$^2$;
- R$^2$ is selected from the group consisting of hydrogen, alkyl, alkenyl, alkynyl, alkoxy, hydroxyalkyl, alkylaryl, arylalkyl, alkoxyaryl, aminoalkyl, alkylaminoalkyl, arylaminoalkyl, alkoxyalkyl, alkylcarboxy, and carboxyalkyl;
- R$^3$ and R$^4$ are each independently selected from the group consisting of hydrogen, dicyanoalkyl, and substituted or unsubstituted heterocyclyl and cyclyl, where substituents, if any, comprise halo moieties; and
- R$^5$, R$^6$, R$^7$ and R$^8$ are each independently selected from the group consisting of: hydrogen, hydroxy, amino, halo, nitro,
  - branched or unbranched $C_1$–$C_6$ alkyl, $C_2$–$C_6$ alkenyl, $C_2$–$C_6$ alkynyl, $C_1$–$C_6$ alkoxy, hydroxy $C_1$–$C_6$ alkyl, hydroxy $C_1$–$C_6$ alkoxy, $C_1$–$C_6$ alkoxy $C_1$–$C_6$ alkoxy, $C_1$–$C_6$ alkoxy $C_1$–$C_6$ alkyl, $C_2$–$C_6$ alkenoxy,
  - branched or unbranched amino $C_1$–$C_6$ alkyl, diamino $C_2$–$C_6$ alkyl, $C_1$–$C_6$ alkylamino $C_1$–$C_6$ alkyl, $C_1$–$C_6$ alkylamino, di-($C_1$–$C_6$ alkyl)amino, $C_1$–$C_4$ alkoxyarylamino, $C_1$–$C_4$ alkoxyalkylamino, amino $C_1$–$C_6$ alkoxy, di-($C_1$–$C_4$ alkylamino, $C_2$–$C_6$ alkoxy, di-($C_1$–$C_6$ alkyl)amino $C_1$–$C_6$ alkyl, $C_1$–$C_6$ alkylamino $C_1$–$C_6$ alkoxy, halo $C_1$–$C_6$alkoxy, dihalo $C_1$–$C_6$alkoxy, trihalo $C_1$–$C_6$ alkoxy, cyano $C_1$–$C_6$ alkyl, dicyano $C_1$–$C_6$ alkyl, cyano $C_1$–$C_6$ alkoxy, dicyano $C_1$–$C_6$ alkoxy, carbamyl $C_1$–$C_4$ alkoxy, heterocyclyl $C_1$–$C_4$ alkoxy, heteroaryl $C_1$–$C_4$ alkoxy, sulfo, sulfamyl, $C_1$–$C_4$ alkylaminosulfonyl, hydroxy $C_1$–$C_4$ alkylaminosulfonyl, di-($C_1$–$C_4$ alkyl)aminosulfonyl, $C_1$–$C_4$ alkylthio, $C_1$–$C_4$ alkylsulfonyl, $C_1$–$C_4$ alkylsulfinyl,
  - aryl, aryl $C_1$–$C_6$ alkyl, heterocyclyl $C_1$–$C_6$ alkyl, heteroaryl $C_1$–$C_6$ alkyl, heterocyclyl $C_1$–$C_6$ alkoxy, heteroaryl $C_1$–$C_6$ alkoxy, aryl $C_1$–$C_6$ alkoxy, where the aryl ring can be substituted or unsubstituted, and, if substituted, the substituent group is selected from one or more of the group consisting of $C_1$–$C_6$ alkyl, halo, amino, and $C_1$–$C_6$ alkoxy,
  - substituted or unsubstituted $C_3$–$C_6$ cyclyl, $C_3$–$C_6$ heterocyclyl, and, if substituted, the substituent group is selected from one or more of the group consisting of $C_1$–$C_6$ alkyl, $C_1$–$C_6$ alkoxy, halo, amino, and where the $C_3$–$C_6$ heterocyclyl ring contains O, S, or N,
  - branched or unbranched $C_1$–$C_6$ alkoxycarbonyl $C_1$–$C_6$ alkoxy, and
  - carboxy, carboxy $C_1$–$C_6$ alkoxy, carboxy $C_1$–$C_6$ alkyl, hydroxy $C_1$–$C_4$ alkoxycarbonyl, $C_1$–$C_4$ alkoxycarbonyl.

Among the several advantages found to be achieved by the present invention, therefore, may be noted the provision of a method of making a tricyclic aminocyanopyridine MK-2 inhibiting compound which was simple and straightforward; and also the provision of such a method that is a "single pot" method, wherein all reactions that are required for the production of a tricyclic aminocyanopyridine MK-2 inhibitor can be carried out in a single vessel without removal or transfer of the contents to a separate vessel at some point during the production process.

DETAILED DESCRIPTION OF THE PREFERRED EMBODIMENTS

In accordance with the present invention, a method has been discovered to produce certain aminocyanopyridine compounds that can inhibit the activity of MAPKAP kinase-2. These compounds can exhibit their inhibitory effect at low concentrations—having in vitro MK-2 inhibition $IC_{50}$ values of under 1.0 $\mu$M, and with some having $IC_{50}$ values of under about 0.5 $\mu$M, and even as low as about 0.2 $\mu$M.

It has been discovered that these compounds can be produced by reacting a substituted benzaldehyde having the structure:

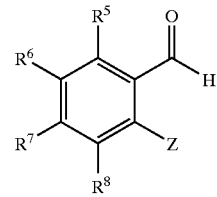

with a tricarbonitrile having the structure:

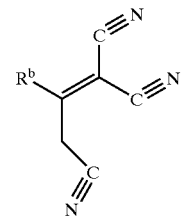

to form an aminocyanopyridine compound having the structure:

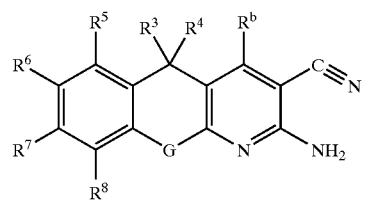

wherein:
- Z is selected from the group consisting of —OH, —SH, and —NR$^a$Y;

R_a is selected from the group consisting of alkyl, aryl, and heteroaryl;

Y is a protecting group for nitrogen that is selected from the group consisting of benzyl, allyl, alkyl carbamates and benzyl carbamate;

G is selected from the group consisting of oxygen, sulfur, and nitrogen;

when G is oxygen, it has no substituent groups;

when G is sulfur, it is either unsubstituted, or is substituted with one or two oxo groups;

when G is nitrogen, it is substituted with $C_1$–$C_4$ alkyl;

$R^b$ is selected from the group consisting of furyl and —NH—$R^2$;

$R^2$ is selected from the group consisting of hydrogen, alkyl, alkenyl, alkynyl, alkoxy, hydroxyalkyl, alkylaryl, arylalkyl, alkoxyaryl, aminoalkyl, alkylaminoalkyl, arylaminoalkyl, alkoxyalkyl, alkylcarboxy, and carboxyalkyl;

$R^3$ and $R^4$ are each independently selected from the group consisting of hydrogen, dicyanoalkyl, and substituted or unsubstituted heterocyclyl and cyclyl, where substituents, if any, comprise halo moieties; and $R^5$, $R^6$, $R^7$ and $R^8$ are each independently selected from the group consisting of:

hydrogen, hydroxy, amino, halo, nitro, branched or unbranched $C_1$–$C_6$ alkyl, $C_2$–$C_6$ alkenyl, $C_2$–$C_6$ alkynyl, $C_1$–$C_6$ alkoxy, hydroxy $C_1$–$C_6$ alkyl, hydroxy $C_1$–$C_6$ alkoxy, $C_1$–$C_6$ alkoxy $C_1$–$C_6$ alkoxy, $C_1$–$C_6$ alkoxy $C_1$–$C_6$ alkyl, $C_2$–$C_6$ alkenoxy, branched or unbranched amino $C_1$–$C_6$ alkyl, diamino $C_2$–$C_6$ alkyl, $C_1$–$C_6$ alkylamino $C_1$–$C_6$ alkyl, $C_1$–$C_6$alkylamino, di-($C_1$–$C_6$ alkyl)amino, $C_1$–$C_4$ alkoxyarylamino, $C_1$–$C_4$alkoxyalkylamino, amino $C_1$–$C_6$ alkoxy, di-($C_1$–$C_4$ alkylamino, $C_2$–$C_6$ alkoxy, di-($C_1$–$C_6$ alkyl)amino $C_1$–$C_6$ alkyl, $C_1$–$C_6$ alkylamino $C_1$–$C_6$ alkoxy, halo $C_1$–$C_6$ alkoxy, dihalo $C_1$–$C_6$ alkoxy, trihalo $C_1$–$C_6$alkoxy, cyano $C_1$–$C_6$ alkyl, dicyano $C_1$–$C_6$ alkyl, cyano $C_1$–$C_6$ alkoxy, dicyano $C_1$–$C_6$ alkoxy, carbamyl $C_1$–$C_4$ alkoxy, heterocyclyl $C_1$–$C_4$ alkoxy, heteroaryl $C_1$–$C_4$ alkoxy, sulfo, sulfamyl, $C_1$–$C_4$ alkylaminosulfonyl, hydroxy $C_1$–$C_4$ alkylaminosulfonyl, di-($C_1$–$C_4$ alkyl)aminosulfonyl, $C_1$–$C_4$ alkylthio, $C_1$–$C_4$ alkylsulfonyl, $C_1$–$C_4$ alkylsulfinyl, aryl, aryl $C_1$–$C_6$ alkyl, heterocyclyl $C_1$–$C_6$ alkyl, heteroaryl $C_1$–$C_6$ alkyl, heterocyclyl $C_1$–$C_6$ alkoxy, heteroaryl $C_1$–$C_6$ alkoxy, aryl $C_1$–$C_6$ alkoxy, where the aryl ring can be substituted or unsubstituted, and, if substituted, the substituent group is selected from one or more of the group consisting of $C_1$–$C_6$ alkyl, halo, amino, and $C_1$–$C_6$ alkoxy, substituted or unsubstituted $C_3$–$C_6$ cyclyl, $C_3$–$C_6$ heterocyclyl, and, if substituted, the substituent group is selected from one or more of the group consisting of $C_1$–$C_6$ alkyl, $C_1$–$C_6$ alkoxy, halo, amino, and where the $C_3$–$C_6$ heterocyclyl ring contains O, S, or N, branched or unbranched $C_1$–$C_6$ alkoxycarbonyl $C_1$–$C_6$ alkoxy, and carboxy, carboxy $C_1$–$C_6$ alkoxy, carboxy $C_1$–$C_6$ alkyl, hydroxy $C_1$–$C_4$ alkoxycarbonyl, $C_1$–$C_4$ alkoxycarbonyl.

Aminocyanopyridine compounds that can be produced by the present method include those aminocyanopyridine compounds having the structure shown in formula I:

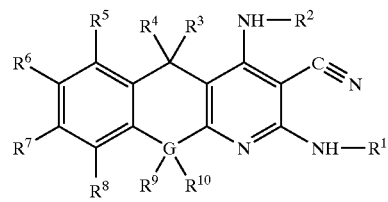

wherein:

$R^1$, $R^2$, $R^3$, $R^4$, $R^5$, $R^6$, $R^7$, and $R^8$ each is independently selected from the group consisting of hydrogen, hydroxy, amino, halo, nitro, branched or unbranched $C_1$–$C_6$ alkyl, $C_2$–$C_6$ alkenyl, $C_2$–$C_6$ alkynyl, $C_1$–$C_6$ alkoxy, hydroxy $C_1$–$C_6$ alkyl, hydroxy $C_1$–$C_6$ alkoxy, $C_1$–$C_6$ alkoxy $C_1$–$C_6$ alkoxy, $C_1$–$C_6$ alkoxy $C_1$–$C_6$ alkyl, $C_1$–$C_6$ alkenoxy, branched or unbranched amino $C_1$–$C_6$ alkyl, diamino $C_2$–$C_6$ alkyl, $C_1$–$C_6$ alkylamino $C_1$–$C_6$ alkyl, $C_1$–$C_6$ alkylamino, di-($C_1$–$C_6$ alkyl)amino, $C_1$–$C_4$ alkoxyarylamino, $C_1$–$C_4$alkoxyalkylamino, amino $C_1$–$C_6$ alkoxy, di-($C_1$–$C_4$ alkylamino, $C_2$–$C_6$ alkoxy, di-($C_1$–$C_6$ alkyl)amino $C_1$–$C_6$ alkyl, $C_1$–$C_6$ alkylamino $C_1$–$C_6$ alkoxy, halo $C_1$–$C_6$ alkoxy, dihalo $C_1$–$C_6$ alkoxy, trihalo $C_1$–$C_6$ alkoxy, cyano $C_1$–$C_6$ alkyl, dicyano $C_1$–$C_6$ alkyl, cyano $C_1$–$C_6$ alkoxy, dicyano $C_1$–$C_6$ alkoxy, carbamyl $C_1$–$C_4$ alkoxy, heterocyclyl $C_1$–$C_4$ alkoxy, heteroaryl $C_1$–$C_4$ alkoxy, sulfo, sulfamyl, $C_1$–$C_4$ alkylaminosulfonyl, hydroxy $C_1$–$C_4$ alkylaminosulfonyl, di-($C_1$–$C_4$ alkyl)aminosulfonyl, $C_1$–$C_4$ alkylthio, $C_1$–$C_4$ alkylsulfonyl, $C_1$–$C_4$ alkylsulfinyl, aryl, aryl $C_1$–$C_6$ alkyl, heterocyclyl $C_1$–$C_6$ alkyl, heteroaryl $C_1$–$C_6$ alkyl, heterocyclyl $C_1$–$C_6$ alkoxy, heteroaryl $C_1$–$C_6$ alkoxy, aryl $C_1$–$C_6$ alkoxy, where the aryl ring can be substituted or unsubstituted, and, if substituted, the substituent group is selected from one or more of the group consisting of $C_1$–$C_6$ alkyl, halo, amino, and $C_1$–$C_6$ alkoxy, substituted or unsubstituted $C_3$–$C_6$ cyclyl, $C_3$–$C_6$ heterocyclyl, and, if substituted, the substituent group is selected from one or more of the group consisting of $C_1$–$C_6$ alkyl, $C_1$–$C_6$ alkoxy, halo, amino, and where the $C_3$–$C_6$ heterocyclyl ring contains O, S, or N, branched or unbranched $C_1$–$C_6$ alkoxycarbonyl $C_1$–$C_6$ alkoxy, and carboxy, carboxy $C_1$–$C_6$ alkoxy, carboxy $C_1$–$C_6$ alkyl, hydroxy $C_1$–$C_4$ alkoxycarbonyl, $C_1$–$C_4$ alkoxycarbonyl, where $R^6$ and $R^7$ are such that they can join to form a ring system of the type selected from

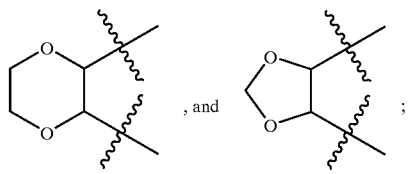

As shown above, ring substituent groups that join to form additional ring structures adjacent the substituted ring can be described with reference to chemical formulas that show wavy lines to indicate that a partial molecule is shown. In these formulas, the wavy lines cut through the ring to which the substituents are joined (in this case, the phenyl ring of formula I), rather than across the bond joining the substituent group to the ring. Accordingly, the partial ring that is shown is the ring to which the substituent groups are shown as being bonded in the general formula.

G is selected from the group consisting of oxygen, sulfur, and nitrogen;

when G is oxygen, $R^9$ and $R^{10}$ are absent;

when G is sulfur, each of $R^9$ and $R^{10}$ is optionally absent or is oxo;

when G is nitrogen, $R^9$ is absent and $R^{10}$ is $C_1$–$C_4$-alkyl.

As used herein, the term "alkyl", alone or in combination, means an acyclic alkyl radical, linear or branched, which, unless otherwise noted, preferably contains from 1 to about 10 carbon atoms and more preferably contains from 1 to about 6 carbon atoms. "Alkyl" also encompasses cyclic alkyl radicals containing from 3 to about 7 carbon atoms, preferably from 3 to 5 carbon atoms. The alkyl radicals can be optionally substituted with groups as defined below. Examples of such alkyl radicals include methyl, ethyl, chloroethyl, hydroxyethyl, n-propyl, isopropyl, n-butyl, cyanobutyl, isobutyl, sec-butyl, tert-butyl, pentyl, aminopentyl, iso-amyl, hexyl, octyl, and the like.

The term "alkenyl" refers to an unsaturated, acyclic hydrocarbon radical, linear or branched, in so much as it contains at least one double bond. Unless otherwise noted, such radicals preferably contain from 2 to about 6 carbon atoms, preferably from 2 to about 4 carbon atoms, more preferably from 2 to about 3 carbon atoms. The alkenyl radicals may be optionally substituted with groups as defined below. Examples of suitable alkenyl radicals include propenyl, 2-chloropropylenyl, buten-1yl, isobutenyl, penten-1yl, 2-methylbuten-1-yl, 3-methylbuten-1-yl, hexen-1-yl, 3-hydroxyhexen-1-yl, hepten-1-yl, octen-1-yl, and the like.

The term "alkynyl" refers to an unsaturated, acyclic hydrocarbon radical, linear or branched, in so much as it contains one or more triple bonds, such radicals preferably containing 2 to about 6 carbon atoms, more preferably from 2 to about 3 carbon atoms. The alkynyl radicals may be optionally substituted with groups as described below. Examples of suitable alkynyl radicals include ethynyl, proynyl, hydroxypropynyl, butyn-1-yl, butyn-2-yl, pentyn-1-yl, pentyn-2-yl, 4-methoxypentyn-2-yl, 3-methylbutyn-1-yl, hexyl-1-yl, hexyn-2-yl, hexyn-3-yl, 3,3-dimethylbutyn-1-yl radicals, and the like.

The term "alkoxy" includes linear or branched oxy-containing radicals, each of which has, unless otherwise noted, alkyl portions of 1 to about 6 carbon atoms, preferably 1 to about 4 carbon atoms, such as methoxy, ethoxy, propoxy, isopropoxy, isobutoxy radicals, and the like.

The term "alkoxyalkyl" also embraces alkyl radicals having one or more alkoxy radicals attached to the alkyl radical, that is, to form monoalkoxyalkyl and dialkoxyalkyl radicals. Examples of such radicals include methoxyalkyls, ethoxyalkyls, propoxyalkyls, isopropoxyalkyls, butoxyalkyls, tert-butoxyalkyls, and the like. The "alkoxy" radicals may be further substituted with one or more halo atoms, such as fluoro, chloro, or bromo, to provide "haloalkoxy" radicals. Examples of such radicals includ fluoromethoxy, chloromethoxy, trifluoromethoxy, difluoromethoxy, trifluoroethoxy, fluoroethoxy, tetrafluoroethoxy, pentafluoroethoxy, fluoropropoxy, and the like.

The term "alkylthio" embraces radicals containing a linear or branched alkyl radical, preferably, unless otherwise noted, of from 1 to about 6 carbon atoms, attached to a divalent sulfur atom. An example of "lower alkylthio", is methylthio ($CH_3$—S—).

The term "alkylthioalkyl" embraces alkylthio radicals, attached to an alkyl group. An example of such radicals is methylthiomethyl.

The term "halo" means radicals comprising halogens, such as fluorine, chlorine, bromine, or iodine.

The term "heterocyclyl" means a saturated or unsaturated mono- or multi-ring carbocycle wherein one or more carbon atoms is replaced by N, S, P, or O. This includes, for example, structures such as:

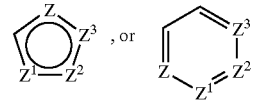

where Z, $Z^1$, $Z^2$, or $Z^3$ is C, S, P, O, or N, with the proviso that one of Z, $Z^1$, $Z^2$, or $Z^3$ is other than carbon, but is not O or S when attached to another Z atom by a double bond or when attached to another O or S atom. Furthermore, the optional substituents are understood to be attached to Z, $Z^1$, $Z^2$, or $Z^3$ only when each is C. The term "heterocycle" also includes fully saturated ring structures, such as piperazinyl, dioxanyl, tetrahydrofuranyl, oxiranyl, aziridinyl, morpholinyl, pyrrolidinyl, piperidinyl, thiazolidinyl, and others.

The term "heteroaryl" means a fully unsaturated heterocycle, which can include, but is not limited to, furyl, thenyl, pyrryl, imidazolyl, pyrazolyl, pyridyl, thiazolyl, quinolinyl, isoquinolinyl, benzothienyl, and indolyl.

In either, "heterocyclyl" or "heteroaryl", the point of attachment to the molecule of interest can be at the heteroatom or elsewhere within the ring.

The term "cycloalkyl" means a mono- or multi-ringed carbocycle wherein each ring contains three to about seven carbon atoms, preferably three to about six carbon atoms, and more preferably three to about five carbon atoms. Examples include radicals, such as cyclopropyl, cyclobutyl, cyclopentyl, cyclohexyl, cycloalkenyl, and cycloheptyl. The term "cycloalkyl" additionally encompasses spiro systems wherein the cycloalkyl ring has a carbon ring atom in common with the seven-membered heterocyclic ring of the benzothiepine.

The term "oxo" means a doubly-bonded oxygen.

The term "aryl" means a fully unsaturated mono- or multi-ring carbocycle, including, but not limited to, substituted or unsubstituted phenyl, naphthyl, or anthracenyl.

The present aminocyanopyridine compounds inhibit the activity of the MK-2 enzyme. When it is said that a subject compound inhibits MK-2, it is meant that the MK-2 enzymatic activity is lower in the presence of the compound than it is under the same conditions in the absence of such compound.

One method of expressing the potency of a compound as an MK-2 inhibitor is to measure the "$IC_{50}$" value of the compound. The $IC_{50}$ value of an MK-2 inhibitor is the concentration of the compound that is required to decrease the MK-2 enzymatic activity by one-half. Accordingly, a compound having a lower $IC_{50}$ value is considered to be a more potent inhibitor than a compound having a higher $IC_{50}$ value. As used herein, aminocyanopyridine compounds that inhibit MK-2 can be referred to as aminocyanopyridine MK-2 inhibitors, or aminocyanopyridine MK-2 inhibiting compounds or MK-2 inhibiting agents.

The tricyclic aminocyanopyridine compounds that are produced in the present invention include benzonapthyridines, pyridochromanes, and pyridothiochromanes.

Examples of tricyclic aminocyanopyridine MK-2 inhibitors that can be produced by the present method are shown in Table I:

TABLE I

Aminocyanopyridine MK-2 Inhibitors

| No. | Structure[a] | Compound Name(s)[b] | MK-2 Avg. IC50 (uM) |
|---|---|---|---|
| 1 | 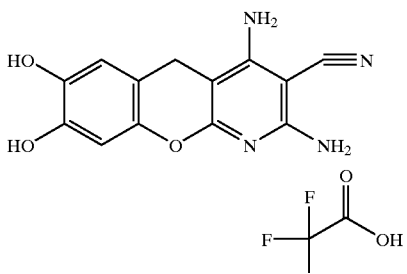 | 2,4-diamino-7,8-dihydroxy-5H-chromeno[2,3-b]pyridine-3-carbonitrile trifluoroacetate | 0.125 |
| 2 | 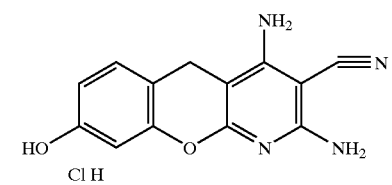 | 2,4-diamino-8-hydroxy-5H-chromeno[2,3-b]pyridine-3-carbonitrile hydrochloride | 0.187 |
| 3 | 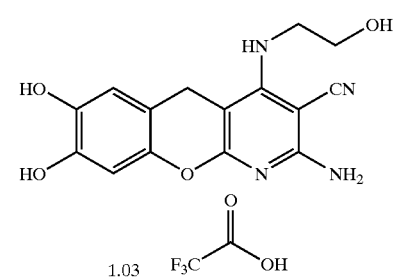 | 2-amino-7,8-dihydroxy-4-[(2-hydroxyethyl)amino]-5H-chromeno[2,3-b]pyridine-3-carbonitrile trifluoroacetate | 0.237 |
| 4 | 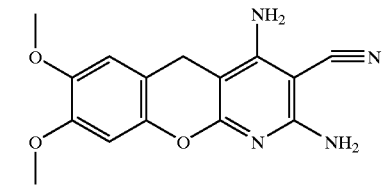 | 2,4-diamino-7,8-dimethoxy-5H-chromeno[2,3-b]pyridine-3-carbonitrile | 0.335 |
| 5 | 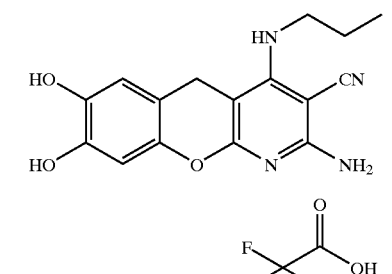 | 2-amino-7,8-dihydroxy-4-(propylamino)-5H-chromeno[2,3-b]pyridine-3-carbonitrile trifluoroacetate | 0.403 |

TABLE I-continued

Aminocyanopyridine MK-2 Inhibitors

| No. | Structure[a] | Compound Name(s)[b] | MK-2 Avg. IC50 (uM) |
|---|---|---|---|
| 6 | 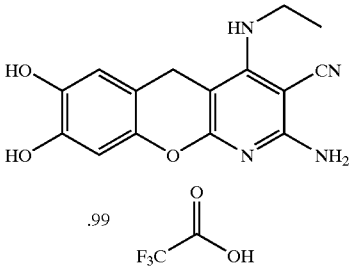 | 2-amino-4-(ethylamino)-7,8-di-hydroxy-5H-chromeno[2,3-b]pyridine-3-carbonitrile trifluoroacetate | 0.419 |
| 7 | 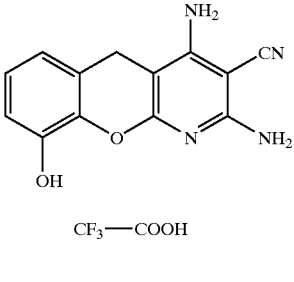 | 2,4-diamino-9-hydroxy-5H-chromeno[2,3-b]pyridine-3-carbonitrile trifluoroacetate | 0.459 |
| 8 | 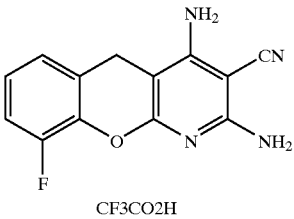 | 2,4-diamino-9-fluoro-5H-chromeno[2,3-b]pyridine-3-carbonitrile | 0.471 |
| 9 | 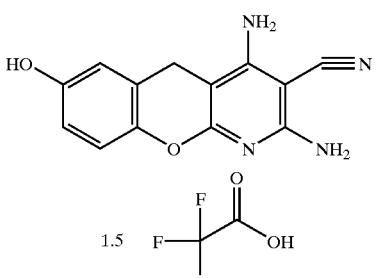 | 2,4-diamino-7-hydroxy-5H-chromeno[2,3-b]pyridine-3-carbonitrile trifluoroacetate | 0.473 |
| 10 | 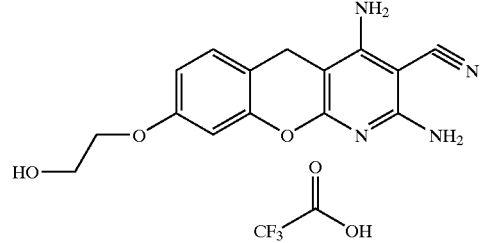 | 2,4-diamino-8-(2-hydroxyethoxy)-5H-chromeno[2,3-b]pyridine-3-carbonitrile trifluoroacetate | 0.483 |

TABLE I-continued

Aminocyanopyridine MK-2 Inhibitors

| No. | Structure[a] | Compound Name(s)[b] | MK-2 Avg. IC50 (uM) |
|---|---|---|---|
| 11 | | 8,10-diamino-2,3-dihydro-11H-[1,4]diox-ino[2',3':6,7]chromeno[2,3-b]py-ridine-9-carbonitrile trifluoroacetate | 0.488 |
| 12 | | 2,4,7-triamino-5H-chromeno[2,3-b]py-ridine-3-carbonitrile | 0.514 |
| 13 | | 2,4-diamino-5H-chromeno[2,3-b]py-ridine-3-carbonitrile trifluoroacetate | 0.563 |
| 14 | | 2,4-diamino-8-(2-ethoxyethoxy)-7-hy-droxy-5H-chromeno[2,3-b]py-ridine-3-carbonitrile trifluoroacetate | 0.62 |
| 15 | | 2,4-diamino-9-hydroxy-8-methoxy-5H-chro-meno[2,3-b]pyridine-3-carbo-nitrile trifluoroacetate | 0.682 |

TABLE I-continued

Aminocyanopyridine MK-2 Inhibitors

| No. | Structure | Compound Name(s) | MK-2 Avg. IC50 (uM) |
|---|---|---|---|
| 16 | 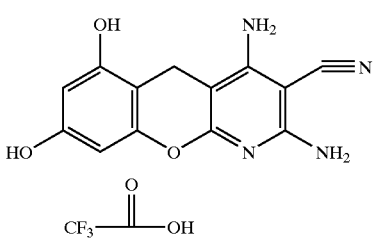 | 2,4-diamino-6,8-dihydroxy-5H-chromeno[2,3-b]pyridine-3-carbonitrile trifluoroacetate | 0.694 |
| 17 | 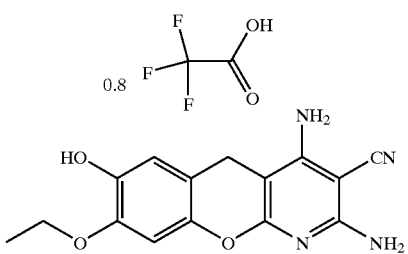 | 2,4-diamino-8-ethoxy-7-hydroxy-5H-chromeno[2,3-b]pyridine-3-carbonitrile trifluoroacetate | 0.773 |
| 18 | 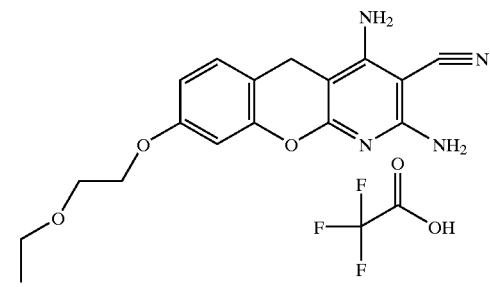 | 2,4-diamino-8-(2-ethoxyethoxy)-5H-chromeno[2,3-b]pyridine-3-carbonitrile | 0.817 |
| 19 | 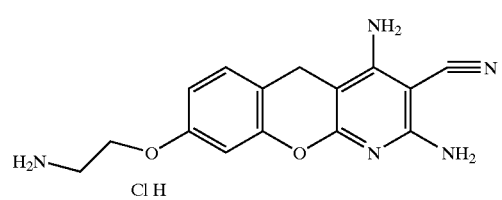 | 2,4-diamino-8-(2-aminoethoxy)-5H-chromeno[2,3-b]pyridine-3-carbonitrile hydrochloride | 0.82 |
| 20 | 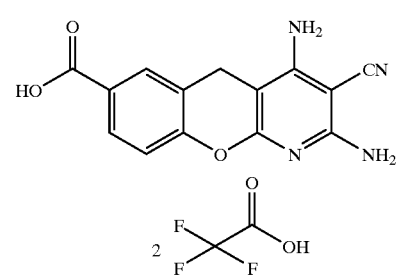 | 2,4-diamino-3-cyano-5H-chromeno[2,3-b]pyridine-7-carboxylic acid trifluoroacetate | 0.857 |

TABLE I-continued

Aminocyanopyridine MK-2 Inhibitors

| No. | Structure[a] | Compound Name(s)[b] | MK-2 Avg. IC50 (uM) |
|---|---|---|---|
| 21 | 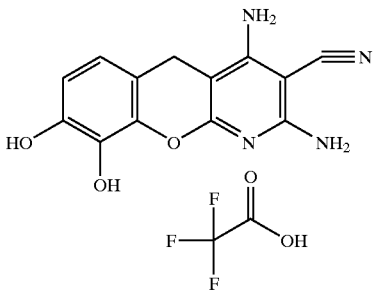 | 2,4-diamino-8,9-dihydroxy-5H-chromeno[2,3-b]pyridine-3-carbonitrile trifluoroacetate | 0.857 |
| 22 | 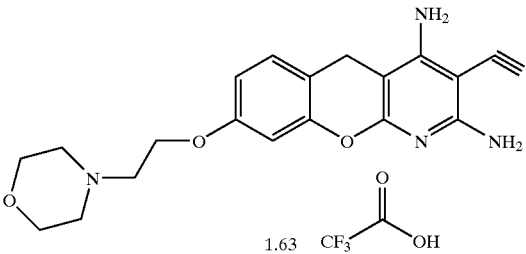 1.63 | 2,4-diamino-8-(2-morpholin-4-yl-ethoxy)-5H-chromeno[2,3-b]pyridine-3-carbonitrile trifluoroacetate | 0.91 |
| 23 | 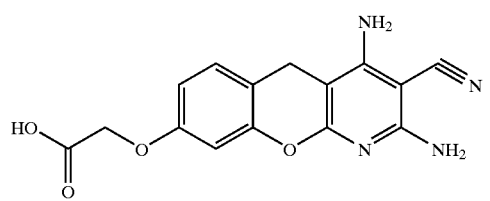 | [(2,4-diamino-3-cyano-5H-chromeno[2,3-b]pyridin-8-yl)oxy]acetic acid trifluoroacetate | 0.916 |
| 24 | 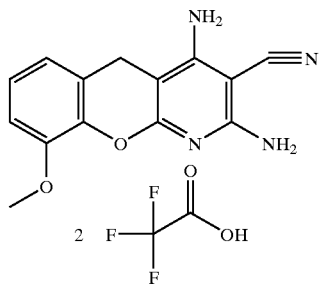 2 | 2,4-diamino-9-methoxy-5H-chromeno[2,3-b]pyridine-3-carbonitrile trifluoroacetate | 1.37 |
| 25 | 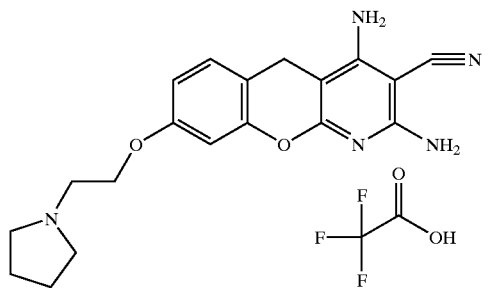 | 2,4-diamino-8-(2-pyrrolidin-1-yl-ethoxy)-5H-chromeno[2,3-b]pyridine-3-carbonitrile | 1.68 |

TABLE I-continued

Aminocyanopyridine MK-2 Inhibitors

| No. | Structure[a] | Compound Name(s)[b] | MK-2 Avg. IC50 (uM) |
|---|---|---|---|
| 26 | 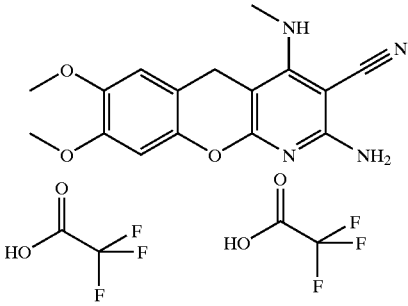 | 2-amino-7,8-dimethoxy-4-(methyl-amino)-5H-chromeno[2,3-b]py-ridine-3-carbonitrile bis(trifluoroacetate) | 1.69 |
| 27 | 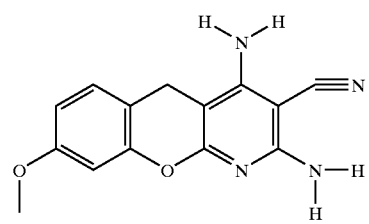 | 2,4-diamino-8-methoxy-5H-chromeno[2,3-b]pyridine-3-carbonitrile | 1.72 |
| 28 | 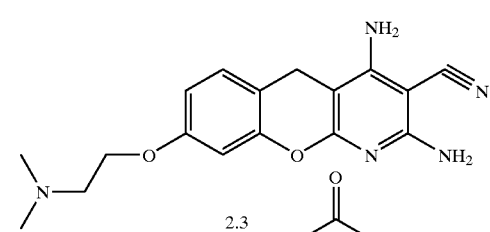 | 2,4-diamino-8-[2-(di-methylamino)ethoxy]-5H-chromeno[2,3-b]pyridine-3-carbonitrile trifluoroacetate | 1.75 |
| 29 | 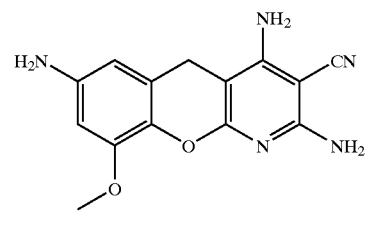 | 2,4,7-triamino-9-methoxy-5H-chromeno[2,3-b]pyridine-3-carbonitrile trifluoroacetate | 1.79 |
| 30 | 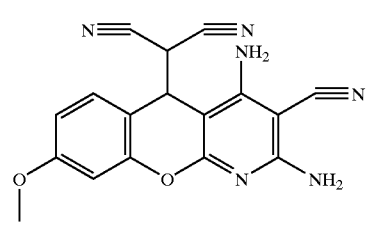 | 2(2,4-diamino-3-cyano-8-methoxy-5H-chromeno[2,3-b]pyridin-5-yl)malononitrile | 1.94 |
| 31 | 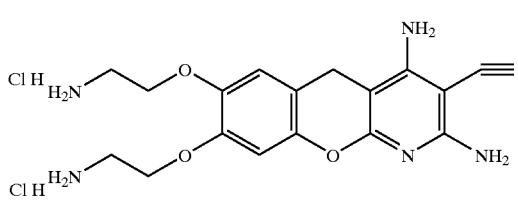 | 2,4-diamino-7,8-di[2-(amino)ethoxy]-5H-chromeno[2,3-b]pyridine-3-carbonitrile trifluoroacetate | 2.55 |

TABLE I-continued

Aminocyanopyridine MK-2 Inhibitors

| No. | Structure[a] | Compound Name(s)[b] | MK-2 Avg. IC50 (uM) |
|---|---|---|---|
| 32 | 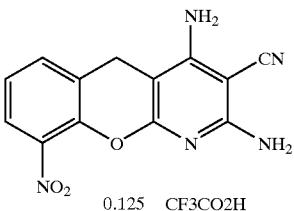 0.125 CF3CO2H | 2,4-diamino-9-nitro-5H-chromeno[2,3-b]pyridine-3-carbonitrile | 2.58 |
| 33 | 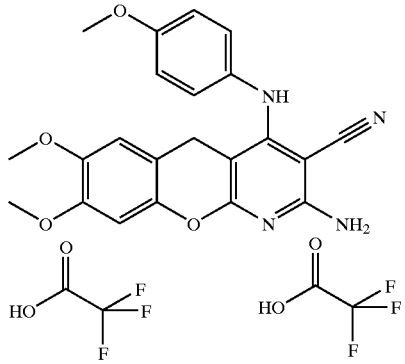 | 2-amino-7,8-dimethoxy-4-[(4-methoxyphenyl)amino]-5H-chromeno[2,3-b]pyridine-3-carbonitrile bis(trifluoroacetate) | 2.98 |
| 34 | 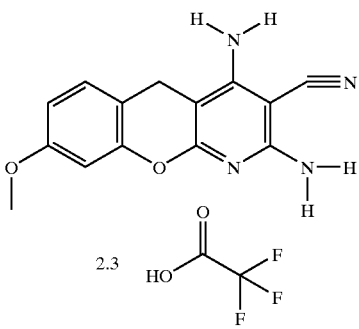 2.3 | 2,4-diamino-8-methoxy-5H-chromeno[2,3-b]pyridine-3-carbonitrile | 3.24 |
| 35 | 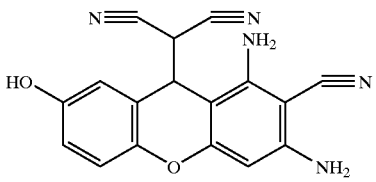 | 2(2,4-diamino-3-cyano-7-hydroxy-5H-chromeno[2,3-b]pyridin-5-yl)malononitrile | 3.8 |
| 36 | 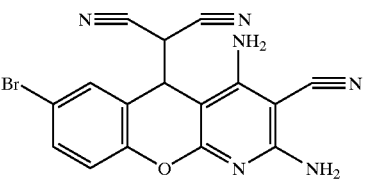 | 2(2,4-diamino-3-cyano-7-bromo-5H-chromeno[2,3-b]pyridin-5-yl)malononitrile | 4.22 |

TABLE I-continued

Aminocyanopyridine MK-2 Inhibitors

| No. | Structure[a] | Compound Name(s)[b] | MK-2 Avg. IC50 (uM) |
|---|---|---|---|
| 37 | | 2-amino-8-ethoxy-4-(ethyl-amino)-5H-chromeno[2,3-b]pyridine-3-carbonitrile | 4.76 |
| 38 | | 2,4,9-triamino-5H-chromeno[2,3-b]pyridine-3-carbonitrile trifluoroacetate | 5.01 |
| 39 | | 2,4,7-triamino-5H-thiochromeno[2,3-b]pyridine-3-carbonitrile trifluoroacetate | 5.6 |
| 40 | | 2-amino-7,8-dimethoxy-4-[(4-methoxyphenyl)amino]-5H-chromeno[2,3-b]pyridine-3-carbonitrile | 6.11 |
| 41 | | 2(2,4-diamino-3-cyano-7-methoxy-5H-chromeno[2,3-b]pyridin-5-yl)malononitrile | 6.18 |

TABLE I-continued

Aminocyanopyridine MK-2 Inhibitors

| No. | Structure[a] | Compound Name(s)[b] | MK-2 Avg. IC50 (uM) |
|---|---|---|---|
| 42 | 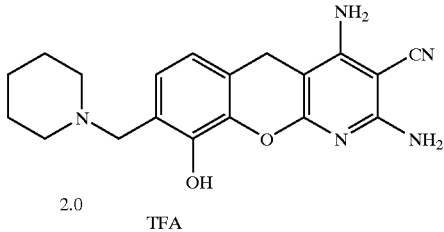 | 2,4-diamino-9-hydroxy-8-(piperidin-1-yl-methyl)-5H-chromeno[2,3-b]pyridine-3-carbonitrile trifluoroacetate | 8.28 |
| 43 | 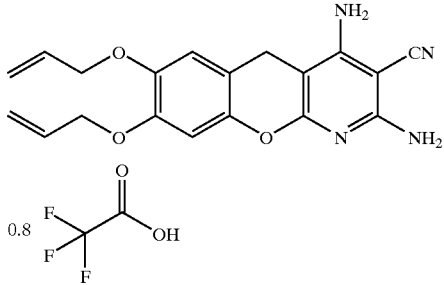 | 7,8-bis(allyloxy)-2,4-diamino-5H-chromeno[2,3-b]pyridine-3-carbonitrile trifluoroacetate | 9.6 |
| 44 | 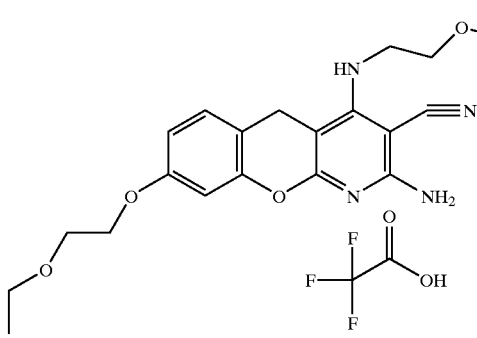 | 2-amino-8-(2-ethoxyethoxy)-4-[(2-ethoxyethyl)amino]-5H-chromeno[2,3-b]pyridine-3-carbonitrile | 9.66 |
| 45 | 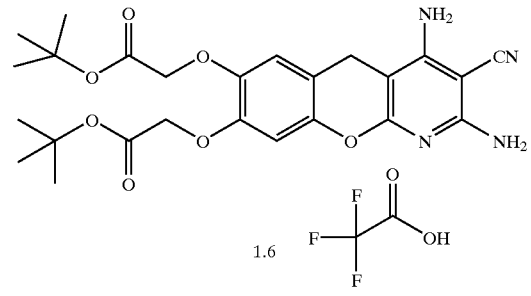 | tert-butyl{[2,4-diamino-7-(2-tert-butoxy-2-oxoethoxy)-3-cyano-5H-chromeno[2,3-b]pyridin-8-yl]oxy}acetate trifluoroacetate | 10.3 |
| 46 | 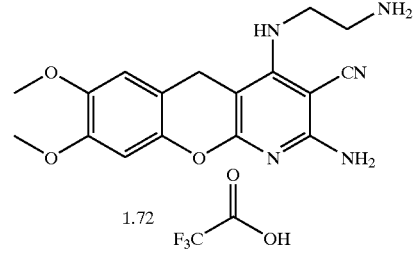 | 2-amino-4-[(2-aminoethyl)amino]-7,8-dimethoxy-5H-chromeno[2,3-b]pyridine-3-carbonitrile trifluoroacetate | 11.5 |

TABLE I-continued

Aminocyanopyridine MK-2 Inhibitors

| No. | Structure[a] | Compound Name(s)[b] | MK-2 Avg. IC50 (uM) |
|---|---|---|---|
| 47 | 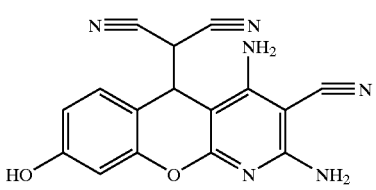 | 2(2,4-diamino-3-cyano-8-hydroxy-5H-chromeno[2,3-b]pyridine-5-yl)malononitrile | 12.8 |
| 48 | 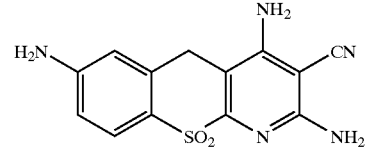 | 2,4,7-triamino-5H-thiochromeno[2,3-b]pyridine-3-carbonitrile 10,10-dioxide | 14.4 |
| 49 | 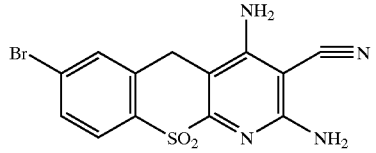 | 2,4-diamino-7-bromo-5H-chromeno[2,3-b]pyridine-3-carbonitrile | 15.1 |
| 50 | 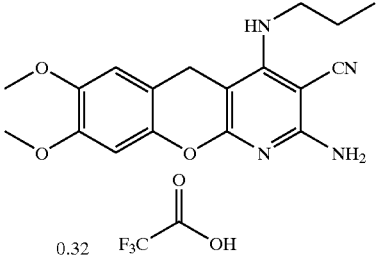 | 2-amino-7,8-dimethoxy-4-(propylamino)-5H-chromeno[2,3-b]pyridine-3-carbonitrile | 15.6 |
| 51 | 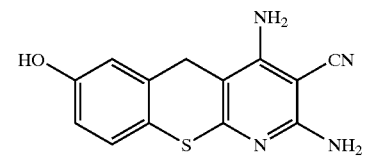 | 2,4-diamino-7-hydroxy-5H-thiochromeno[2,3-b]pyridine-3-carbonitrile | 17.4 |
| 52 | 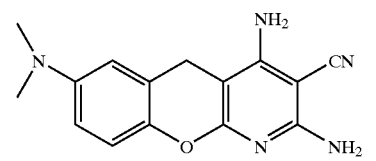 | 2,4-diamino-7-(dimethylamino)-5H-chromeno[2,3-b]pyridine-3-carbonitrile | 17.6 |
| 53 | 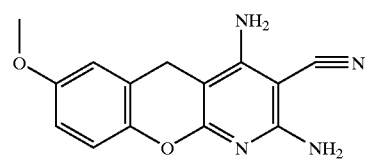 | 2,4-diamino-7-methoxy-5H-chromeno[2,3-b]pyridine-3-carbonitrile | 19.7 |

TABLE I-continued

Aminocyanopyridine MK-2 Inhibitors

| No. | Structure[a] | Compound Name(s)[b] | MK-2 Avg. IC50 (uM) |
|---|---|---|---|
| 54 | | 2(2,4-diamino-3-cyano-9-methoxy-5H-chromeno[2,3-b]pyridin-5-yl)malononitrile | 21.2 |
| 55 | | 2-amino-4-(benzylamino)-7,8-dimethoxy-5H-chromeno[2,3-b]pyridine-3-carbonitrile trifluoroacetate | 27.4 |
| 56 | | 8-(allyloxy)-2,4-diamino-5H-chromeno[2,3-b]pyridine-3-carbonitrile trifluoroacetate | 33.8 |
| 57 | | 2,4-diamino-9-fluoro-5H-thiochromeno[2,3-b]pyridine-3-carbonitrile trifluoroacetate | 42.2 |
| 58 | | 2,4-diamino-7-methoxy-5H-chromeno[2,3-b]pyridine-3-carbonitrile trifluoroacetate | 43 |

TABLE I-continued

Aminocyanopyridine MK-2 Inhibitors

| No. | Structure[a] | Compound Name(s)[b] | MK-2 Avg. IC50 (uM) |
|---|---|---|---|
| 59 | 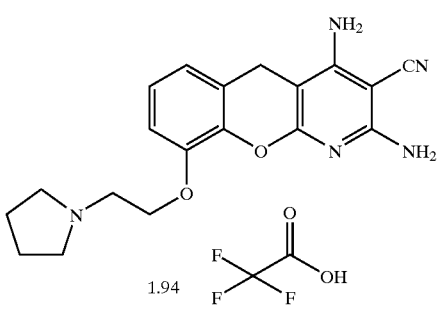 | 2,4-diamino-9-(2-pyrrolidin-1-yl-ethoxy)-5H-chromeno[2,3-b]pyridine-3-carbonitrile trifluoroacetate | 45.2 |
| 60 | 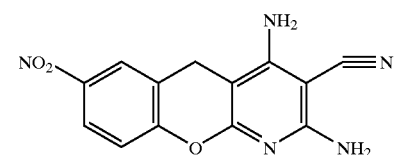 | 2,4-diamino-7-nitro-5H-chromeno[2,3-b]pyridine-3-carbonitrile | 62.2 |
| 61 | 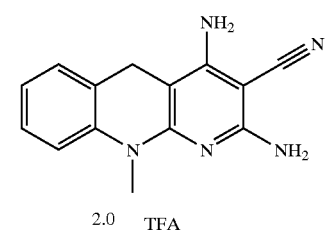 | 2,4-diamino-10-methyl-5,10-dihydrobenzo[b]-1,8-naphthyridine-3-carbonitrile trifluoroacetate | 70.1 |
| 62 | 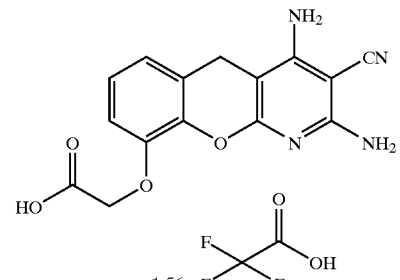 | [(2,4-diamino-3-cyano-5H-chromeno[2,3-b]pyridin-9-yl)oxy]acetic acid trifluoroacetate | 72.2 |
| 63 | 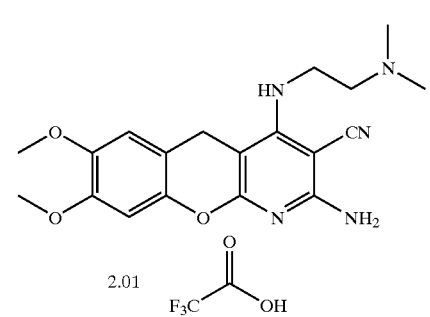 | 2-amino-4-{[2-(dimethylamino)ethyl]amino}-7,8-dimethoxy-5H-chromeno[2,3-b]pyridine-3-carbonitrile trifluoroacetate | 79.1 |

TABLE I-continued

Aminocyanopyridine MK-2 Inhibitors

| No. | Structure[a] | Compound Name(s)[b] | MK-2 Avg. IC50 (uM) |
|---|---|---|---|
| 64 | 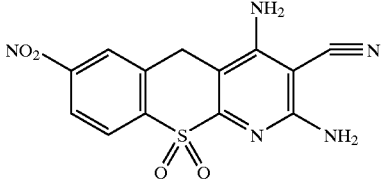 | 2,4-diamino-7-nitro-5H-thio-chromeno[2,3-b]pyridine-3-carbo-nitrile 10,10-dioxide | 80.8 |
| 65 | 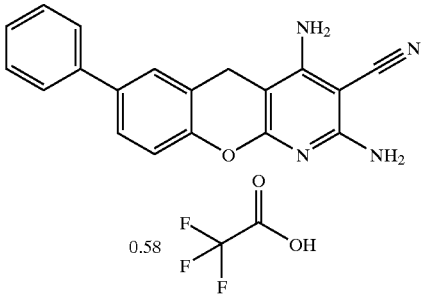 | 2,4-diamino-7-phenyl-5H-chro-meno[2,3-b]pyridine-3-carbo-nitrile trifluoroacetate | 83.8 |
| 66 | 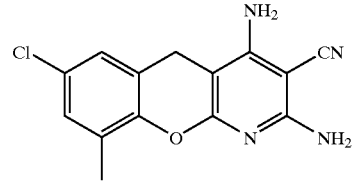 | 2,4-diamino-7-chloro-9-methyl-5H-chro-meno[2,3-b]pyridine-3-carbo-nitrile | 136 |
| 67 | 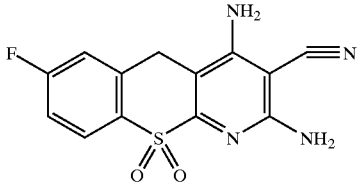 | 2,4-diamino-7-fluoro-5H-thio-chromeno[2,3-b]pyridine-3-carbo-nitrile 10,10-dioxide | 142 |
| 68 | 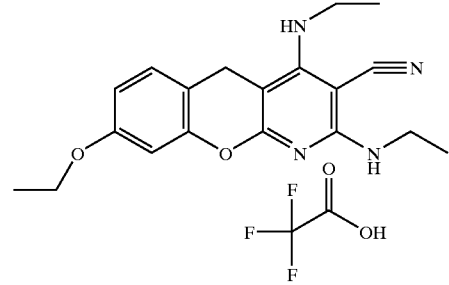 | 8-ethoxy-2,4-bis(ethylamino)-5H-chro-meno[2,3-b]pyridine-3-carbo-nitrile | 148 |
| 69 | 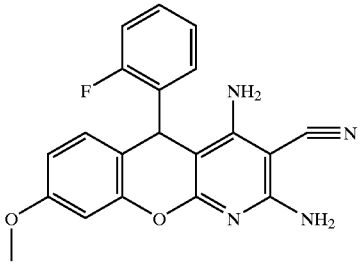 | 2,4-diamino-5-(2-fluoro-phenyl)-8-meth-oxy-5H-chromeno[2,3-b]py-ridine-3-carbonitrile | 151 |

TABLE I-continued

Aminocyanopyridine MK-2 Inhibitors

| No. | Structure[a] | Compound Name(s)[b] | MK-2 Avg. IC50 (uM) |
|---|---|---|---|
| 70 | 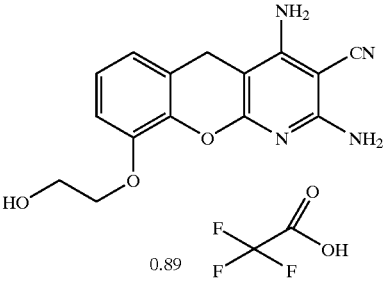 | 2,4-diamino-9-(2-hydroxyethoxy)-5H-chromeno[2,3-b]pyridine-3-carbonitrile trifluoroacetate | 154 |
| 71 | 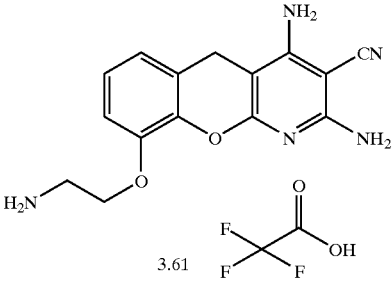 | 2,4-diamino-9-(2-aminoethoxy)-5H-chromeno[2,3-b]pyridine-3-carbonitrile trifluoroacetate | 161 |
| 72 | 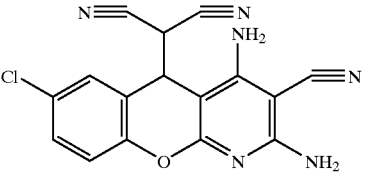 | 2(2,4-diamino-3-cyano-7-chloro-5H-chromeno[2,3-b]pyridin-5-yl)malononitrile | 200 |
| 73 | 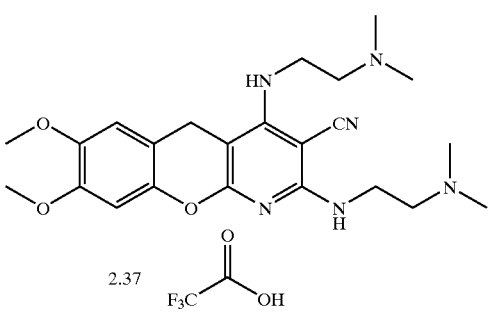 | 2,4-bis{[2-(dimethylamino)ethyl]amino}-7,8-dimethoxy-5H-chromeno[2,3-b]pyridine-3-carbonitrile trifluoroacetate | 200 |
| 74 | 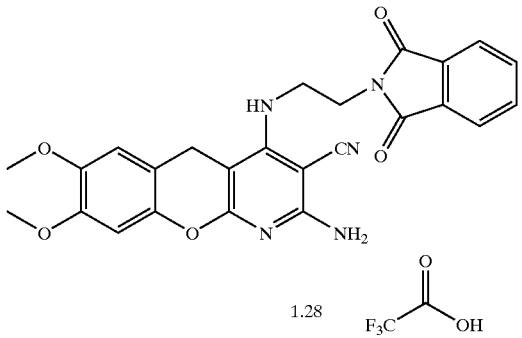 | 2-amino-4-{[2-(1,3-dioxo-1,3-dihydro-2H-isoindol-2-yl)ethyl]amino}-7,8-dimethoxy-5H-chromeno[2,3-b]pyridine-3-carbonitrile trifluoroacetate | 200 |

TABLE I-continued

Aminocyanopyridine MK-2 Inhibitors

| No. | Structure[a] | Compound Name(s)[b] | MK-2 Avg. IC50 (uM) |
|---|---|---|---|
| 75 | 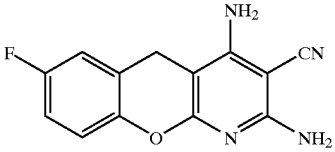 0.75   CF3—COOH | 2,4-diamino-7-fluoro-5H-chromeno[2,3-b]pyridine-3-carbonitrile trifluoroacetate | 200 |
| 76 | 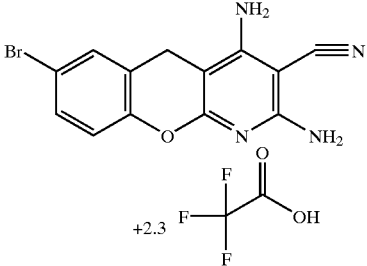 +2.3 | 2,4-diamino-7-bromo-5H-chromeno[2,3-b]pyridine-3-carbonitrile trifluoroacetate | 200 |
| 77 | 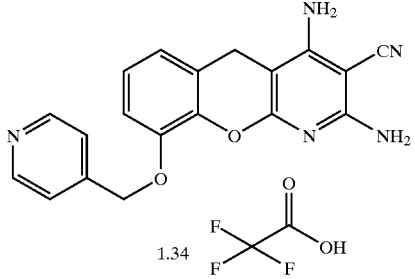 1.34 | 2,4-diamino-9-(pyridin-4-ylmethoxy)-5H-chromeno[2,3-b]pyridine-3-carbonitrile trifluoroacetate | 200 |
| 78 | 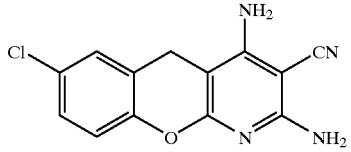 1.75   CF3CO2H | 2,4-diamino-7-chloro-5H-chromeno[2,3-b]pyridine-3-carbonitrile | 200 |
| 79 | 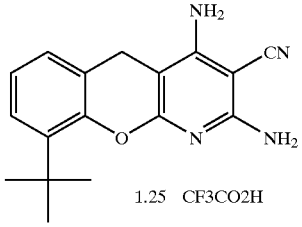 1.25   CF3CO2H | 2,4-diamino-9-tert-butyl-5H-chromeno[2,3-b]pyridine-3-carbonitrile | 200 |
| 80 | 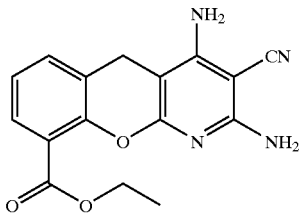 | ethyl 2,4-diamino-3-cyano-5H-chromeno[2,3-b]pyridine-9-carboxylate | 200 |

TABLE I-continued

Aminocyanopyridine MK-2 Inhibitors

| No. | Structure[a] | Compound Name(s)[b] | MK-2 Avg. IC50 (uM) |
|---|---|---|---|
| 81 | 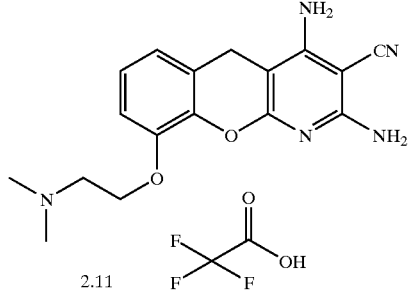 | 2,4-diamino-9-[2-(dimethylamino)ethoxy]-5H-chromeno[2,3-b]pyridine-3-carbonitrile trifluoroacetate | 200 |
| 82 | 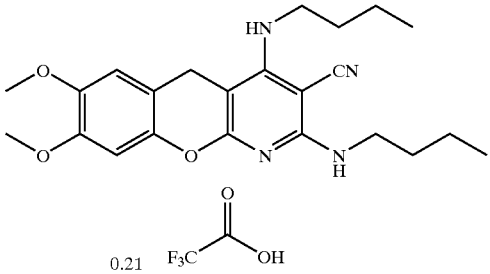 | 2,4-bis(butylamino)-7,8-dimethoxy-5H-chromeno[2,3-b]pyridine-3-carbonitrile | 200 |
| 83 | 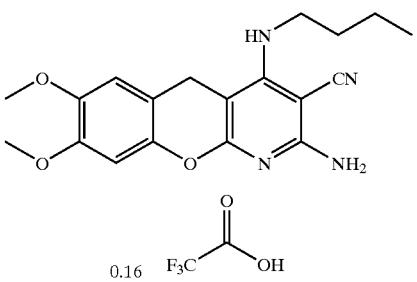 | 2-amino-4-(butylamino)-7,8-dimethoxy-5H-chromeno[2,3-b]pyridine-3-carbonitrile | 200 |
| 84 | 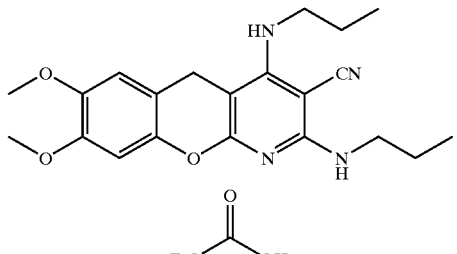 | 7,8-dimethoxy-2,4-bis(propylamino)-5H-chromeno[2,3-b]pyridine-3-carbonitrile | 200 |
| 85 | 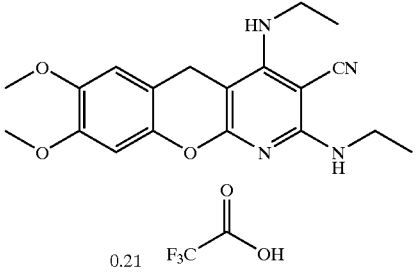 | 2,4-bis(ethylamino)-7,8-dimethoxy-5H-chromeno[2,3-b]pyridine-3-carbonitrile | 200 |

TABLE I-continued

Aminocyanopyridine MK-2 Inhibitors

| No. | Structure[a] | Compound Name(s)[b] | MK-2 Avg. IC50 (uM) |
|---|---|---|---|
| 86 | 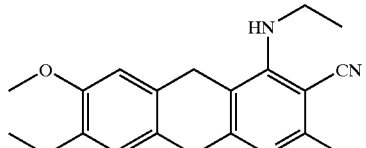 0.24 | 2-amino-4-(ethylamino)-7,8-di-methoxy-5H-chromeno[2,3-b]py-ridine-3-carbonitrile | 200 |
| 87 | 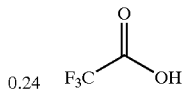 | 2,4-diamino-6,8-dimethoxy-5H-chromeno[2,3-b]pyridine-3-carbonitrile trifluoroacetate | 200 |
| 88 | 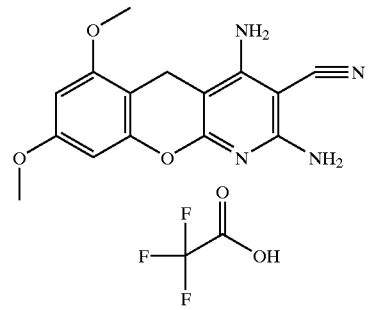 1.25 | 2,4-diamino-7-(trifluoromethoxy)-5H-chromeno[2,3-b]pyridine-3-carbonitrile trifluoroacetate | 200 |
| 89 | 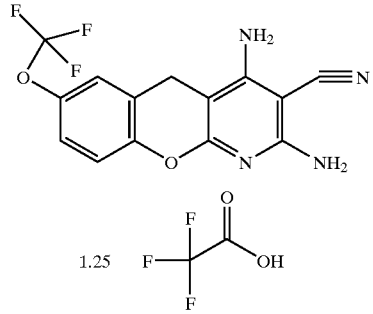 1.75 | 2,4-diamino-7-bromo-9-methoxy-5H-chromeno[2,3-b]pyridine-3-carbonitrile trifluoroacetate | 200 |

TABLE I-continued

Aminocyanopyridine MK-2 Inhibitors

| No. | Structure[a] | Compound Name(s)[b] | MK-2 Avg. IC50 (uM) |
|---|---|---|---|
| 90 | 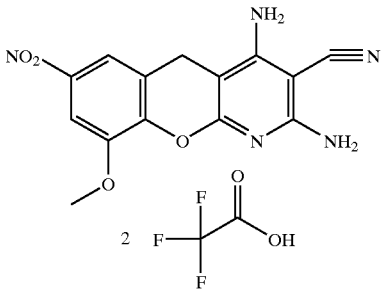 | 2,4-diamino-9-methoxy-7-nitro-5H-chromeno[2,3-b]pyridine-3-carbonitrile trifluoroacetate | 200 |
| 91 | 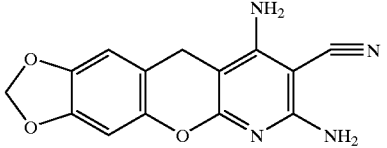 | 7,9-diamino-10H-[1,3]dioxolo[6,7]chromeno[2,3-b]pyridine-8-carbonitrile | 200 |
| 92 | 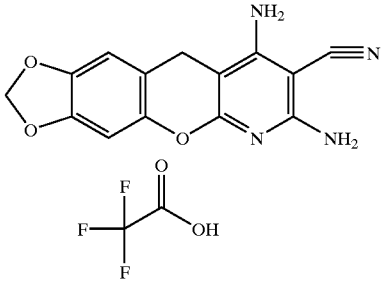 | 7,9-diamino-10H-[1,3]dioxolo[6,7]chromeno[2,3-b]pyridine-8-carbonitrile trifluoroacetate | 200 |
| 93 | 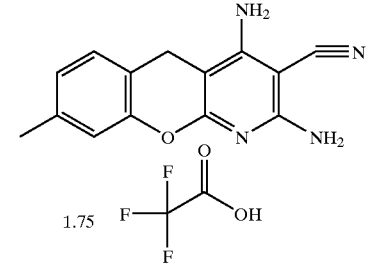 | 2,4-diamino-8-methyl-5H-chromeno[2,3-b]pyridine-3-carbonitrile trifluoroacetate | 200 |
| 94 | 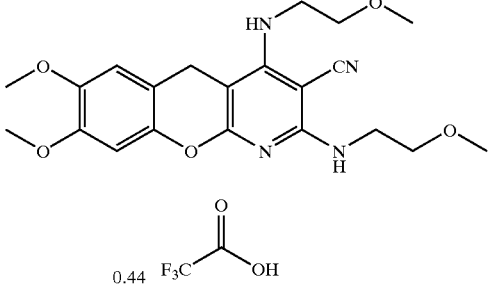 | 7,8-dimethoxy-2,4-bis[(2-methoxyethyl)amino]-5H-chromeno[2,3-b]pyridine-3-carbonitrile | 200 |

TABLE I-continued

Aminocyanopyridine MK-2 Inhibitors

| No. | Structure[a] | Compound Name(s)[b] | MK-2 Avg. IC50 (uM) |
|---|---|---|---|
| 95 | 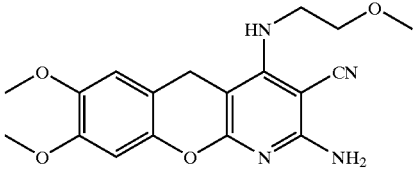 0.36 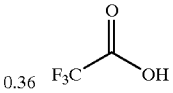 | 2-amino-7,8-dimethoxy-4-[(2-methoxyethyl)amino]-5H-chromeno[2,3-b]pyridine-3-carbonitrile | 200 |
| 96 | 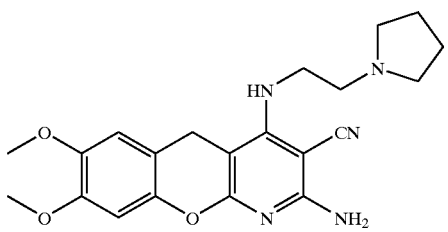 2.1 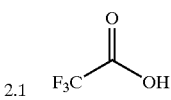 | 2-amino-7,8-dimethoxy-4-[(2-pyrrolidin-1-ylethyl)amino]-5H-chromeno[2,3-b]pyridine-3-carbonitrile | 200 |
| 97 | 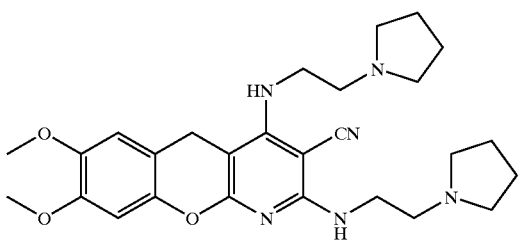 5.8 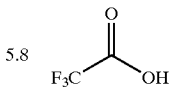 | 7,8-dimethoxy-2,4-bis[(2-pyrrolidin-1-ylethyl)amino]-5H-chromeno[2,3-b]pyridine-3-carbonitrile | 200 |
| 98 | 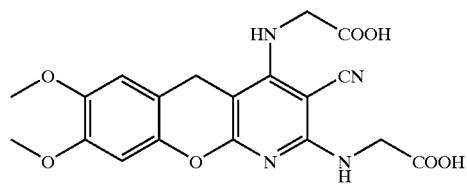 0.41 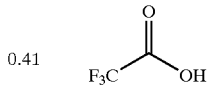 | 2,4-bis(glycinyl)-7,8-dimethoxy-5H-chromeno[2,3-b]pyridine-3-carbonitrile trifluoroacetate | 200 |

TABLE I-continued

Aminocyanopyridine MK-2 Inhibitors

| No. | Structure[a] | Compound Name(s)[b] | MK-2 Avg. IC50 (uM) |
|---|---|---|---|
| 99 | 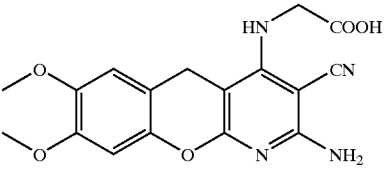 0.32 | N-(2-amino-3-cyano-7,8-dimethoxy-5H-chromeno[2,3-b]pyridine-4-yl)glycine | 200 |
| 100 | 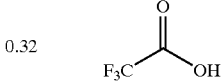 | 2,4-diamino-3-cyano-5H-chromeno[2,3-b]pyridine-9-carboxylic acid bis(trifluoroacetate) | 200 |
| 101 | 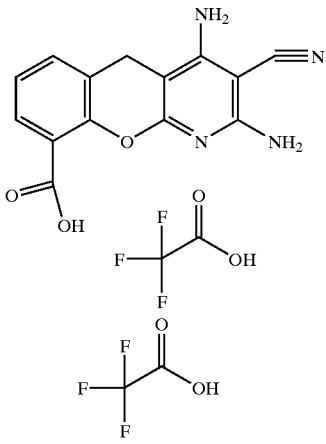 | 2,4-diamino-6-methoxy-5H-chromeno[2,3-b]pyridine-3-carbonitrile bis(trifluoroacetate) | 200 |
| 102 | 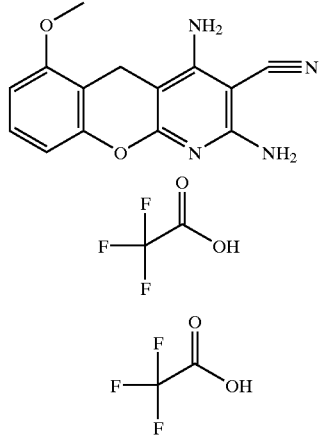 | 2,4-diamino-9-bromo-7-chloro-5H-chromeno[2,3-b]pyridine-3-carbonitrile trifluoroacetate | 200 |

TABLE I-continued

Aminocyanopyridine MK-2 Inhibitors

| No. | Structure[a] | Compound Name(s)[b] | MK-2 Avg. IC50 (uM) |
|---|---|---|---|
| 103 | 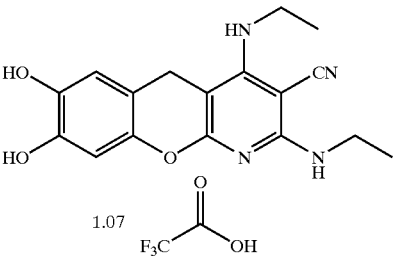 1.07 | 2,4-bis(ethylamino)-7,8-dihydroxy-5H-chromeno[2,3-b]pyridine-3-carbonitrile trifluoroacetate | 200 |
| 104 | 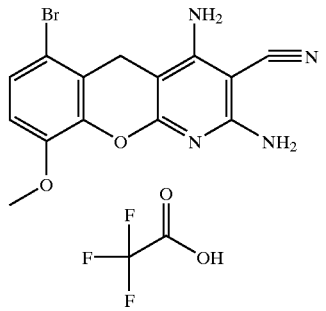 3.76 TFA | 2,4-diamino-6-bromo-9-methoxy-5H-chromeno[2,3-b]pyridine-3-carbonitrile trifluoroacetate | 200 |
| 105 | 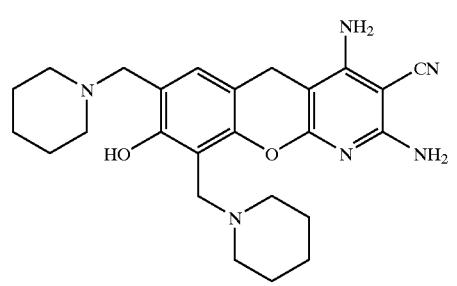 | 2,4-diamino-8-hydroxy-7,9-bis(piperidin-1-ylmethyl)-5H-chromeno[2,3-b]pyridine-3-carbonitrile trifluoroacetate | 200 |
| 106 | 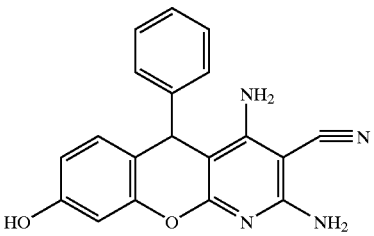 | 2,4-diamino-5-phenyl-8-hydroxy-5H-chromeno[2,3-b]pyridine-3-carbonitrile | 200 |
| 107 | 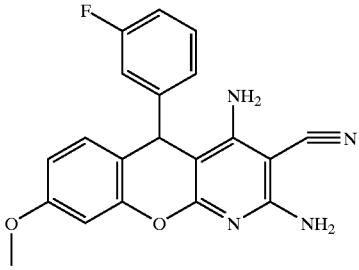 | 2,4-diamino-5-(3-fluoro-phenyl)-8-methoxy-5H-chromeno[2,3-b]pyridine-3-carbonitrile | 200 |

TABLE I-continued

Aminocyanopyridine MK-2 Inhibitors

| No. | Structure[a] | Compound Name(s)[b] | MK-2 Avg. IC50 (uM) |
|---|---|---|---|
| 108 | 3.71 TFA | 2,4-diamino-9-hydroxy-6,8-bis(piperidin-1-ylmethyl)-5H-chromeno[2,3-b]pyridine-3-carbonitrile trifluoroacetate | 200 |
| 109 | | 2,4-diamino-7-bromo-8-methoxy-5H-chromeno[2,3-b]pyridine-3-carbonitrile | 200 |
| 110 | | 2,4-diamino-5-phenyl-8-methoxy-5H-chromeno[2,3-b]pyridine-3-carbonitrile | 200 |
| 111 | | 2,4-diamino-9-fluoro-5H-thiochromeno[2,3-b]pyridine-3-carbonitrile 10,10-dioxide | 200 |
| 112 | | 2,4-diamino-7-nitro-5H-thiochromeno[2,3-b]pyridine-3-carbonitrile | 200 |
| 113 | | 2,4-diamino-7-methoxy-5H-thiochromeno[2,3-b]pyridine-3-carbonitrile 10,10-dioxide | 200 |

TABLE I-continued

Aminocyanopyridine MK-2 Inhibitors

| No. | Structure[a] | Compound Name(s)[b] | MK-2 Avg. IC50 (uM) |
|---|---|---|---|
| 114 | 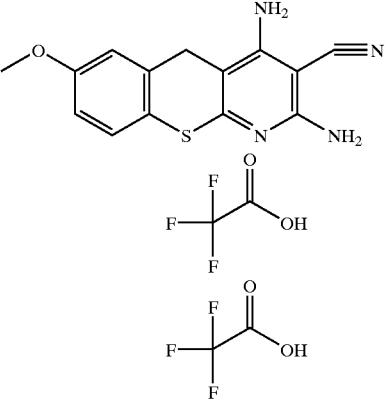 | 2,4-diamino-7-methoxy-5H-thio-chromeno[2,3-b]pyridine-3-carbonitrile bis(trifluoroacetate) | 200 |
| 115 | 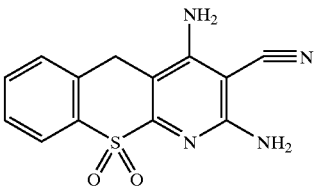 | 2,4-diamino-5H-thiochromeno[2,3-b]pyridine-3-carbonitrile 10,10-dioxide | 200 |
| 116 | 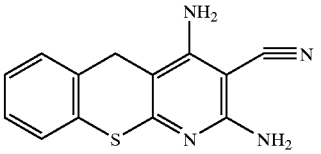 | 2,4-diamino-5H-thiochromeno[2,3-b]pyridine-3-carbonitrile trifluoroacetate | 200 |
| 117 | 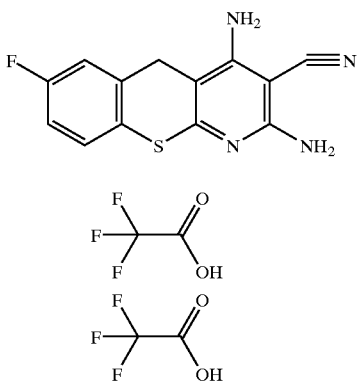 | 2,4-diamino-7-fluoro-5H-thio-chromeno[2,3-b]pyridine-3-carbonitrile bis(trifluoroacetate) | 200 |

TABLE I-continued

Aminocyanopyridine MK-2 Inhibitors

| No. | Structure[a] | Compound Name(s)[b] | MK-2 Avg. IC50 (uM) |
|---|---|---|---|
| 118 | | 2-amino-7,9-dimethyl-5-oxo-5H-chromeno[2,3-b]pyridine-3-carbonitrile | 200 |
| 119 | | 2-amino-7-isopropyl-5-oxo-5H-chromeno[2,3-b]pyridine-3-carbonitrile | 200 |
| 120 | | 2-amino-7-ethyl-5-oxo-5H-chromeno[2,3-b]pyridine-3-carbonitrile | 200 |
| 121 | | 2-amino-7-methyl-5-oxo-5H-chromeno[2,3-b]pyridine-3-carbonitrile | 200 |
| 122 | | 2-amino-7-chloro-5-oxo-5H-chromeno[2,3-b]pyridine-3-carbonitrile | 200 |
| 123 | | 2-amino-7-bromo-5-oxo-5H-chromeno[2,3-b]pyridine-3-carbonitrile | 200 |
| 124 | | 2-amino-5-oxo-5H-chromeno[2,3-b]pyridine-3-carbonitrile | 200 |

TABLE I-continued

Aminocyanopyridine MK-2 Inhibitors

| No. | Structure[a] | Compound Name(s)[b] | MK-2 Avg. IC50 (uM) |
|---|---|---|---|
| 125 | | 3-amino-5H-pyrido[3,4-b][1,4]benzo-thiazine-4-carbonitrile | 200 |

Notes:
[a]The aminocyanopyridine compound may be shown with a solvent, such as, for example, trifluoroacetate, with which it can form a salt. Both the salt and acid forms of the aminocyanopyridine compound are included in the present invention.
[b]Compound names generated by ACD/Name software.

In another embodiment, the present method can produce aminocyanopyridine compounds having the structure shown in formula I, where:

$R^1$ is selected from the group consisting of hydrogen, branched or unbranched alkyl, alkenyl, alkynyl, alkoxy, alkylaryl, arylalkyl, carboxy, carboxyalkyl, hydroxyalkyl, alkylcarboxy, aryl, amino, aminoalkyl, alkylamino, halo, alkylaminoalkyl, alkoxy, alkoxyalkyl, monocyclyl, bicyclyl, polycyclyl, and heterocyclyl;

$R^2$ is selected from the group consisting of hydrogen, alkyl, alkenyl, alkynyl, alkoxy, hydroxyalkyl, alkylaryl, arylalkyl, alkoxyaryl, aminoalkyl, alkylaminoalkyl, arylaminoalkyl, alkoxyalkyl, alkylcarboxy, and carboxyalkyl;

$R^3$ is selected from the group consisting of hydrogen, dicyanoalkyl, and substituted or unsubstituted heterocyclyl and cyclyl, where substituents, if any, comprise halo moieties;

$R^4$ is selected from the group consisting of hydrogen, dicyanoalkyl, and substituted or unsubstituted heterocyclyl and cyclyl, where substituents, if any, comprise halo moieties;

$R^5$ is selected from the group consisting of hydrogen, alkoxy, halo, alkyl, alkenyl, alkylyl, arylalkyl, or alkylaryl;

$R^6$ is selected from the group consisting of hydrogen, hydroxy, alkoxy, alkyl, alkenyl, alkynyl, amino, alkylamino, arylamino, alkylaminoalkyl, carboxy, aminoalkoxy, halo, alkylcarboxyalkyl, alkylamino, aminoalkyl, nitro, aryl, arylalkyl, alkylaryl, or arylamino;

$R^7$ is selected from the group consisting of hydrogen, hydroxy, alkoxy, alkenoxy, hydroxyalkoxy, alkoxyalkoxy, aminoalkoxy, heterocyclylalkyl, heterocyclylalkoxy, carboxyalkoxy, alkylaminoalkoxy, and alkylcarboxyalkoxy;

where the $R^6$ and $R^7$ groups can join to form a six membered heterocyclic ring;

$R^8$ is selected from the group consisting of hydrogen, hydroxy, halo, nitro, amino, alkyl, alkoxy, heterocyclylalkoxy, carboxyalkoxy, pyrrolidylethoxy, carboxymethoxy, hydroxyalkoxy, aminoalkoxy, alkylcarboxy, alkylaminoalkyl, carboxy, and heterocyclylalkyl; and G is selected from the group consisting of oxygen, sulfur, and nitrogen;

when G is oxygen, $R^9$ and $R^{10}$ are absent;

when G is sulfur, each of $R^9$ and $R^{10}$ is optionally absent or is oxo;

when G is nitrogen, $R^9$ is absent and $R^{10}$ is $C_1$–$C_4$-alkyl.

In another embodiment, the present method can be used to produce aminocyanopyridine compounds having the structure shown in formula I, where:

$R^1$ is selected from the group consisting of hydrogen, ethyl, dimethylaminoethyl, butyl, propyl, methoxyethyl, tetramethylaminoethyl, and carboxymethyl;

$R^2$ is selected from the group consisting of hydrogen, hydroxyethyl, propyl, ethyl, methyl, 4-methoxyphenyl, ethoxyethyl, aminoethyl, phenylmethyl, dimethylaminoethyl, phthaloaminoethyl, butyl, methoxyethyl, tetramethylaminoethyl, and carboxymethyl;

$R^3$ is selected from the group consisting of hydrogen, dicyanomethyl, 2-fluorophenyl, phenyl, and 3-fluorophenyl.

$R^4$ is selected from the group consisting of hydrogen, dicyanomethyl, 2-fluorophenyl, phenyl, and 3-fluorophenyl;

$R^5$ is selected from the group consisting of hydrogen, hydroxy, methoxy, bromo, and 2-pyridomethyl;

$R^6$ is selected from the group consisting of hydrogen, hydroxy, methoxy, amino, carboxy, diaminoethoxy, bromo, propoxy, isobutylcarboxymethoxy, dimethylamino, nitro, phenyl, chloro, pyridylmethyl, and fluoro;

$R^7$ is selected from the group consisting of hydrogen, hydroxy, methoxy, hydroxyethoxy, ethoxyethoxy, ethoxy, aminoethoxy, morpholinoethoxy, carboxymethoxy, N-pyrrolidylethoxy, dimethylaminoethoxy, pyridylmethyl, 2-propenoxy, and isobutylcarboxymethoxy, where the $R^6$ and $R^7$ groups can join to form a six membered heterocyclic ring;

$R^8$ is selected from the group consisting of hydrogen, hydroxy, fluoro, methoxy, nitro, amino, pyrrolidylethoxy, carboxymethoxy, methyl, hydroxyethoxy, aminoethoxy, 4-pyridylmethoxy, isobutyl, ethylcarboxy, dimethylaminoethoxy, carboxy, bromo, and pyrridylmethyl; and G is selected from the group consisting of oxygen, sulfur, and nitrogen;

when G is oxygen, $R^9$ and $R^{10}$ are absent;

when G is sulfur, each of $R^9$ and $R^{10}$ is optionally absent or is oxo;

when G is nitrogen, $R^9$ is absent and $R^{10}$ is —$CH_3$.

In another embodiment, the present method can be used to produce aminocyanopyridine compounds that have an $IC_{50}$ of less than about 200 µM, in an in vitro assay of MK-2 inhibitory activity. Examples of such compounds comprise the compound shown in formula I, where:

$R^1$ is selected from the group consisting of hydrogen, and $C_1$–$C_2$ alky;

$R^2$ is selected from the group consisting of hydrogen, $C_1$–$C_3$ alkyl, hydroxy $C_1$–$C_2$ alkyl, $C_1$–$C_2$ alkoxyphenyl, $C_1$–$C_2$ alkoxy $C_1$–$C_2$ alkyl, amino $C_1$–$C_2$ alkyl, phenyl $C_1$–$C_2$ alkyl, and di $C_1$–$C_2$ alkylamino $C_1$–$C_2$ alkyl;

$R^3$ and $R^4$ are each independently selected from the group consisting of hydrogen, dicyano $C_1$–$C_2$ alkyl, and halophenyl;

$R^5$ is selected from the group consisting of hydrogen, and hydroxy;

$R^6$ is selected from the group consisting of hydrogen, hydroxy, $C_1$–$C_3$ alkoxy, amino, nitro, carboxy, diamino $C_1$–$C_2$ alkoxy, halo, propenoxy, iso $C_3$–$C_4$ alkylcarboxy $C_1$–$C_2$ alkoxy, di $C_1$–$C_2$ alkylamino, and phenyl;

$R^7$ is selected from the group consisting of hydrogen, hydroxy, $C_1$–$C_3$ alkoxy, hydroxy $C_1$–$C_2$ alkoxy, $C_1$–$C_2$ alkoxy $C_1$–$C_2$ alkoxy, amino $C_1$–$C_2$ alkoxy, morpholino $C_1$–$C_2$ alkoxy, carboxyl $C_1$–$C_2$ alkoxy, pyrrolidyl $C_1$–$C_2$ alkoxy, di $C_1$–$C_2$ alkylamino $C_1$–$C_2$ alkoxy, pyrrolidyl $C_1$–$C_2$ alkyl, iso $C_3$–$C_4$ alkylcarboxy $C_1$–$C_2$ alkoxy, and $_2$-propenoxy, where the $R^6$ and $R^7$ groups can join to form a six membered heterocyclic ring;

$R^8$ is selected from the group consisting of hydrogen, hydroxy, halo, $C_1$–$C_2$ alkyl, $C_1$–$C_2$ alkoxy, nitro, amino, pyrrolidyl $C_1$–$C_2$ alkoxy, carboxy $C_1$–$C_2$ alkoxy, hydroxy $C_1$–$C_2$ alkoxy, and amino $C_1$–$C_2$ alkoxy; and G is selected from the group consisting of oxygen and sulfur;

when G is sulfur, each of $R^9$ and $R^{10}$ is optionally absent or is oxo;

when G is oxygen, $R^9$ and $R^{10}$ are absent.

In another embodiment, the present method can be used to produce aminocyanopyridine compounds that have an $IC_{50}$ of less than about 100 µM, in an in vitro assay of MK-2 inhibitory activity. Examples of such compounds comprise the compound shown in formula I, where:

$R^1$ is hydrogen;

$R^2$ is selected from the group consisting of hydrogen, $C_1$–$C_3$ alkyl, hydroxy $C_1$–$C_2$ alkyl, $C_1$–$C_2$ alkoxyphenyl, $C_1$–$C_2$ alkoxy $C_1$–$C_2$ alkyl, amino $C_1$–$C_2$ alkyl, phenyl $C_1$–$C_2$ alkyl, and di $C_1$–$C_2$ alkylamino $C_1$–$C_2$ alkyl;

$R^3$ and $R^4$ are each independently selected from the group consisting of hydrogen, and dicyano $C_1$–$C_2$ alkyl.

$R^5$ is selected from the group consisting of hydrogen, and hydroxy;

$R^6$ is selected from the group consisting of hydrogen, hydroxy, $C_1$–$C_2$ alkoxy, amino, carboxy, nitro, diamino $C_1$–$C_2$ alkoxy, halo, 2-propenoxy, iso $C_3$–$C_4$ alkylcarboxy $C_1$–$C_2$ alkoxy, di $C_1$–$C_2$ alkylamino, and phenyl;

$R^7$ is selected from the group consisting of hydrogen, hydroxy, $C_1$–$C_2$ alkoxy, hydroxy $C_1$–$C_2$ alkoxy, $C_1$–$C_2$ alkoxy $C_1$–$C_2$ alkoxy, amino $C_1$–$C_2$ alkoxy, morpholino $C_1$–$C_2$ alkoxy, carboxyl $C_1$–$C_2$ alkoxy, pyrrolidyl $C_1$–$C_2$ alkoxy, di $C_1$–$C_2$ alkylamino $C_1$–$C_2$ alkoxy, pyrrolidyl $C_1$–$C_2$ alkyl, iso $C_3$–$C_4$ alkylcarboxy $C_1$–$C_2$ alkoxy, and 2-propenoxy;

wherein the $R^6$ and $R^7$ groups can join to form a six membered heterocyclic ring;

$R^8$ is selected from the group consisting of hydrogen, hydroxy, halo, $C_1$–$C_2$ alkoxy, nitro, amino, pyrrolidyl $C_1$–$C_2$ alkoxy, and carboxy $C_1$–$C_2$ alkoxy; and G is selected from the group consisting of oxygen and sulfur;

when G is sulfur, each of $R^9$ and $R^{10}$ is optionally absent or is oxo;

when G is oxygen, $R^9$ and $R^{10}$ are absent.

In another embodiment, the present method can be used to produce aminocyanopyridine compounds having an $IC_{50}$ of less than about 50 µM, in an in vitro assay of MK-2 inhibitory activity. Examples of such compounds comprise the compound shown in formula I, where:

$R^1$ is hydrogen;

$R^2$ is selected from the group consisting of hydrogen, $C_1$–$C_3$ alkyl, hydroxy $C_1$–$C_2$ alkyl, $C_1$–$C_2$ alkoxyphenyl, $C_1$–$C_2$ alkoxy $C_1$–$C_2$ alkyl, amino $C_1$–$C_2$ alkyl, and phenyl $C_1$–$C_2$ alkyl;

$R^3$ and $R^4$ are each independently selected from the group consisting of hydrogen, and dicyano $C_1$–$C_2$ alkyl.

$R^5$ is selected from the group consisting of hydrogen, and hydroxy;

$R^6$ is selected from the group consisting of hydrogen, hydroxy, $C_1$–$C_2$ alkoxy, amino, carboxy, diamino $C_1$–$C_2$ alkoxy, halo, 2-propenoxy, iso $C_3$–$C_4$ alkylcarboxy $C_1$–$C_2$ alkoxy, and di $C_1$–$C_2$ alkylamino;

$R^7$ is selected from the group consisting of hydrogen, hydroxy, $C_1$–$C_2$ alkoxy, hydroxy $C_1$–$C_2$ alkoxy, $C_1$–$C_2$ alkoxy $C_1$–$C_2$ alkoxy, amino $C_1$–$C_2$ alkoxy, morpholino $C_1$–$C_2$ alkoxy, carboxyl $C_1$–$C_2$ alkoxy, pyrrolidyl $C_1$–$C_2$ alkoxy, di $C_1$–$C_2$ alkylamino $C_1$–$C_2$ alkoxy, pyrrolidyl $C_1$–$C_2$ alkyl, iso $C_3$–$C_4$ alkylcarboxy $C_1$–$C_2$ alkoxy, and 2-propenoxy;

where the $R^6$ and $R^7$ groups can join to form a six membered heterocyclic ring;

$R^8$ is selected from the group consisting of hydrogen, hydroxy, halo, $C_1$–$C_2$ alkoxy, nitro, amino, and pyrrolidyl $C_1$–$C_2$ alkoxy; and G is selected from the group consisting of oxygen and sulfur;

when G is sulfur, each of $R^9$ and $R^1$ is optionally absent or is oxo;

when G is oxygen, $R^9$ and $R^{10}$ are absent.

In another embodiment, the present method can be used to produce aminocyanopyridine compounds having an $IC_{50}$ of less than about 20 µM, in an in vitro assay of MK-2 inhibitory activity. Examples of such compounds comprise the compound shown in formula I, where:

$R^1$ is hydrogen;

$R^2$ is selected from the group consisting of hydrogen, $C_1$–$C_3$ alkyl, hydroxy $C_1$–$C_2$ alkyl, $C_1$–$C_2$ alkoxyphenyl, $C_1$–$C_2$ alkoxy $C_1$–$C_2$ alkyl, and amino $C_1$–$C_2$ alkyl;

$R^3$ and $R^4$ are each independently selected from the group consisting of hydrogen, and dicyanoethyl;

$R^5$ is selected from the group consisting of hydrogen, and hydroxy;

$R^6$ is selected from the group consisting of hydrogen, hydroxy, $C_1$–$C_2$ alkoxy, amino, carboxy, diamino $C_1$–$C_2$ alkoxy, halo, 2-propenoxy, iso $C_3$–$C_4$ alkylcarboxy $C_1$–$C_2$ alkoxy, and di $C_1$–$C_2$ alkylamino;

$R^7$ is selected from the group consisting of hydrogen, hydroxy, $C_1$–$C_2$ alkoxy, hydroxy $C_1$–$C_2$ alkoxy, $C_1$–$C_2$ alkoxy $C_1$–$C_2$ alkoxy, amino $C_1$–$C_2$ alkoxy, morpholino $C_1$–$C_2$ alkoxy, carboxyl $C_1$–$C_2$ alkoxy, pyrrolidyl $C_1$–$C_2$ alkoxy, di $C_1$–$C_2$ alkylamino $C_1$–$C_2$ alkoxy, pyrrolidyl $C_1$–$C_2$ alkyl, iso $C_3$–$C_4$ alkylcarboxy $C_1$–$C_2$ alkoxy, and 2-propenoxy;

where the $R^6$ and $R^7$ groups can join to form a six membered heterocyclic ring;

$R^8$ is selected from the group consisting of hydrogen, hydroxy, halo, methoxy, nitro, and amino; and G is selected from the group consisting of oxygen and sulfur when G is sulfur, each of $R^9$ and $R^{10}$ is optionally absent or is oxo;

when G is oxygen, $R^9$ and $R^{10}$ are absent.

Examples of aminocyanopyridine MK-2 inhibitor compounds that can be produced by the present invention include, without limitation, the following:

2,4-diamino-7,8-dihydroxy-5H-chromeno[2,3-b]pyridine-3-carbonitrile,
2,4-diamino-8-hydroxy-5H-chromeno[2,3-b]pyridine-3-carbonitrile,
2-amino-7,8-dihydroxy-4-[(2-hydroxyethyl)amino]-5H-chromeno[2,3-b]pyridine-3-carbonitrile,
2,4-diamino-7,8-dimethoxy-5H-chromeno[2,3-b]pyridine-3-carbonitrile,
2-amino-7,8-dihydroxy-4-(propylamino)-5H-chromeno[2,3-b]pyridine-3-carbonitrile,
2-amino-4-(ethylamino)-7,8-dihydroxy-5H-chromeno[2,3-b]pyridine-3-carbonitrile,
2,4-diamino-9-hydroxy-5H-chromeno[2,3-b]pyridine-3-carbonitrile,
2,4-diamino-9-fluoro-5H-chromeno[2,3-b]pyridine-3-carbonitrile,
2,4-diamino-7-hydroxy-5H-chromeno[2,3-b]pyridine-3-carbonitrile,
2,4-diamino-8-(2-hydroxyethoxy)-5H-chromeno[2,3-b]pyridine-3-carbonitrile,
8,10-diamino-2,3-dihydro-11H-[1,4]dioxino[2',3':6,7]chromeno[2,3-b]pyridine-9-carbonitrile,
2,4,7-triamino-5H-chromeno[2,3-b]pyridine-3-carbonitrile
2,4-diamino-5H-chromeno[2,3-b]pyridine-3-carbonitrile,
2,4-diamino-8-(2-ethoxyethoxy)-7-hydroxy-5H-chromeno[2,3-b]pyridine-3-carbonitrile,
2,4-diamino-9-hydroxy-8-methoxy-5H-chromeno[2,3-b]pyridine-3-carbonitrile,
2,4-diamino-6,8-dihydroxy-5H-chromeno[2,3-b]pyridine-3-carbonitrile,
2,4-diamino-8-ethoxy-7-hydroxy-5H-chromeno[2,3-b]pyridine-3-carbonitrile,
2,4-diamino-8-(2-ethoxyethoxy)-5H-chromeno[2,3-b]pyridine-3-carbonitrile,
2,4-diamino-8-(2-aminoethoxy)-5H-chromeno[2,3-b]pyridine-3-carbonitrile,
2,4-diamino-3-cyano-5H-chromeno[2,3-b]pyridine-7-carboxylic acid,
2,4-diamino-8,9-dihydroxy-5H-chromeno[2,3-b]pyridine-3-carbonitrile,
2,4-diamino-8-(2-morpholin-4-ylethoxy)-5H-chromeno[2,3-b]pyridine-3-carbonitrile,
[(2,4-diamino-3-cyano-5H-chromeno[2,3-b]pyridin-8-yl)oxy]acetic acid,
2,4-diamino-9-methoxy-5H-chromeno[2,3-b]pyridine-3-carbonitrile,
2,4-diamino-8-(2-pyrrolidin-1-ylethoxy)-5H-chromeno[2,3-b]pyridine-3-carbonitrile,
2-amino-7,8-dimethoxy-4-(methylamino)-5H-chromeno[2,3-b]pyridine-3-carbonitrile,
2,4-diamino-8-methoxy-5H-chromeno[2,3-b]pyridine-3-carbonitrile,
2,4-diamino-8-[2-(dimethylamino)ethoxy]-5H-chromeno[2,3-b]pyridine-3-carbonitrile,
2,4,7-triamino-9-methoxy-5H-chromeno[2,3-b]pyridine-3-carbonitrile,
2(2,4-diamino-3-cyano-8-methoxy-5H-chromeno[2,3-b]pyridin-5-yl)malononitrile,
2,4-diamino-7,8-di[2-(amino)ethoxy]-5H-chromeno[2,3-b]pyridine-3-carbonitrile,
2,4-diamino-9-nitro-5H-chromeno[2,3-b]pyridine-3-carbonitrile,
2-amino-7,8-dimethoxy-4-[(4-methoxyphenyl)amino]-5H-chromeno[2,3-b]pyridine-3-carbonitrile,
2,4-diamino-8-methoxy-5H-chromeno[2,3-b]pyridine-3-carbonitrile,
2(2,4-diamino-3-cyano-7-hydroxy-5H-chromeno[2,3-b]pyridin-5-yl)malononitrile,
2(2,4-diamino-3-cyano-7-bromo-5H-chromeno[2,3-b]pyridin-5-yl)malononitrile,
2-amino-8-ethoxy-4-(ethylamino)-5H-chromeno[2,3-b]pyridine-3-carbonitrile,
2,4,9-triamino-5H-chromeno[2,3-b]pyridine-3-carbonitrile,
2,4,7-triamino-5H-thiochromeno[2,3-b]pyridine-3-carbonitrile,
2-amino-7,8-dimethoxy-4-[(4-methoxyphenyl)amino]-5H-chromeno[2,3-b]pyridine-3-carbonitrile,
2(2,4-diamino-3-cyano-7-methoxy-5H-chromeno[2,3-b]pyridin-5-yl)malononitrile,
2,4-diamino-9-hydroxy-8-(piperidin-1-ylmethyl)-5H-chromeno[2,3-b]pyridine-3-carbonitrile,
7,8-bis(allyloxy)-2,4-diamino-5H-chromeno[2,3-b]pyridine-3-carbonitrile,
2-amino-8-(2-ethoxyethoxy)-4-[(2-ethoxyethyl)amino]-5H-chromeno[2,3-b]pyridine-3-carbonitrile,
tert-butyl {[2,4-diamino-7-(2-tert-butoxy-2-oxoethoxy)-3-cyano-5H-chromeno[2,3-b]pyridin-8-yl]oxy}acetate,
2-amino-4-[(2-aminoethyl)amino]-7,8-dimethoxy-5H-chromeno[2,3-b]pyridine-3-carbonitrile,
2(2,4-diamino-3-cyano-8-hydroxy-5H-chromeno[2,3-b]pyridin-5-yl)malononitrile,
2,4,7-triamino-5H-thiochromeno[2,3-b]pyridine-3-carbonitrile 10,10-dioxide,
2,4-diamino-7-bromo-5H-chromeno[2,3-b]pyridine-3-carbonitrile,
2-amino-7,8-dimethoxy-4-(propylamino)-5H-chromeno[2,3-b]pyridine-3-carbonitrile,
2,4-diamino-7-hydroxy-5H-thiochromeno[2,3-b]pyridine-3-carbonitrile,
2,4-diamino-7-(dimethylamino)-5H-chromeno[2,3-b]pyridine-3-carbonitrile,
2,4-diamino-7-methoxy-5H-chromeno[2,3-b]pyridine-3-carbonitrile,
2(2,4-diamino-3-cyano-9-methoxy-5H-chromeno[2,3-b]pyridin-5-yl)malononitrile,
2-amino-4-(benzylamino)-7,8-dimethoxy-5H-chromeno[2,3-b]pyridine-3-carbonitrile, 8-(allyloxy)-2,4-diamino-5H-chromeno[2,3-b]pyridine-3-carbonitrile,
2,4-diamino-9-fluoro-5H-thiochromeno[2,3-b]pyridine-3-carbonitrile,
2,4-diamino-7-methoxy-5H-chromeno[2,3-b]pyridine-3-carbonitrile,
2,4-diamino-9-(2-pyrrolidin-1-ylethoxy)-5H-chromeno[2,3-b]pyridine-3-carbonitrile,
2,4-diamino-7-nitro-5H-chromeno[2,3-b]pyridine-3-carbonitrile,
2,4-diamino-10-methyl-5,10-dihydrobenzo[b]-1,8-naphthyridine-3-carbonitrile,
[(2,4-diamino-3-cyano-5H-chromeno[2,3-b]pyridin-9-yl)oxy]acetic acid,
2-amino-4-{[2-(dimethylamino)ethyl]amino}-7,8-dimethoxy-5H-chromeno[2,3-b]pyridine-3-carbonitrile,
2,4-diamino-7-nitro-5H-thiochromeno[2,3-b]pyridine-3-carbonitrile 10,10-dioxide,
2,4-diamino-7-phenyl-5H-chromeno[2,3-b]pyridine-3-carbonitrile,
2,4-diamino-7-chloro-9-methyl-5H-chromeno[2,3-b]pyridine-3-carbonitrile,
2,4-diamino-7-fluoro-5H-thiochromeno[2,3-b]pyridine-3-carbonitrile 10,10-dioxide,
8-ethoxy-2,4-bis(ethylamino)-5H-chromeno[2,3-b]pyridine-3-carbonitrile,
2,4-diamino-5-(2-fluoro-phenyl)-8-methoxy-5H-chromeno[2,3-b]pyridine-3-carbonitrile,
2,4-diamino-9-(2-hydroxyethoxy)-5H-chromeno[2,3-b]pyridine-3-carbonitrile,
2,4-diamino-9-(2-aminoethoxy)-5H-chromeno[2,3-b]pyridine-3-carbonitrile,
2(2,4-diamino-3-cyano-7-chloro-5H-chromeno[2,3-b]pyridin-5-yl)malononitrile,
2,4-bis{[2-(dimethylamino)ethyl]amino}-7,8-dimethoxy-5H-chromeno[2,3-b]pyridine-3-carbonitrile,
2-amino-4-{[2-(1,3-dioxo-1,3-dihydro-2H-isoindol-2-yl)ethyl]amino}-7,8-dimethoxy-5H-chromeno[2,3-b]pyridine-3-carbonitrile,
2,4-diamino-7-fluoro-5H-chromeno[2,3-b]pyridine-3-carbonitrile,
2,4-diamino-7-bromo-5H-chromeno[2,3-b]pyridine-3-carbonitrile,
2,4-diamino-9-(pyridin-4-ylmethoxy)-5H-chromeno[2,3-b]pyridine-3-carbonitrile,
2,4-diamino-7-chloro-5H-chromeno[2,3-b]pyridine-3-carbonitrile,
2,4-diamino-9-tert-butyl-5H-chromeno[2,3-b]pyridine-3-carbonitrile,
ethyl 2,4-diamino-3-cyano-5H-chromeno[2,3-b]pyridine-9-carboxylate,
2,4-diamino-9-[2-(dimethylamino)ethoxy]-5H-chromeno[2,3-b]pyridine-3-carbonitrile,
2,4-bis(butylamino)-7,8-dimethoxy-5H-chromeno[2,3-b]pyridine-3-carbonitrile,
2-amino-4-(butylamino)-7,8-dimethoxy-5H-chromeno[2,3-b]pyridine-3-carbonitrile,
7,8-dimethoxy-2,4-bis(propylamino)-5H-chromeno[2,3-b]pyridine-3-carbonitrile,
2,4-bis(ethylamino)-7,8-dimethoxy-5H-chromeno[2,3-b]pyridine-3-carbonitrile,
2-amino-4-(ethylamino)-7,8-dimethoxy-5H-chromeno[2,3-b]pyridine-3-carbonitrile,
2,4-diamino-6,8-dimethoxy-5H-chromeno[2,3-b]pyridine-3-carbonitrile,
2,4-diamino-7-(trifluoromethoxy)-5H-chromeno[2,3-b]pyridine-3-carbonitrile,
2,4-diamino-7-bromo-9-methoxy-5H-chromeno[2,3-b]pyridine-3-carbonitrile,
2,4-diamino-9-methoxy-7-nitro-5H-chromeno[2,3-b]pyridine-3-carbonitrile,
7,9-diamino-10H-[1,3]dioxolo[6,7]chromeno[2,3-b]pyridine-8-carbonitrile,
7,9-diamino-10H-[1,3]dioxolo[6,7]chromeno[2,3-b]pyridine-8-carbonitrile,
2,4-diamino-8-methyl-5H-chromeno[2,3-b]pyridine-3-carbonitrile,
7,8-dimethoxy-2,4-bis[(2-methoxyethyl)amino]-5H-chromeno[2,3-b]pyridine-3-carbonitrile,
2-amino-7,8-dimethoxy-4-[(2-methoxyethyl)amino]-5H-chromeno[2,3-b]pyridine-3-carbonitrile,
2-amino-7,8-dimethoxy-4-[(2-pyrrolidin-1-ylethyl)amino]-5H-chromeno[2,3-b]pyridine-3-carbonitrile,
7,8-dimethoxy-2,4-bis[(2-pyrrolidin-1-ylethyl)amino]-5H-chromeno[2,3-b]pyridine-3-carbonitrile,
2,4-bis(glycinyl)-7,8-dimethoxy-5H-chromeno[2,3-b]pyridine-3-carbonitrile,
N-(2-amino-3-cyano-7,8-dimethoxy-5H-chromeno[2,3-b]pyridin-4-yl)glycine,
2,4-diamino-3-cyano-5H-chromeno[2,3-b]pyridine-9-carboxylic acid,
2,4-diamino-6-methoxy-5H-chromeno[2,3-b]pyridine-3-carbonitrile,
2,4-diamino-9-bromo-7-chloro-5H-chromeno[2,3-b]pyridine-3-carbonitrile,
2,4-bis(ethylamino)-7,8-dihydroxy-5H-chromeno[2,3-b]pyridine-3-carbonitrile,
2,4-diamino-6-bromo-9-methoxy-5H-chromeno[2,3-b]pyridine-3-carbonitrile,
2,4-diamino-8-hydroxy-7,9-bis(piperidin-1-ylmethyl)-5H-chromeno[2,3-b]pyridine-3-carbonitrile,
2,4-diamino-5-phenyl-8-hydroxy-5H-chromeno[2,3-b]pyridine-3-carbonitrile,
2,4-diamino-5-(3-fluoro-phenyl)-8-methoxy-5H-chromeno[2,3-b]pyridine-3-carbonitrile,
2,4-diamino-9-hydroxy-6,8-bis(piperidin-1-ylmethyl)-5H-chromeno[2,3-b]pyridine-3-carbonitrile,
2,4-diamino-7-bromo-8-methoxy-5H-chromeno[2,3-b]pyridine-3-carbonitrile,
2,4-diamino-5-phenyl-8-methoxy-5H-chromeno[2,3-b]pyridine-3-carbonitrile,
2,4-diamino-9-fluoro-5H-thiochromeno[2,3-b]pyridine-3-carbonitrile 10,10-dioxide,
2,4-diamino-7-nitro-5H-thiochromeno[2,3-b]pyridine-3-carbonitrile,
2,4-diamino-7-methoxy-5H-thiochromeno[2,3-b]pyridine-3-carbonitrile 10,10-dioxide, 2,4-diamino-7-methoxy-5H-thiochromeno[2,3-b]pyridine-3-carbonitrile,
2,4-diamino-5H-thiochromeno[2,3-b]pyridine-3-carbonitrile 10,10-dioxide,
2,4-diamino-5H-thiochromeno[2,3-b]pyridine-3-carbonitrile,
2,4-diamino-7-fluoro-5H-thiochromeno[2,3-b]pyridine-3-carbonitrile,
2-amino-7,9-dimethyl-5-oxo-5H-chromeno[2,3-b]pyridine-3-carbonitrile,
2-amino-7-isopropyl-5-oxo-5H-chromeno[2,3-b]pyridine-3-carbonitrile,
2-amino-7-ethyl-5-oxo-5H-chromeno[2,3-b]pyridine-3-carbonitrile,
2-amino-7-methyl-5-oxo-5H-chromeno[2,3-b]pyridine-3-carbonitrile,
2-amino-7-chloro-5-oxo-5H-chromeno[2,3-b]pyridine-3-carbonitrile, 2-amino-7-bromo-5-oxo-5H-chromeno[2,3-b]pyridine-3-carbonitrile, 2-amino-5-oxo-5H-chromeno[2,3-b]pyridine-3-carbonitrile, and 3-amino-5H-pyrido[3,4-b][1,4]benzothiazine-4-carbonitrile.

It should be understood that salts and prodrugs of the aminocyanopyridine compounds that are described herein, as well as isomeric forms, tautomers, racemic mixtures of the compounds, and the like, which have the same or similar activity as the compounds that are described, are to be considered to be included within the description of the compound.

Aminocyanopyridine MK-2 inhibiting compounds of the type shown in formula I, above, include tricyclic aminocyanopyridine MK-2 inhibiting compounds, such as benzonapthyridines, pyridochromanes, and pyridothiochromanes. A general method for the synthesis of these tricyclic aminocyanopyridines is shown in Scheme 1, below:

Scheme 1:

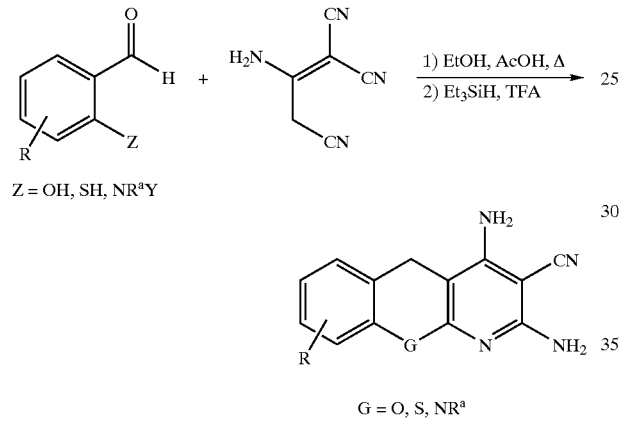

G = O, S, NR$^a$

In this method, a substituted benzaldehyde is reacted with a tricarbonitrile, preferably 2-amino-1-propene-1,1,3-tricarbonitrile. The reaction can be carried out by heating the reactants to reflux in a solution of acetic acid and ethanol. The reaction product can be concentrated in vacuo and dissolved in trifluoroacetic acid. Triethylsilane is added and the mixture is stirred. In a preferred method, the mixture is stirred for about 1 hour at 0° C. Dichloromethane is then added and solids are collected. The solids can be collected by filtration, and can be washed with dichloromethane and ether. The solids comprise the desired tricyclic aminocyanopiyridine MK-2 inhibiting compound of the type including benzonapthyridines, pyridochromanes, and pyridothiochromanes.

Referring to the reactants and products shown above in Scheme I:
Z can be OH, SH, or NR$^a$Y, where Y is a protecting group for nitrogen. The Y group can be benzyl, allyl, an alkyl carbamate, or a benzyl carbamate. Other nitrogen protecting groups are know to persons having skill in the art of organic synthesis. A perferred protecting group is tert-butylcarbamate. R$^a$ can be an alkyl group, an aryl group, or a heteroaryl group. The benzene ring of the benzaldehyde can be further substituted by one, two, three, or four additional R groups at carbons 3, 4, 5, or 6. Each R can independently be hydrogen; alkyl; aryl; a heteroatom, such as O, N, or S, substituted with hydrogen, C$_1$–C$_6$ alkyl, C$_1$–C$_6$ branched alkyl, aryl, heteroaryl (wherein the heteroaryl can include, but is not limited to, pyrazolyl, inidizolyl, pyrryl, pyridyl, thiophyl, furyl and pyrimidyl), ester and amido.

Advantages of this method include that it is a general method that can be used to produce various types of the tricyclic compounds of formula I depending upon the types of reactants used. It is also an easy and straightforward synthesis method that can be carried out in a single vessel.

In an embodiment of this method of synthesis as described above, a tricyclic aminocyanopyridine MK-2 inhibiting compound can be prepared by reacting a substituted benzaldehyde having the structure:

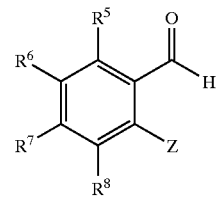

with a tricarbonitrile having the structure:

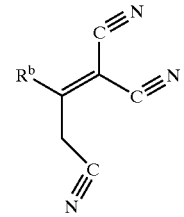

to form an aminocyanopyridine compound having the structure:

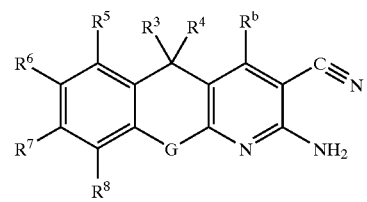

wherein:
Z is selected from the group consisting of —OH, —SH, and —NR$^a$Y;
R$^a$ is selected from the group consisting of alkyl, aryl, and heteroaryl;
Y is a protecting group for nitrogen. Examples of such nitrogen protecting groups include benzyl, allyl, alkyl carbamates and benzyl carbamates.
G is selected from the group consisting of oxygen, sulfur, and nitrogen;
when G is oxygen, it has no substituent groups;
when G is sulfur, it is either unsubstituted, or is substituted with one or two oxo groups;
when G is nitrogen, it is substituted with C$_1$–C$_4$ alkyl;
R$^b$ is selected from the group consisting of furyl and —NH—R$^2$;
R$^2$ is selected from the group consisting of hydrogen, alkyl, alkenyl, alkynyl, alkoxy, hydroxyalkyl, alkylaryl, arylalkyl, alkoxyaryl, aminoalkyl, alkylaminoalkyl, arylaminoalkyl, alkoxyalkyl, alkylcarboxy, and carboxyalkyl;

$R^3$ and $R^4$ are each independently selected from the group consisting of hydrogen, dicyanoalkyl, and substituted or unsubstituted heterocyclyl and cyclyl, where substituents, if any, comprise halo moieties; and $R^5$, $R^6$, $R^7$ and $R^8$ are each independently selected from the group consisting of hydrogen, hydroxy, alkoxy, halo, alkyl, alkenyl, alkylyl, arylalkyl, alkylaryl, amino, alkylamino, arylamino, alkylaminoalkyl, carboxy, aminoalkoxy, alkylcarboxyalkyl, alkylamino, aminoalkyl, nitro, aryl, arylamino, alkenoxy, hydroxyalkoxy, alkoxyalkoxy, heterocyclylalkyl, heterocyclylalkoxy, carboxyalkoxy, alkylaminoalkoxy, alkylcarboxyalkoxy, pyrrolidylethoxy, hydroxyalkoxy, and alkylcarboxy, where $R^6$ and $R^7$ are such that they optionally join to form a six membered heterocyclic ring.

In an embodiment of the general method described above, $R^2$ is selected from the group consisting of hydrogen, alkyl, alkenyl, alkynyl, alkoxy, hydroxyalkyl, alkylaryl, arylalkyl, alkoxyaryl, aminoalkyl, alkylaminoalkyl, arylaminoalkyl, alkoxyalkyl, alkylcarboxy, and carboxyalkyl;

$R^3$ and $R^4$ are each independently selected from the group consisting of hydrogen, dicyanoalkyl, and substituted or unsubstituted heterocyclyl and cyclyl, where substituents, if any, comprise halo moieties;

$R^5$ is selected from the group consisting of hydrogen, alkoxy, halo, alkyl, alkenyl, alkylyl, arylalkyl, or alkylaryl;

$R^6$ is selected from the group consisting of hydrogen, hydroxy, alkoxy, alkyl, alkenyl, alkynyl, amino, alkylamino, arylamino, alkylaminoalkyl, carboxy, aminoalkoxy, halo, alkylcarboxyalkyl, alkylamino, aminoalkyl, nitro, aryl, arylalkyl, alkylaryl, or arylamino;

$R^7$ is selected from the group consisting of hydrogen, hydroxy, alkoxy, alkenoxy, hydroxyalkoxy, alkoxyalkoxy, aminoalkoxy, heterocyclylalkyl, heterocyclylalkoxy, carboxyalkoxy, alkylaminoalkoxy, and alkylcarboxyalkoxy;

where the $R^6$ and $R^7$ groups can join to form a six membered heterocyclic ring; and $R^8$ is selected from the group consisting of hydrogen, hydroxy, halo, nitro, amino, alkyl, alkoxy, heterocyclylalkoxy, carboxyalkoxy, pyrrolidylethoxy, carboxymethoxy, hydroxyalkoxy, aminoalkoxy, alkylcarboxy, alkylaminoalkyl, carboxy, and heterocyclylalkyl.

In a preferred embodiment of this method, the substituted benzaldehyde comprises salicaldehyde and the tricarbonitrile comprises 2-amino-1-propene-1,1,3-tricarbonitrile. It is also preferred that the nitrogen protecting group "Y", comprises tert-butylcarbamate.

In an embodiment of the present method,

Z is selected from the group consisting of —OH, —SH, and —NR$^a$Y;

R$^a$ is selected from the group consisting of alkyl, aryl, and heteroaryl;

Y is a protecting group for nitrogen that is selected from the group consisting of benzyl, allyl, alkyl carbamates and benzyl carbamate;

G is selected from the group consisting of oxygen, sulfur, and nitrogen;

when G is oxygen, it has no substituent groups;

when G is sulfur, it is either unsubstituted, or is substituted with one or two oxo groups;

when G is nitrogen, it is substituted with $C_1$–$C_4$ alkyl;

$R^b$ is selected from the group consisting of furyl and —NH—$R^2$;

$R^2$ is selected from the group consisting of hydrogen, alkyl, alkenyl, alkynyl, alkoxy, hydroxyalkyl, alkylaryl, arylalkyl, alkoxyaryl, aminoalkyl, alkylaminoalkyl, arylaminoalkyl, alkoxyalkyl, alkylcarboxy, and carboxyalkyl;

$R^3$ and $R^4$ are each independently selected from the group consisting of hydrogen, dicyanoalkyl, and substituted or unsubstituted heterocyclyl and cyclyl, where substituents, if any, comprise halo moieties; and $R^5$, $R^6$, $R^7$ and $R^8$ are each independently selected from the group consisting of:

hydrogen, hydroxy, amino, halo, nitro, branched or unbranched $C_1$–$C_6$ alkyl, $C_2$–$C_6$ alkenyl, $C_2$–$C_6$ alkynyl, $C_1$–$C_6$ alkoxy, hydroxy $C_1$–$C_6$ alkyl, hydroxy $C_1$–$C_6$ alkoxy, $C_1$–$C_6$ alkoxy $C_1$–$C_6$ alkoxy, $C_1$–$C_6$ alkoxy $C_1$–$C_6$ alkyl, $C_2$–$C_6$ alkenoxy, branched or unbranched amino $C_1$–$C_6$ alkyl, diamino $C_2$–$C_6$ alkyl, $C_1$–$C_6$ alkylamino $C_1$–$C_6$ alkyl, $C_1$–$C_6$ alkylamino, di-($C_1$–$C_6$ alkyl)amino, $C_1$–$C_4$ alkoxyarylamino, $C_1$–$C_4$ alkoxyalkylamino, amino $C_1$–$C_6$ alkoxy, di-($C_1$–$C_4$ alkylamino, $C_2$–$C_6$ alkoxy, di-($C_1$–$C_6$alkyl)amino $C_1$–$C_6$alkyl, $C_1$–$C_6$ alkylamino $C_1$–$C_6$ alkoxy, halo $C_1$–$C_6$alkoxy, dihalo $C_1$–$C_6$alkoxy, trihalo $C_1$–$C_6$ alkoxy, cyano $C_1$–$C_6$ alkyl, dicyano $C_1$–$C_6$ alkyl, cyano $C_1$–$C_6$ alkoxy, dicyano $C_1$–$C_6$ alkoxy, carbamyl $C_1$–$C_4$ alkoxy, heterocyclyl $C_1$–$C_4$ alkoxy, heteroaryl $C_1$–$C_4$ alkoxy, sulfo, sulfamyl, $C_1$–$C_4$ alkylaminosulfonyl, hydroxy $C_1$–$C_4$ alkylaminosulfonyl, di-($C_1$–$C_4$ alkyl)aminosulfonyl, $C_1$–$C_4$ alkylthio, $C_1$–$C_4$ alkylsulfonyl, $C_1$–$C_4$ alkylsulfinyl, aryl, aryl $C_1$–$C_6$ alkyl, heterocyclyl $C_1$–$C_6$ alkyl, heteroaryl $C_1$–$C_6$ alkyl, heterocyclyl $C_1$–$C_6$ alkoxy, heteroaryl $C_1$–$C_6$ alkoxy, aryl $C_1$–$C_6$ alkoxy, where the aryl ring can be substituted or unsubstituted, and, if substituted, the substituent group is selected from one or more of the group consisting of $C_1$–$C_6$ alkyl, halo, amino, and $C_1$–$C_6$ alkoxy, substituted or unsubstituted $C_3$–$C_6$ cyclyl, $C_3$–$C_6$ heterocyclyl, and, if substituted, the substituent group is selected from one or more of the group consisting of $C_1$–$C_6$ alkyl, $C_1$–$C_6$ alkoxy, halo, amino, and where the $C_3$–$C_6$ heterocyclyl ring contains O, S, or N, branched or unbranched $C_1$–$C_6$ alkoxycarbonyl $C_1$–$C_6$ alkoxy, and carboxy, carboxy $C_1$–$C_6$ alkoxy, carboxy $C_1$–$C_6$ alkyl, hydroxy $C_1$–$C_4$ alkoxycarbonyl, $C_1$–$C_4$ alkoxycarbonyl.

And where the terms "alkyl, alkenyl, alkynyl, alkoxy, alkoxyalkyl, haloalkoxy, halo, alkylthio, alkylthioalkyl, heterocyclyl, cyclyl, aryl, heteroaryl, cycloaryl, and oxo" have the same meanings as described above.

Further details of the synthesis of aminocyanopyridines are provided in the examples.

The MK-2 inhibiting activity of an aminocyanopyridine compound can be determined by any one of several methods that-are well known to those having skill in the art of enzyme activity testing. One such method is described in detail in the general methods section of the examples. In addition, the efficacy of an aminocyanopyridine MK-2 inhibiting compound in therapeutic applications can be determined by testing for inhibition of TNFα production in cell culture and in animal model assays. In general, it is preferred that the aminocyanopyridine MK-2 inhibiting compounds of the present invention be capable of inhibiting the production and/or the release of TNFα in cell cultures and in animal models.

It should be recognized that the isomeric forms and tautomers and the pharmaceutically-acceptable salts of the aminocyanopyridine MK-2 inhibitors that are produced by the present method can be easily produced by simple additional reactions. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, β-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric and galacturonic acids.

Suitable pharmaceutically-acceptable base addition salts that can be used with the compounds produced by the present invention include metallic ion salts and organic ion salts. More preferred metallic ion salts include, but are not limited to, appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trifluoroacetate, trimethylamine, diethylamine, N,N-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

The tricyclic aminocyanopyridine compounds that can be produced by the present invention are useful for, but not limited to, the prevention and treatment of diseases and disorders that are mediated by TNFα. For example, the aminocyanopyridine MK-2 inhibitors of the invention would be useful to treat arthritis, including, but not limited to, rheumatoid arthritis, spondyloarthopathies, gouty arthritis, osteoarthritis, systemic lupus erythematosus and juvenile arthritis. Such aminocyanopyridine MK-2 inhibitor compounds of the invention would be useful in the treatment of asthma, bronchitis, menstrual cramps, tendinitis, bursitis, connective tissue injuries or disorders, and skin related conditions such as psoriasis, eczema, burns and dermatitis.

The tricyclic aminocyanopyridine MK-2 inhibitor compounds that can be produced by the present method also would be useful to treat gastrointestinal conditions such as inflammatory bowel disease, gastric ulcer, gastric varices, Crohn's disease, gastritis, irritable bowel syndrome and ulcerative colitis and for the prevention or treatment of cancer, such as colorectal cancer. Such aminocyanopyridine MK-2 inhibiting compounds would be useful in treating inflammation in diseases and conditions such as herpes simplex infections, HIV, pulmonary edema, kidney stones, minor injuries, wound healing, vaginitis, candidiasis, lumbar spondylanhrosis, lumbar spondylarthrosis, vascular diseases, migraine headaches, sinus headaches, tension headaches, dental pain, periarteritis nodosa, thyroiditis, aplastic anemia, Hodgkin's disease, sclerodoma, rheumatic fever, type I diabetes, myasthenia gravis, multiple sclerosis, sarcoidosis, nephrotic syndrome, Behcet's syndrome, polymyositis, gingivitis, hypersensitivity, swelling occurring after injury, myocardial ischemia, and the like.

The tricyclic aminocyanopyridine MK-2 inhibitors would also be useful in the treatment of ophthalmic diseases, such as retinitis, retinopathies, conjunctivitis, uveitis, ocular photophobia, and of acute injury to the eye tissue. These compounds would also be useful in the treatment of pulmonary inflammation, such as that associated with viral infections and cystic fibrosis. The compounds would also be useful for the treatment of certain central nervous system disorders such as cortical dementias including Alzheimer's disease.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples all percentages are given on a weight basis unless otherwise indicated.

General Information for Preparation Methods

Unless otherwise noted, reagents and solvents were used as received from commercial suppliers.

NMR Analysis:

Proton nuclear magnetic resonance spectra were obtained on a Varian Unity Innova 400, a Varian Unity Innova 300 a Varian Unity 300, a Bruker AMX 500 or a Bruker AV-300 spectrometer. Chemical shifts are given in ppm (δ) and coupling constants, J, are reported in Hertz. Tetramethylsilane was used as an internal standard for proton spectra and the solvent peak was used as the reference peak for carbon spectra. Mass spectra were obtained on a Perkin Elmer Sciex 100 atmospheric pressure ionization (APCI) mass spectrometer, a Finnigan LCQ Duo LCMS ion trap electrospray ionization (ESI) mass spectrometer, a PerSeptive Biosystems Mariner TOF HPLC-MS (ESI), or a Waters ZQ mass spectrometer (ESI).

Determination of MK-2 $IC_{50}$:

Recombinant MAPKAPK2 was phosphorylated at a concentration of 42–78 μM by incubation with 0.23 μM of active p38α in 50 mM HEPES, 0.1 mM EDTA, 10 mM magnesium acetate, and 0.25 mM ATP, pH 7.5 for one hour at 30° C.

The phosphorylation of HSP-peptide (KKKALSRQLSVAA) by MAPKAPK2 was measured using an anion exchange resin capture assay method. The reaction was carried out in 50 mM β-glycerolphosphate, 0.04% BSA, 10 mM magnesium acetate, 2% DMSO and 0.8 mM dithiotheritol, pH 7.5 in the presence of the HSP-peptide with 0.2 μCi [$\gamma^{33}$P]ATP and 0.03 mM ATP. The reaction was initiated by the addition of 15 nM MAPKAPK2 and was allowed to incubate at 30° C. for 30 min. The reaction was terminated and [$\gamma^{33}$PP]ATP was removed from solution by the addition of 150 μl of AG 1×8 ion exchange resin in 900 mM sodium formate pH 3.0. A 50 μl aliquot of head volume was removed from the quenched reaction mixture and added to a 96-well plate, 150 μl of Microscint-40 (Packard) was added and the amount of phosphorylated-peptide was determined. Allow the Microscint to sit in the plates for 60 minutes prior to counting.

Compounds are evaluated as potential inhibitors of the MK2 kinase by measuring their effects on MK2 phosphorylation of the peptide substrate. Compounds may be screened initially at two concentrations prior to determination of $IC_{50}$ values. Screening results are expressed as percent inhibition at the concentrations of compound tested. For $IC_{50}$ value determinations, compounds are tested at six concentrations in ten-fold serial dilutions with each concentration tested in triplicate. Results are expressed as $IC_{50}$ values in micromolar. The assay is performed at a final concentration of 2% DMSO.

Preferred aminocyanopyridine MK-2 inhibiting compounds of the present invention provide $IC_{50}$ values for MK-2 inhibition of below 200 $\mu$M. One method that can be used for determining the MK-2 inhibition $IC_{50}$ value is that described just above. More preferred aminocyanopyridine MK-2 inhibiting compounds have the capability of providing MK-2 inhibition $IC_{50}$ values of below 100 $\mu$M, yet more preferred of below 50 $\mu$M, even more preferred of below 20 $\mu$M, yet more preferred of below 10 $\mu$M, and even more preferred of below 1 $\mu$M.

U937 Cell TNFα Release Assay

The human monocyte-like cell line, U937 (ATCC #CRL-1593.2), is cultured in RPMI1640 media with 10% heat-inactivated fetal calf serum (GIBCO), glutamine and pen/strep at 37° C. and 5% $CO_2$. Differentiation of U937 to monocytic/macrophage-like cells is induced by the addition of phorbol12-myristate 13-acetate (Sigma) at final concentration of 20 ng/ml to a culture of U937 cells at ~0.5 million cells/ml and incubated for 24 hrs. The cells are centrifuged, washed with PBS and resuspended in fresh media without PMA and incubated for 24 hrs. Cells adherent to the culture flask are harvested by scraping, centrifugation, and resuspended in fresh media to 2 million cells/ml, and 0.2 ml is aliquoted to each of 96 wells in flat-bottom plate. Cells are then incubated for an additional 24 hrs to allow for recovery. The media is removed from the cells, and 0.1 ml of fresh media is added per well. 0.05 ml of serially diluted compound or control vehicle (Media with DMSO) is added to the cells. The final DMSO concentration does not exceed 1%. After 1 hr incubation, 0.05 ml of 400 ng/ml LPS (*E Coli* serotype 0111:B4, Sigma) in media is added for final concentration of 100 ng/ml. Cells are incubated at 37° C. for 4 hrs. After 4 hrs incubation, supernatants are harvest and assayed by ELISA for the presence of TNFα.

U937 cell TNFα ELISA

ELISA plates (NUNC-Immuno™ Plate Maxisorb™ Surface) were coated with purified mouse monoclonal IgG1 anti-human TNFα antibody (R&D Systems #MAB610; 1.25 ug/ml in sodium bicarbonate pH 8.0, 0.1 ml/well) and incubated at 4° C. Coating solution was aspirated the following day and wells were blocked with 1 mg/ml gelatin in PBS (plus 1× thimerasol) for 2 days at 4° C. Prior to using, wells were washed 3× with wash buffer (PBS with 0.05% Tween). Cultured media samples were diluted in EIA buffer (5 mg/ml bovine γ-globulin, 1 mg/ml gelatin, 1 ml/l Tween-20, 1 mg/ml thimerasol in PBS), added to wells (0.1 ml/well) in triplicate and allowed to incubate for 1.5 hr at 37° C. in a humidified chamber. Plates were again washed and 0.1 ml/well of a mixture of rabbit anti-human TNFα polyclonal antibodies in EIA buffer (1:400 dilution of Sigma #T8300, and 1:400 dilution of Calbiochem #654250) was added for 1 hr at 37° C. Plates were washed as before and peroxidase-conjugated goat anti-rabbit IgG (H+L) antibody (Jackson ImmunoResearch #111-035-144, 1 ug/ml in EIA buffer, 0.1 ml/well) was added for 45 min. After final washing, plates were developed with peroxidase-ABTS solution (Kirkegaard/Perry #50-66-01, 0.1 ml/well). Enzymatic conversion of ABTS to colored product was measured after 5–30 minutes using a SpectroMax 340 spectrophotometer (Molecular Devices) at 405 nm. TNF levels were quantitated from a recombinant human TNFα (R&D Systems #210-TA-010) standard curve using a quadratic parameter fit generated by SoftMaxPRO software. ELISA sensitivity was approximately 30 pg TNF/ml. $IC_{50}$ values for compounds were generated using BioAssay Solver.

Preferred aminocyanopyridine MK-2 inhibiting compounds of the present invention provide TNFα release $IC_{50}$ values of below 200 $\mu$M in an in vitro cell assay. One method that can be used for determining the TNFα release $IC_{50}$ in an in vitro cell assay is that described just above. More preferred aminocyanopyridine MK-2 inhibiting compounds have the capability of providing TNFα release $IC_{50}$ values of below 50 $\mu$M, yet more preferred of below 10, and even more preferred of below 1.0 $\mu$M.

Lipopolysaccharide (LPS)-Induced TNFα Production.

Adult male 225–250 gram Lewis rats (Harlan Sprague-Dawley) were used. Rats were fasted 18 hr prior to oral dosing, and allowed free access to water throughout the experiment. Each treatment group consisted of 5 animals.

Compounds were prepared as a suspension in a vehicle consisting of 0.5% methylcellulose, 0.025% Tween-20 in PBS. Compounds or vehicle were orally administered in a volume of 1 ml using an 18 gauge gavage needle. LPS (*E. coli* serotype 0111:B4, Lot #39H4103, Cat. # L-2630, Sigma) was administered 1–4 hr later by injection into the penile vein at a dose of 1 mg/kg in 0.5 ml sterile saline. Blood was collected in serum separator tubes via cardiac puncture 1.5 hr after LPS injection, a time point corresponding to maximal TNFα production. After clotting, serum was withdrawn and stored at –20° C. until assay by ELISA (described below).

Rat LPS TNFα ELISA

ELISA plates (NUNC-Immuno™ Plate Maxisorb™ Surface) were coated with 0.1 ml per well of an Protein G purified fraction of a 2.5 ug/ml of hamster anti-mouse/rat TNFα monoclonal antibody TN19.12 (2.5 ug/ml in PBS, 0.1 ml/well). The hybridoma cell line was kindly provided by Dr. Robert Schreiber, Washington University. Wells were blocked the following day with 1 mg/ml gelatin in PBS. Serum samples were diluted in a buffer consisting of 5 mg/ml bovine γ-globulin, 1 mg/ml gelatin, 1 ml/l Tween-20, 1 mg/ml thimerasol in PBS, and 0.1 ml of diluted serum was added wells in duplicate and allowed to incubate for 2 hr at 37° C. Plates were washed with PBS-Tween, and 0.1 ml per well of a 1:300 dilution of rabbit anti-mouse/rat TNFα antibody (BioSource International, Cat. #AMC3012) was added for 1.5 hr at 37° C. Plates were washed, and a 1:1000 fold dilution of peroxidase-conjugated donkey anti-rabbit IgG antibody (Jackson ImmunoResearch, Cat. #711-035-152) was added for 45 min. After washing, plates were developed with 0.1 ml of ABTS-peroxide solution (Kirkegaard/Perry, Cat. #50-66-01). Enzymatic conversion of ABTS to colored product was measured after ~30 minutes using a SpectroMax 340 spectrophotometer (Molecular Devices Corp.) at 405 nm. TNF levels in serum were quantitated from a recombinant rat TNFα (BioSource International, Cat. #PRC3014.) standard curve using a quadratic parameter fit generated by SoftMaxPRO software. ELISA sensitivity was approximately 30 pg TNF/ml. Results are expressed in percent inhibition of the production of TNFα as compared to blood collected from control animals dosed only with vehicle.

Preferred aminocyanopyridine MK-2 inhibiting compounds of the present invention are capable of providing some degree of inhibition of TNFα in animals. That is, the degree of inhibition of TNFα in animals is over 0%. One method for determining the degree of inhibition of TNFα is the rat LPS assay that is described just above. More preferred aminocyanopyridine MK-2 inhibiting compounds have the capability of providing rat LPS TNFα inhibition values of at least about 25%, even more preferred of above 50%, yet more preferred of above 70%, and even more preferred of above 80%.

EXAMPLE 1

This illustrates the production of 2-amino-4-(2-furyl)-5H-chromeno[2,3-b]pyridine-3-carbonitrile.

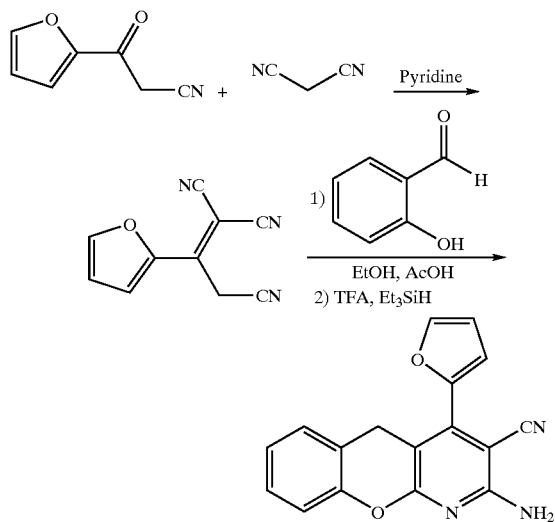

3-(2-furyl)-3-oxopropanenitrile (10 mmol, 1.0 equiv., 1.35 g) and malononitrile (10 mmol, 1.0 equiv., 600 μL) were combined in pridine (10 mL). The mixture was heated to 100° C. for 1 hour. The reaction mixture was diluted with 150 mL dichloromethane and washed with 1 M HCl (3×50 mL). The organic layer was dried and evaporated to give a dark oil (GDS-13695-130). The oil was dissolved in EtOH (30 mL) and treated with salicaldehyde (10 mmol, 1.0 equiv., 1.0 mL) and AcOH (10 mL). The resulting mixture was heated to reflux for 2 hours. The solvents were evaporated and the in vacuo and the residue was dissolved in trifluoroacetic acid (15 mL). Triethylsilane (10 mL) was added and the solution was stirred overnight. The solvents were evaporated and the residue purified by reverse phase chromatography. The product was isolated as a solid (370 mg, 13%). $^1$H NMR (400 MHz, DMSO) δ 7.99 (s, 1H), 7.24–7.20 (m, 2H), 7.08–7.04 (m, 3H), 6.94 (bs, 2H), 6.76 (s, 1H), 3.96 (s, 2H): m/z 290 (M+H).

EXAMPLE 2

This illustrates the production of 2,4-diamino-10-methyl-5,10-dihydrobenzo[b]-1,8-naphthyridine-3-carbonitrile trifluoroacetate.

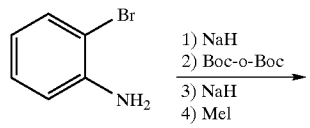
1) NaH
2) Boc-o-Boc
3) NaH
4) MeI

-continued

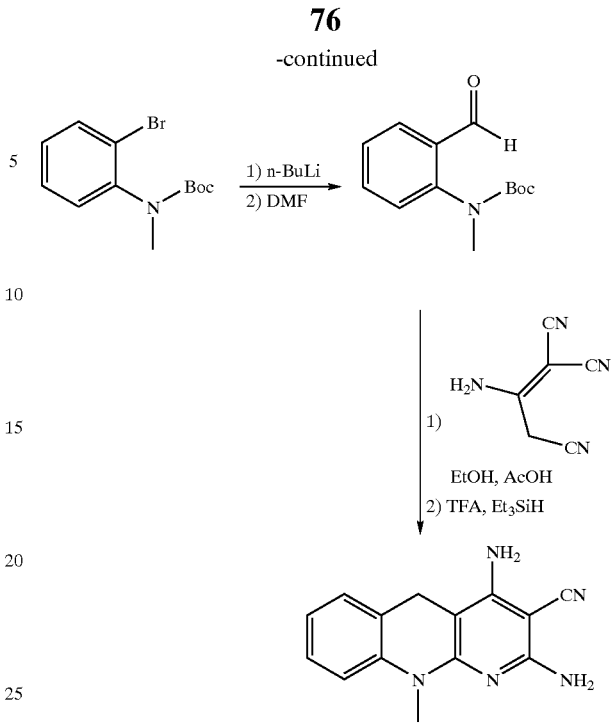

Step 1: (Synthesis of t-Butyl 2-bromophenyl(methyl) carbamate)

2-bromoaniline (25 mmol, 1.0 equiv. 4.3 g) was dissolved in THF (150 mL). Sodium hydride (60% in mineral oil, 1.1 g) was added and the mixture heated to reflux for 1 hour. After cooling to room temperature, a solution of di-t-butyl-dicarbonate in THF (1.0M, 30 mmol, 1.2 equiv., 30 mL) was added followed by sodium hydride (1.1 g). The resulting mixture was heated to reflux for 14 hours. After cooling to room temperature, Iodomethane (28 mmol, 1.12 equiv., 1.75 mL) was added and the mixture heated to reflux for 3 hours. After cooling to room temperature, the reaction was quenched with water and diluted with ether. The organic layer was washed with sat. aq. NH$_4$Cl, sat. aq. NaHCO$_3$, and sat. aq. NaCl. The organic layer was dried over MgSO$_4$, filtered and evaporated to give a yellow oil. Purification by silica gel chromatography gave the product as a yellow oil (5.9 g, 82%). $^1$H NMR (400 MHz, CDCl$_3$) δ 7.58 (d, 1H), 7.29 (t, 1H), 7.21 (d, 1H), 7.12 (t, 1H), 3.13 (s, 3H), 1.33 (s, 9H): m/z 271 (M+H).

Step 2: (Synthesis of 2,4-diamino-10-methyl-5,10-dihydrobenzo[b]-1,8-naphthyridine-3-carbonitrile trifluoroacetate)

t-Butyl 2-bromophenyl(methyl)carbamate (2.65 mmol, 1.0 equiv., 759 mg) was dissolved in THF (20 mL). The solution was cooled in a dry ice acetone bath and a solution of n-BuLi in hexane (1.6M, 1.1 equiv. 1.8 mL) was added dropwise. After 15 minutes, DMF (1 mL) was added and the reaction allowed to warm to room temperature. The reaction mixture was quenched with sat. aq. NH$_4$Cl, and partitioned between ether and water. The organic layer was washed with water and dried over MgSO$_4$, filtered and evaporated to get 820 mg of a yellow oil. This oil was carried on immediately without purification or characterization. The resulting oil was treated with 2-amino-1-propene-1,1,3-tricarbonitrile (2 mmol, 265 mg), acetic acid (2.0 mL), and ethanol (10 mL) and the resulting solution was heated to reflux overnight. The reaction slurry was concentrated in vacuo and then dissolved in trifluoroacetic acid (7 mL) at 0° C. Triethylsilane (5.0 mL) was added via syringe. The reaction stirred for 2 hours before evaporating solvents to get a brown solid. The solid was washed with dichloromethane and dried to give the product as a light brown solid. (90 mg, 9%). $^1$H NMR (400 MHz, DMSO) 87.16 (t, 1H), 7.03 (d, 1H), 6.97–6.91 (m, 2H), 3.70 (s, 2H), 3.34 (s, 3H): m/z 252 (M+H).

EXAMPLE 3

This illustrates the production of 2,4-diamino-8-ethoxy-7-hydroxy-5H-chromeno[2,3-b]pyridine-3-carbonitrile.

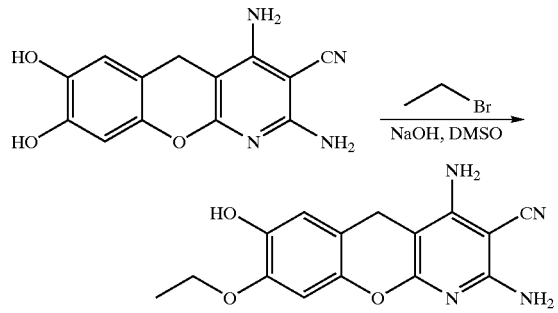

2,4-diamino-7,8-dihydroxy-5H-chromeno[2,3-b]pyridine-3-carbonitrile (400 mg, 1.0 mmol) and NaOH (166 mg, 4.2 mmol) were suspended in DMSO (5 mL) and warmed until dissolved. Ethyl bromide was added to the reaction mixture, which was heated to 85° C. until disappearance of starting material (HPCL monitoring). After neutralizing with NH$_4$Cl, the crude reaction mixture was purified by reverse phase column chromatography (gradient of acetonitrile, H$_2$O, 0.05% TFA). Evaporation of the solvent on a lyophilizer gave an orange solid as a TFA salt 2,4-diamino-8-ethoxy-7-hydroxy-5H-chromeno[2,3-b]pyridine-3-carbonitrile, which was confirmed by 2D NMR analysis. $^1$H-NMR (300 MHz, CD$_3$OD): δ 1.47 (t, 3H), 3.63 (s, 2H), 4.12 (quartet, 2H), 6.59–6.81 (m, 2H). HRMS calcd for C15H14N4O3 (M+H): 299.11. Found: 299.1132.

EXAMPLE 4

This illustrates the production of 2,4-diamino-8-(2-ethoxyethoxy)-7-hydroxy-5H-chromeno[2,3-b]pyridine-3-carbonitrile.

2,4-diamino-8-(2-ethoxyethoxy)-7-hydroxy-5H-chromeno[2,3-b]pyridine-3-carbonitrile was prepared from 2,4-diamino-8-hydroxy-5H-chromeno[2,3-b]pyridine-3-carbonitrile in the same method as described above in Example 3, using 2-bromoethyl-ethylether in lieu of 2-bromoethyl-ethylether. $^1$H-NMR (300 MHz, CD$_3$OD): δ 1.28 (t, 3H), 3.60 (s, 2H), 3.67 (quartet, 2H), 3.86 (s, 2H), 4.19 (s, 2H), 6.58–6.82 (m, 2H). HRMS calcd for C17H18N4O4 (M+H): 343.13. Found: 343.1418.

EXAMPLES 5–6

This illustrates the production of aminocyanopyridine compounds of the present invention.

The aminocyanopyridine compounds shown in the table below were prepared according to the general method described in Example 3. NMR analysis was carried out according to the method described above, and resulting data for each of the compounds is provided in the table.

| Ex. No. | Compound name | HRMS calcd | HRMS found |
|---|---|---|---|
| 5 | tert-butyl {[2,4-diamino-7-(2-tert-butoxy-2-oxoethoxy)-3-cyano-5H-chromeno[2,3-b]pyridin-8-yl]oxy}acetate trifluoroacetate | 499.21 | 499.2204 |
| 6 | 7,8-bis(allyloxy)-2,4-diamino-5H-chromeno[2,3-b]pyridine-3-carbonitrile trifluoroacetate | 351.14 | 351.1445 |

EXAMPLE 7

This illustrates the production of 2,4-diamino-7,8-dihydroxy-5H-chromeno[2,3-b]pyridine-3-carbonitrile.

To a cooled (0° C.) solution of 2,4-diamino-7,8-dimethoxy-5H-chromeno[2,3-b]pyridine-3-carbonitrile (1.34 mmol, 400 mg) and dichloromethane (4.0 mL) was slowly added boron tribromide (1 M, dichloromethane, 8.04 mmol, 8.04 mL). The suspension was stirred at 0° C. for 15 minutes, then the ice bath was removed and the reaction warmed to 23° C. overnight. After 16 h at 23° C. the reaction was cooled to 0° C. and carefully neutralized with 2.5N sodium hydroxide to pH=7. The product was collected by filtration, dissolved in dimethyl sulfoxide (1.0 mL) and purified by reverse phase chromatography. The product was isolated as a pale orange solid (62 mg, 17% yield). $^1$H NMR (400 MHz, DMSO) δ 9.071 (s, 1H), 8.795 (s, 1H), 6.520 (s, 1H), 6.410 (bs, 2H), 6.405(s, 1H), 6.244 (bs, 2H), 3.48 (s, 2H): m/z 271 (M+); HRMS (M+H) calculated for C$_{13}$H$_{11}$N$_4$O$_3$ 271.0753, found 271.0721.

EXAMPLE 8

This illustrates the production of 2,4-diamino-8-hydroxy-5H-chromeno[2,3-b]pyridine-3-carbonitrile.

2,4-Dihydroxy-benzaldehyde (43.4 mmol, 6.0 g), 2-amino-1-propene-1,1,3-tricarbonitrile (43.4 mmol, 5.74 g), acetic acid (13.0 mL), and ethanol (125.0 mL) were combined and heated to reflux for 2 hours. The reaction slurry was concentrated in vacuo and then dissolved in trifluoroacetic acid (160.0 mL) at 0° C. Triethylsilane (0.28 mol, 32.76 g, 45.0 mL) was added via syringe. The reaction was stirred for 1 hour at 0° C. 300 mL of dichloromethane was added to the reaction and the solid was collected via filtration and washed (2×75 mL) with dichloromethane and ether. The product was isolated as a pale orange solid (13.10 g, 63% yield). $^1$H NMR (400 MHz, DMSO) δ 6.958(d, 1H), 6.537 (dd, 1H), 6.390 (d, 1H), 3.510(s, 2H): m/z 255 (M+); HRMS (M+H) calculated for C$_{13}$H$_{11}$N$_4$O$_2$ 255.0804, found 255.0894.

EXAMPLE 9

This illustrates the production of 8,10-diamino-2,3-dihydro-11H-[1,4]dioxino[2',3':6,7]chromeno[2,3-b]pyridine-9-carbonitrile.

2,4-diamino-7,8-dihydroxy-5H-chromeno[2,3-b]pyridine-3-carbonitrile (0.56 mmol, 150 mg) was dissolved in DMSO (3.0 mL) and sodium hydroxide (2.24 mmol, 90 mg) was added followed by dibromoethane (0.56 mmol, 105.20 mg, 48.26 µL). The dark homogeneous solution was heated to 70° C. for 16 hours. The crude reaction mixture was cooled to 23° C., neutralized with trifluoroacetic acid and directly purified via reverse phase chromatography. The product was isolated as a pale orange solid (30 mg, 18% yield). $^1$H NMR (400 MHz, CD$_3$OD) δ 6.715(s, 1H), 6.553 (s, 1H), 4.215 (bs, 4H), 3.575(s, 2H): m/z 298 (M+H).

EXAMPLE 10

This illustrates the production of 2,4-diamino-8-(2-ethoxyethoxy)-5H-chromeno[2,3-b]pyridine-3-carbonitrile.

2,4-diamino-8-hydroxy-5H-chromeno[2,3-b]pyridine-3-carbonitrile (0.62 mmol, 300 mg) was dissolved in DMSO (4.0 mL) and solid sodium hydroxide (2.79 mmol, 111.6 mg) was added followed by 2-bromoethyl-ethylether (0.62 mmol, 69.9 μL). The reaction was heated to 80° C. with stirring for 9 hours. The crude reaction was filtered and diluted with DMSO (4.0 mL) and purified via reverse phase chromatography. The product was isolated as a tan solid (80 mg, 40% yield). $^1$H NMR (400 MHz, CD$_3$OD) δ 7.180(d, 1H), 6.795 (d, 1H), 6.46 (d, 1H), 4.090 (t, 2H), 3.766(t, 2H), 3.607 (s, 2H), 3.572 (t, 2H), 1.200 (t, 2H); m/z 327 (M+H).

EXAMPLE 11

This illustrates the production of 2,4-diamino-8-(2-pyrrolidin-1-ylethoxy)-5H-chromeno[2,3-b]pyridine-3-carbonitrile.

2,4-diamino-8-(2-pyrrolidin-1-ylethoxy)-5H-chromeno[2,3-b]pyridine-3-carbonitrile was prepared from 2,4-diamino-8-hydroxy-5H-chromeno[2,3-b]pyridine-3-carbonitrile in the same manner as described in Example 10, using 1-(2-chloroethyl)pyridine in lieu of 2-bromoethyl-ethylether. The product was isolated as a tan solid (100 mg, 46% yield).

$^1$H NMR (400 MHz, CD$_3$OD) δ 7.199 (d, 1H), 6.680 (d, 1H), 6.668 (d, 1H), 4.290 (t, 2H), 3.618 (s, 2H), 3.562 (t, 2H), 3.375 (bs, 4H), 2.077(bs, 4H); m/z 352 (M+H). TNFα release assay IC$_{50}$: 2.9 μM; Rat LPS Assay 60% inhibition at 20 mpk (IP).

EXAMPLE 12

This illustrates the production of 2,4-diamino-8-(2-aminoethoxy)-5H-chromeno[2,3-b]pyridine-3-carbonitrile.

2,4-diamino-8-(2-aminoethoxy)-5H-chromeno[2,3-b]pyridine-3-carbonitrile was prepared from 2,4-diamino-8-hydroxy-5H-chromeno[2,3-b]pyridine-3-carbonitrile in the same manner as described in Example 10 using 2-bromoethylamine in lieu of 2-bromoethyl-ethylether. The product was isolated as a tan solid (167 mg, 51% yield). $^1$H NMR (400 MHz, DMSO) δ 8.180 (bs, 2H), 7.100 (d, 1H), 6.762 (d, 1H), 6.646 (bs, 1H), 4.154 (t, 2H), 3.573 (s, 2H), 3.155 (t, 2H); m/z 398 (M+H). TNFα release assay IC$_{50}$: 6.9 μM; Rat LPS Assay 88% inhibition at 20 mpk (IP).

EXAMPLE 13

This illustrates the production of [(2,4-diamino-3-cyano-5H-chromeno[2,3-b]pyridin-8-yl)oxy]acetic acid.

[(2,4-diamino-3-cyano-5H-chromeno[2,3-b]pyridin-8-yl)oxy]acetic acid was prepared from 2,4-diamino-8-hydroxy-5H-chromeno[2,3-b]pyridine-3-carbonitrile in the same manner as described in Example 10 using bromoacetic acid in lieu of 2-bromoethyl-ethylether. The product was isolated as a tan solid (110.6 mg, 31% yield). $^1$H NMR (400 MHz, DMSO) δ 7.030 (d, 1H), 6.640 (d, 1H), 6.516 (d, 1H), 6.474 (bs, 2H), 6.278 (bs, 2H), 4.633 (s, 2H), 3.543 (s, 2H); m/z 427 (M+H).

EXAMPLE 14

This illustrates the production of 2,4-diamino-8-(2-hydroxyethoxy)-5H-chromeno[2,3-b]pyridine-3-carbonitrile.

2,4-diamino-8-(2-hydroxyethoxy)-5H-chromeno[2,3-b]pyridine-3-carbonitrile was prepared from 2,4-diamino-8-hydroxy-5H-chromeno[2,3-b]pyridine-3-carbonitrile in the same manner as described in Example 10 using 2-bromoethanol in lieu of 2-bromoethyl-ethylether. The product was isolated as a tan solid (120 mg, 35% yield). $^1$H NMR (400 MHz, DMSO) δ 7.025 (d, 1H), 6.670 (d, 1H), 6.550 (d, 1H), 3.931 (t, 2H), 3.662 (t, 2H), 3.546 (s, 2H); m/z 413 (M+H).

EXAMPLE 15

This illustrates the production of 2,4-diamino-8-(2-morpholin-4-ylethoxy)-5H-chromeno[2,3-b]pyridine-3-carbonitrile.

2,4-diamino-8-(2-morpholin-4-ylethoxy)-5H-chromeno[2,3-b]pyridine-3-carbonitrile was prepared from 2,4-diamino-8-hydroxy-5H-chromeno[2,3-b]pyridine-3-carbonitrile in the same manner as described in Example 10 using 1-(2-chloroethyl)morpholine in lieu of 2-bromoethyl-ethylether. The product was isolated as a tan solid (80 mg, 17% yield). $^1$H NMR (400 MHz, DMSO) δ 7.071 (d, 1H), 6.714 (d, 1H), 6.654 (d, 1H), 6.527 (bs, 2H), 6.323 (bs, 2H), 4.311 (t, 2H), 3.938 (m, 2H), 3.664 (t, 2H), 3.558 (s, 2H), 3.534 (m, 2H), 3.451 (m, 2H), 3.158 (m, 2H); m/z 482 (M+H).

EXAMPLES 16–22

This illustrates the production of aminocyanopyridine compounds of the present invention.

The aminocyanopyridine compounds shown in the table below were prepared according to the general method described in Example 10. NMR analysis was carried out according to the method described above, and resulting data for each of the compounds is provided in the table.

| Ex. No. | Compound name | m/z (M + H) |
|---|---|---|
| 16 | 2,4-diamino-8-methoxy-5H-chromeno[2,3-b]pyridine-3-carbonitrile | 269 |
| 17 | 7,9-diamino-10H-[1,3]dioxolo[6,7]chromeno[2,3-b]pyridine-8-carbonitrile | 283 |
| 18 | 8-(allyloxy)-2,4-diamino-5H-chromeno[2,3-b]pyridine-3-carbonitrile trifluoroacetate | 295 |

-continued

| Ex. No. | Compound name | m/z (M + H) |
|---|---|---|
| 19 | 2-amino-8-ethoxy-4-(ethylamino)-5H-chromeno[2,3-b]pyridine-3-carbonitrile | 311 |
| 20 | 8-ethoxy-2,4-bis(ethylamino)-5H-chromeno[2,3-b]pyridine-3-carbonitrile | 339 |
| 21 | 2-amino-8-(2-ethoxyethoxy)-4-[(2-ethoxyethyl)amino]-5H-chromeno[2,3-b]pyridine-3-carbonitrile | 399 |
| 22 | 2,4-diamino-8-[2-(dimethylamino)ethoxy]-5H-chromeno[2,3-b]pyridine-3-carbonitrile trifluoroacetate | 326 |

EXAMPLE 23

This illustrates the production of 2,4-diamino-9-methoxy-5H-chromeno[2,3-b]pyridine-3-carbonitrile bis(trifluoroacetate).

3-Methoxysalicyaldehyde (10 mmol, 1.52 g), 2-amino-1-propene-1,1,3-tricarbonitrile (10 mmol, 1.32 g) acetic acid (2.5 mL), and ethanol (40 mL) were combined and heated to reflux overnight. The reaction slurry was concentrated in vacuo and then dissolved in trifluoroacetic acid (15 mL) at 0° C. Triethylsilane (62 mmol, 7.2 g, 10 mL) was added via syringe. The reaction stirred for one hour at room temperature. Dichloromethane (100 mL) was added to the reaction and the solid formed was collected via filtration and washed with dichloromethane (2×). The product was isolated as a white solid (2.5 g, 50% yield). $^1$H NMR (300 MHz, DMSO-$d_6$): δ 7.08 (t, J=8 Hz, 1H), 7.00–6.80 (m, 2H), 6.73 (d, J=7.4 Hz, 2H), 3.83(s, 3H), 3.68 (s, 2H); m/z 269 (M+H); Anal. calculated for $C_{14}H_{12}N_4O_2$-2$CF_3CO_2H$: C, 43.56; H, 2.84; N, 11.29, found: C, 43.40; H, 2.98; N, 11.32.

EXAMPLE 24

This illustrates the production of 2,4-diamino-7-hydroxy-5H-chromeno[2,3-b]pyridine-3-carbonitrile trifluoroacetate.

2,4-diamino-7-hydroxy-5H-chromeno[2,3-b]pyridine-3-carbonitrile was prepared in the same manner as described in Example 23, except that 5-hydroxysalicyaldehyde was used in place of methoxysalicyaldehyde. The product was isolated as a pink solid (951 mg, 30% yield). $^1$H NMR (300 MHz, DMSO-$d_6$): δ 6.88 (d, J=8.8 Hz, 1H), 6.63 (d, J=8.7 Hz, 1H), 6.55(s, 1H), 3.6 (s, 2H): m/z 255 (M+H); Anal. calculated for $C_{13}H_{10}N_4O_2$-1.5$CF_3CO_2H$-0.5$H_2O$: C, 44.25; H, 2.90; N, 12.90, found: C, 44.04; H, 3.05; N, 12.84.

EXAMPLE 25

This illustrates the production of 2,4-diamino-5H-chromeno[2,3-b]pyridine-3-carbonitrile Bis(trifluoroacetate).

2,4-diamino-5H-chromeno[2,3-b]pyridine-3-carbonitrile was prepared in the same manner as described in Example 23 except that salicyaldehyde was used in place of methoxysalicyaldehyde. The product was isolated as a light tan solid (1.26 g, 33% yield). $^1$H NMR (300 MHz, DMSO-$d_6$), δ 7.30–6.90 (m, 6H), 3.7 (s, 2H); m/z 239 (M+H); Anal. Calcd for $C_{13}H_{10}N_4O$-2$CF_3CO_2H$-0.25$H_2O$: C, 43.37; H, 2.68; N, 11.90, found: C, 43.07; H, 2.81; N, 11.79.

EXAMPLE 26

This illustrates the production of 2,4-diamino-8,9-dihydroxy-5H-chromeno[2,3-b]pyridine-3-carbonitrile trifluoroacetate.

2,4-diamino-8,9-dihydroxy-5H-chromeno[2,3-b]pyridine-3-carbonitrile was prepared in the same manner as described in Example 23, except that 2,3,4-trihydroxybenzaldehyde was used in place of methoxysalicyaldehyde. The product was isolated as a white solid (3.6 g, 82% yield). $^1$H NMR (500 MHz, DMSO-$d_6$): δ 7.1 (bs, 3H), 6.58 (d, J=8 Hz, 1H), 6.47 (d, J=8 Hz, 1H), 3.75 (s, 2H); m/z 271 (M+H).

EXAMPLE 27

This illustrates the production of 2,4-diamino-9-hydroxy-8-methoxy-5H-chromeno[2,3-b]pyridine-3-carbonitrile trifluoroacetate.

2,3-dihydroxy-4-methoxybenzaldehyde (3 mmol, 506 mg), 2-amino-1-propene-1,1,3-tricarbonitrile (3 mmol, 398 mg), acetic acid (1 mL), and ethanol (15 mL) were combined and heated to reflux overnight. The reaction slurry was concentrated in vacuo and then dissolved in trifluoroacetic acid (10 mL) at 0° C. Triethylsilane (25 mmol, 2.88 g, 4 mL) was added via syringe. The reaction stirred for overnight at room temperature to give a yellow slurry. Dichloromethane (50 mL) was added to the reaction and the solid formed was collected via filtration and washed with dichloromethane (2×). The product was isolated as a yellow solid (482 mg, 35% yield). $^1$H NMR (300 MHz, DMSO-$d_6$): δ 6.73 (d, J=8.5 Hz, 1H), 6.57 (d, J=8.5 Hz, 1H), 3.77(s, 3H), 3.57 (s, 2H); m/z 285 (M+H); Anal. calculated for $C_{14}H_{12}N_4O_3$-1.25$CF_3CO_2H$-1.5$H_2O$: C, 43.58; H, 3.62; N, 12.32, found: C, 43.80; H, 3.22; N, 12.65.

EXAMPLE 28

This illustrates the production of 2,4-diamino-9-hydroxy-5H-chromeno[2,3-b]pyridine-3-carbonitrile trifluoroacetate.

2,3-dihydroxybenzaldehyde (5 mmol, 691 mg), 2-amino-1-propene-1,1,3-tricarbonitrile (5 mmol, 661 mg), acetic acid (1.2 mL), and ethanol (20 mL) were combined and heated to reflux overnight. The reaction slurry was concentrated in vacuo and then dissolved in trifluoroacetic acid (20 mL) at 0° C. Triethylsilane (62 mmol, 7.2 g, 10 mL) was added via syringe. The reaction stirred for two and one-half days at room temperature to give a solution, which was concentrated in vacuo. The residue was stirred in methanol and the slurry was filtered. The product was obtained as a brown solid by concentrating the filtrate (167 mg, 9% yield). $^1$H NMR (300 MHz, DMSO-$d_6$): δ 6.91 (t, J=7.7 Hz, 1H), 6.86–6.70 (m, 2H), 6.59 (d, J=7.3 Hz 1H), 3.61 (s, 2H); m/z 255 (M+H).

EXAMPLE 29

This illustrates the production of 2,4,7-triamino-5H-chromeno[2,3-b]pyridine-3-carbonitrile.

Step 1: Preparation of 2,4-diamino-7-nitro-5H-chromeno[2,3-b]pyridine-3-carbonitrile: 5-nitrosalicylaldehyde (132 mmol, 22.00 g), 2-amino-1-propene-1,1,3-tricarbonitrile (132 mmol, 17.39 g), acetic acid (31 mL), and ethanol (500 mL) were combined and heated to reflux overnight. The resulting slurry was concentrated in vacuo and then dissolved in trifluoroacetic acid (350 mL) at 0° C. Triethylsilane (1.40 mol, 162 g, 225 mL) was added. The mixture was heated overnight at 66° C. The mixture was cooled and concentrated in vacuo. Triturating with methanol gave 2,4-diamino-7-nitro-5H-chromeno[2,3-b]pyridine-3-carbonitrile as a yellow solid (22.48 g, 60% yield). $^1$H NMR (300 MHz, DMSO-$d_6$): δ 8.13 (d, J=9.0 Hz, 1H), 8.00 (s, 1H), 7.25 (d, J=9.0 Hz, 1H), 6.70 (br s, 2H), 6.50 (bs, 2H), 3.82 (s, 2H); m/z 284 (M+H); Anal. Calcd for $C_{13}H_9N_5O_3$-0.5$H_2O$: C, 53.43; H, 3.45; N, 23.96, found: C, 53.41; H, 3.17; N, 23.71.

Step 2: A mixture of 2,4-diamino-7-nitro-5H-chromeno[2,3-b]pyridine-3-carbonitrile, produced as described above, (0.55 mmol, 155 mg) and Pd/C (35 mg, 10% on activated carbon) in DMF (15 mL) was stirred under an atmosphere of hydrogen (balloon) for 3.5 hours. The catalyst was removed by filtration using a plug of celite. The filtrated was concentrated in vacuo and the residue was triturated with methanol to give 2,4,7-triamino-5H-chromeno[2,3-b]pyridine-3-carbonitrile as a grey solid (109 mg, 79% yield). $^1$H NMR (300 MHz, DMSO-$d_6$): δ 6.72 (d, J=8.0 Hz, 1H), 6.39–6.5(m, 4H), 6.25 (s, 2H), 3.52 (s, 2H); m/z 254 (M+H).

EXAMPLE 30

This illustrates the production of 2,4-diamino-9-fluoro-5H-chromeno[2,3-b]pyridine-3-carbonitrile trifluoroacetate.

3-Fluoro-2-hydroxybenzaldehyde (3.45 mmol, 484 mg), 2-amino-1-propene-1,1,3-tricarbonitrile (3.50 mmol, 463 mg), acetic acid (0.9 mL) and ethanol (27 mL) were combined and heated to reflux for 14 hours. The reaction slurry was concentrated in vacuo and then dissolved in trifluoroacetic acid (10.5 mL). Triethylsilane (43 mmol, 4.97 g, 6.9 mL) was added via syringe. The reaction was heated to reflux for 5 hours. Dichloromethane (50 mL) was added to the reaction and the solid formed was collected via filtration and washed with methanol. The product was isolated as a white solid (377 mg, 30% yield). $^1$H NMR (500 MHz, DMSO-$d_6$): δ 7.25–7.19 (m, 1H), 7.15–7.08 (m, 1H), 7.00–6.96 (m, 1H), 6.70 (bs, 2H), 6.51 (bs, 2H), 3.75 (S, 2H); m/z 257 (M+H).

EXAMPLE 31

This illustrates the production of 2,4-diamino-3-cyano-5H-chromeno[2,3-b]pyridine-7-carboxylic acid Bis (trifluoroacetate).

5–Carboxysalicylaldehyde (3 mmol, 500 mg), 2-amino-1-propene-1,1,3-tricarbonitrile (3 mmol, 396 mg) acetic acid (1.2 mL), and ethanol (15 mL) were combined and heated to reflux for 2.5 days. The reaction slurry was concentrated in vacuo and then dissolved in trifluoroacetic acid (10 mL). Triethylsilane (62 mmol, 7.2 g, 10 mL) was added via syringe. The reaction was stirred for 4 hours at 50° C. and then was stirred overnight at room temperature. Dichloromethane (20 mL) was added to the reaction and the solid formed was collected via filtration and washed with dichloromethane (2×). The product was isolated as a yellow solid (560 mg, 36% yield). $^1$H NMR (500 MHz, DMSO-$d_6$): δ 7.86 (d, J=7.4 Hz, 1H), 7.85 (s, 1H), 7.31 (d, J=7.4 Hz, 1H), 6.80 (brs, 2H), 3.85 (s, 2H); m/z 283 (M+H); anal. Calculated for $C_{14}H_{10}N_4O_3$-2$CF_3CO_2H$-0.25$H_2O$: C, 42.00; H, 2.45; N, 10.88, found: C, 42.30; H, 2.31; N, 10.51.

EXAMPLE 32

This illustrates the production of 2,4-diamino-6,8-dihydroxy-5H-chromeno[2,3-b]pyridine-3-carbonitrile trifluoroacetate.

2,4-diamino-6,8-dihydroxy-5H-chromeno[2,3-b]pyridine-3-carbonitrile was prepared in the same manner as described in Example 31, except that 2,4,6-trihydroxybenzaldehyde was used in place of 5-carboxysalicylaldehyde. The product was isolated as an orange solid (106 mg, 9% yield). $^1$H NMR (free base, 300 MHz, DMSO-$d_6$): δ 9.65 (s, 1H), 9.40 (s, 1H), 6.41 (s, 2H), 6.35 (s, 2H), 6.10 (s, 1H), 5.85 (s, 1H), 3.31 (s, 2H); m/z 271 (M+H).

EXAMPLES 33–51

This illustrates the production of aminocyanopyridine compounds of the present invention.

The aminocyanopyridine compounds shown in the table below were prepared according to the general method described in Example 29. NMR analysis was carried out according to the method described above, and resulting data for each of the compounds is provided in the table.

| Ex. No. | Compound name | M + H |
|---|---|---|
| 33 | 2,4-diamino-7-(dimethylamino)-5H-chromeno[2,3-b]pyridine-3-carbonitrile | 282 |
| 34 | 2,4-diamino-7-nitro-5H-chromeno[2,3-b]pyridine-3-carbonitrile | 284 |
| 35 | 2,4-diamino-7-chloro-9-methyl-5H-chromeno[2,3-b]pyridine-3-carbonitrile | 287 |
| 36 | 2,4-diamino-6,8-dimethoxy-5H-chromeno[2,3-b]pyridine-3-carbonitrile trifluoroacetate | 299 |
| 37 | 2,4-diamino-7-(trifluoromethoxy)-5H-chromeno[2,3-b]pyridine-3-carbonitrile trifluoroacetate | 323 |
| 38 | 2,4-diamino-7-bromo-9-methoxy-5H-chromeno[2,3-b]pyridine-3-carbonitrile trifluoroacetate | 347 |
| 39 | 2,4-diamino-9-methoxy-7-nitro-5H-chromeno[2,3-b]pyridine-3-carbonitrile trifluoroacetate | 314 |
| 40 | 2,4-diamino-8-methyl-5H-chromeno[2,3-b]pyridine-3-carbonitrile trifluoroacetate | 253 |
| 41 | 2,4-diamino-3-cyano-5H-chromeno[2,3-b]pyridine-9-carboxylic acid bis(trifluoroacetate) | 283 |
| 42 | 2,4-diamino-6-methoxy-5H-chromeno[2,3-b]pyridine-3-carbonitrile bis(trifluoroacetate) | 269 |
| 43 | 2,4-diamino-9-bromo-7-chloro-5H-chromeno[2,3-b]pyridine-3-carbonitrile trifluoroacetate | 351 |
| 44 | 2,4-diamino-6-bromo-9-methoxy-5H-chromeno[2,3-b]pyridine-3-carbonitrile trifluoroacetate | 347 |
| 45 | 2,4,7-triamino-9-methoxy-5H-chromeno[2,3-b]pyridine-3-carbonitrile trifluoroacetate | 284 |
| 46 | 2,4-diamino-9-nitro-5H-chromeno[2,3-b]pyridine-3-carbonitrile | 284 |
| 47 | 2,4,9-triamino-5H-chromeno[2,3-b]pyridine-3-carbonitrile trifluoroacetate | 254 |
| 48 | 2,4-diamino-7-fluoro-5H-chromeno[2,3-b]pyridine-3-carbonitrile trifluoroacetate | 257 |
| 49 | 2,4-diamino-7-chloro-5H-chromeno[2,3-b]pyridine-3-carbonitrile | 273 |
| 50 | 2,4-diamino-9-tert-butyl-5H-chromeno[2,3-b]pyridine-3-carbonitrile | 295 |
| 51 | ethyl 2,4-diamino-3-cyano-5H-chromeno[2,3-b]pyridine-9-carboxylate | 311 |

EXAMPLE 52

This illustrates the production of 2,4-diamino-7-nitro-5H-thiochromeno[2,3-b]pyridine-3-carbonitrile.

Step 1: Production of 5-Nitrothiosalicylaldehyde: A mixture of 2-chloro-5-nitrobenzaldehyde (2 g, 11 mmol) and lithium sulfide (0.54 g, 11.7 mmol) in 30 mL of anhydrous DMSO was stirred under nitrogen at room temperature overnight. The solution was then added to a mixture of ice-water, acidified with 2N HCl and extracted with ether three times. The combined ether layers were washed with water, brine, dried, filtered and concentrated to give the crude 5-nitro-2-thiosalicylaldehyde as an orange solid (1.3 g, 65% yield)

Step 2: A solution of the crude 5-nitro-2-thiosalicylaldehyde (1.3 g, 7.1 mmol), 2-amino-1-propene-1,1,3-tricarbonitrile (7.6 mmol, 1 g), acetic acid (2.5 mL) in 70 mL of ethanol was heated at 76° C. under nitrogen overnight. The reaction mixture was cooled to room temperature and filtered. The solid was washed with ethanol to give the desired tricyclic intermediate as a light brown solid (1.5 g, 71.4% yield).

Step 3: A reaction mixture of the aforementioned tricyclic intermediate (1.2 g, 4 mmol) and triethylsilane (15 mL) in 100 mL of trifluoroacetic acid was heated at between 60–65° C. under nitrogen for 2 hours. After that, the solution was cooled to room temperature and concentrated in vacuo. Ether was added to the residue. The solid was filtered, washed with additional ether to give 2,4-diamino-7-nitro-5H-thiochromeno[2,3-b]pyridine-3-carbonitrile as an orange powder (0.9 g, 75% yield). $^1$H NMR (400 MHz, $CD_3CN+D_2O$) δ 8.089 (d, 1H), 8.046 (dd, 1H), 7.609 (d, 1H), 3.898 (s, 2H); m/z 300 (M+H).

EXAMPLE 53

This illustrates the production of 2,4,7-triamino-5H-thiochromeno[2,3-b]pyridine-3-carbonitrile trifluoroacetate.

To 2,4-diamino-7-nitro-5H-thiochromeno[2,3-b]pyridine-3-carbonitrile (produced as described above in Example 52; 0.8 g, 2.7 mmol) in 9 mL of 50% (by weight) of ethanol-water was added iron powder (0.55 g, 10 mmol). The mixture was heated to 60° C. and then 0.5 mL of HCl/ethanol (prepared from 5.2 mL of conc. HCl and 25 mL of 50% of ethanol-water) was added. The resulting mixture was heated at 76° C. for 2.5 hours and filtered hot. The solid was washed with 50% ethanol-water. The filtrates were combined and concentrated in vacuo to give a brownish yellow solid. The solid was then dissolved in acetonitrile, filtered to remove a small amount of insoluble solid and concentrated in vacuo. The resulting solid was then washed with methanol and trifluoroacetic acid. The trifluoroacetic acid filtrate was concentrated in vacuo to give an amber oil. Ether was added and the solid was filtered, washed with ether, air-dried overnight and then dried in a vacuum oven at 44° C. for 2 hours to give the product as a grayish solid (0.53 g, 71% yield). $^1$H NMR (400 MHz, $CD_3CN+D_2O$) δ 7.153 (d, 1H), 6.792 (s, 1H), 6.698 (d, 1H), 3.628 (s, 2H); m/z 270 (M+H).

EXAMPLE 54

This illustrates the production of 2,4-diamino-7-nitro-5H-thiochromeno[2,3-b]pyridine-3-carbonitrile 10,10-dioxide.

To a solution of 2,4-diamino-7-nitro-5H-thiochromeno[2,3-b]pyridine-3-carbonitrile, produced as described in Example 52, (3 g, 10 mmol) in 125 mL of trifluoroacetic acid cooled with a water bath was added dropwise 30% hydrogen peroxide (8 g). After addition was completed, the water bath was removed. After 4 hours, additional 30% hydrogen peroxide (2 g) was added and stirring at room temperature was continued for additional 2 hours. After that, water (20 mL) was added and the resulting solution was concentrated to about 70 mL. Then more water was added and the yellow suspension was stirred at room temperature overnight. The suspension was filtered and washed with water to give the desired product as a yellow solid (2 g, 60.4% yield). $^1$H NMR(400 MHz, DMSO+$D_2O$) δ 8.350 (dd, 1H), 8.265 (d, 1H), 8.220 (d, 1H), 4.160 (s, 2H); m/z 332 (M+H).

EXAMPLE 55

This illustrates the production of 2,4,7-triamino-5H-thiochromeno[2,3-b]pyridine-3-carbonitrile 10,10-dioxide.

A mixture of 2,4-diamino-7-nitro-5H-thiochromeno[2,3-b]pyridine-3-carbonitrile 10,10-dioxide, produced as described in Example 54, (0.8 g, 2.4 mmol) and iron powder (0.58 g, 10 mmol) in 50% of ethanol-water (10 mL) was heated to 70° C., then 1 mL of HCl/ethanol (prepared from 5.2 mL of conc. HCl and 25 mL of 50% of ethanol-water) was added. The resulting mixture was heated at 76° C. for 3 hours and filtered hot. The solid was washed with methanol and trifluoroacetic acid. The trifluoroacetic acid filtrate was concentrated in vacuo and ether was added to the viscous oil. The solid was filtered and washed with ether to give the desired product as a beige solid (0.42 g, 57.5% yield). $^1$H NMR (400 MHz, DMSO+$D_2O$) δ 7.521 (d, 1H), 6.60 (dd, 1H), 6.529 (s, 1H), 3.753 (s, 2H); m/z 302 (M+H).

EXAMPLE 56

This illustrates the production of 2,4-diamino-7-fluoro-5H-thiochromeno[2,3-b]pyridine-3-carbonitrile.

2,4-diamino-7-fluoro-5H-thiochromeno[2,3-b]pyridine-3-carbonitrile was prepared as a bis-trifluoroacetate in the same manner as described in Example 52, except that 2,5-difluorobenzaldehyde was used as the starting material in place of 2-chloro-5-nitrobenzaldehyde. The product was isolated as a beige solid (0.35 g, 35% yield). $^1$H NMR (400 MHz, $CD_3CN+D_2O$), δ 7.425 (dd, 1H), 7.153 (dd, 1H), 7.088 (dt, 1H) 3.743 (s, 2H); m/z 273 (M+H)

EXAMPLE 57

This illustrates the production of 2,4-diamino-5H-thiochromeno[2,3-b]pyridine-3-carbonitrile Bis (trifluoroacetate).

2,4-diamino-5H-thiochromeno[2,3-b]pyridine-3-carbonitrile was prepared in the same manner as described in Example 52, except that 2-fluorobenzaldehyde was used as the starting material in place of 2-chloro-5-nitrobenzaldehyde. The product was isolated as a beige solid (1.8 g, 47.4% yield). $^1$H NMR (400 MHz, $CD_3CN+D_2O$) δ 7.271–7.435 (m, 4H), 3.785 (s, 2H); m/z 255 (M+H).

EXAMPLE 58

This illustrates the production of 2,4-diamino-7-methoxy-5H-thiochromeno[2,3-b]pyridine-3-carbonitrile.

2,4-diamino-7-methoxy-5H-thiochromeno[2,3-b]pyridine-3-carbonitrile was prepared in the same manner as described in Example 52, except that 2-fluoro-5-methoxybenzaldehyde was used as the starting material. The product was isolated as a beige solid (0.5 g, 49% yield). $^1$H NMR (400 MHz, $CD_3CN+D_2O$) δ 7.329 (d, 1H), 6.938 (d, 1H), 6.885 (dd, 1H), 3.795 (s, 3H), 3.710 (s, 2H); m/z 285 (M+H)

EXAMPLE 59

This illustrates the production of 2,4-diamino-7-hydroxy-5H-thiochromeno[2,3-b]pyridine-3-carbonitrile.

A mixture of 2,4-diamino-7-methoxy-5H-thiochromeno[2,3-b]pyridine-3-carbonitrile (0.3 g, 0.59 mmol), produced as described in Example 58, and 0.6 mL of boron tribromide (6.4 mmol) in 30 mL of methylene chloride was stirred at room temperature for 18 h. After that, the solid was filtered, washed with methylene chloride, water and methanol. The methanol filtrate was concentrated to give a solid, which was washed with water, acetonitrile and ether to give the desired product as a red solid (54 mg, 33.6% yield). $^1$H NMR (400 MHz, DMSO+D$_2$O) δ 9.520 (s, 1H), 8.111 (d, 1H), 7.561 (d, 1H), 7.522 (s, 2H); m/z 271 (M+H).

EXAMPLE 60

This illustrates the production of 2,4-diamino-7-nitro-5H-thiochromeno[2,3-b]pyridine-3-carbonitrile 10,10-dioxide (an alternative procedure).

A mixture of 2,4,7-triamino-5H-thiochromeno[2,3-b]pyridine-3-carbonitrile (0.1 g, 0.26 mmol), produced as described in Example 55, and 30% hydrogen peroxide (1.5 mL) in 3 mL of trifluoroacetic acid was stirred at room temperature overnight. Water (30 mL) was then added and the resulting suspension was stirred at ambient temperature for 2 hours. The solid was filtered to give the desired product as a yellow solid (18 mg, 8.6% yield): $^1$H NMR (400 MHz, DMSO+D$_2$O) δ 8.353 (dd, 1H), 8.263 (d, 1H), 8.228 (d, 1H), 4.163 (s, 2H); m/z 332 (M+H).

EXAMPLE 61

This illustrates the production of 2,4-diamino-7-fluoro-5H-thiochromeno[2,3-b]pyridine-3-carbonitrile 10,10-dioxide.

2,4-diamino-7-fluoro-5H-thiochromeno[2,3-b]pyridine-3-carbonitrile 10,10-dioxide was prepared in the same manner as 2,4-diamino-7-nitro-5H-thiochromeno[2,3-b]pyridine-3-carbonitrile 10,10-dioxide, as described in Example 60. The product was isolated as a yellow solid (51 mg, 32.7% yield). $^1$H NMR (400 MHz, DMSO) δ 8.028 (q, 1H), 7.433 (dt, 1H), 7.253 (d, 1H), 7.162 (bs, 1H), 6.917 (bs, 1H), 4.024 (s, 2H); m/z 305 (M+H).

EXAMPLE 62

This illustrates the production of 2,4-diamino-5H-thiochromeno[2,3-b]pyridine-3-carbonitrile 10,10-dioxide.

2,4-diamino-5H-thiochromeno[2,3-b]pyridine-3-carbonitrile 10,10-dioxide was prepared in the same manner as 2,4-diamino-7-nitro-5H-thiochromeno[2,3-b]pyridine-3-carbonitrile 10,10-dioxide, as described in Example 60. The product was isolated as a yellow solid (73 mg, 42.9% yield). $^1$H NMR (400 MHz, DMSO) δ 7.945 (dd, 1H), 7.762 (dt, 1H), 7.568 (t, 1H), 7.467 (d, 2H), 7.179 (bs, 2H), 6.886 (bs, 1H), 4.009 (s, 2H); m/z 287 (M+H).

EXAMPLE 63

This illustrates the production of 2,4-diamino-7-methoxy-5H-thiochromeno[2,3-b]pyridine-3-carbonitrile 10,10-dioxide.

2,4-diamino-7-methoxy-5H-thiochromeno[2,3-b]pyridine-3-carbonitrile 10,10-dioxide was prepared in the same manner as 2,4-diamino-7-nitro-5H-thiochromeno[2,3-b]pyridine-3-carbonitrile 10,10-dioxide, as described in Example 60. The product was isolated as a light brown solid (110 mg, 34.2% yield). $^1$H NMR (400 MHz, DMSO+D$_2$O) δ 7.858 (d, 1H), 7.107 (dd, 1H), 6.972 (d, 1H), 3.942 (2, 2H), 3.833 (s, 3H); m/z 316 (M+H).

EXAMPLES 64–65

This illustrates the production of aminocyanopyridine compounds of the present invention.

The aminocyanopyridine compounds shown in the table below were prepared according to the general method described in Example 60. NMR analysis was carried out according to the method described above, and resulting data for each of the compounds is provided in the table.

| Ex. No. | Compound name | m/z (M + H) |
|---|---|---|
| 64 | 2,4-diamino-9-fluoro-5H-thiochromeno[2,3-b]pyridine-3-carbonitrile trifluoroacetate | 273 |
| 65 | 2,4-diamino-9-fluoro-5H-thiochromeno[2,3-b]pyridine-3-carbonitrile 10,10-dioxide | 305 |

EXAMPLES 66–81

This illustrates the production of certain aminocyanopyridine compounds of the present invention.

General Procedure for the N-Alkylation:

To a solution of 2,4-diamino-7,8-dimethoxy-5H-chromeno[2,3-b]pyridine-3-carbonitrile (1.34 mmol) and the corresponding halide (2.01 mmol) in dimethylformamide (5 mL) is added sodium hydride (80 mg, 2.01 mmol). The reaction mixture is stirred at room temperature or heated to 40° C. until completion. The mixture is quenched with saturated aqueous ammonium chloride and directly purified by purified by reverse phase chromatography. Both the mono alkylated and dialkylated product were isolated.

The following compounds were prepared using the procedure described above:

Example 66: 2-amino-4-{[2-(dimethylamino)ethyl]amino}-7,8-dimethoxy-5H-chromeno[2,3-b]pyridine-3-carbonitrile, Example 67: 2,4-bis{[2-(dimethylamino)ethyl]amino}-7,8-dimethoxy-5H-chromeno[2,3-b]pyridine-3-carbonitrile, Example 68: 2-amino-4-[(2-aminoethyl)amino]-7,8-dimethoxy-5H-chromeno[2,3-b]pyridine-3-carbonitrile, Example 69: 2-amino-4-{[2-(1,3-dioxo-1,3-dihydro-2H-isoindol-2-yl)ethyl]amino}-7,8-dimethoxy-5H-chromeno[2,3-b]pyridine-3-carbonitrile, Example 70: 2-amino-7,8-dimethoxy-4-[(2-pyrrolidin-1-ylethyl)amino]-5H-chromeno[2,3-b]pyridine-3-carbonitrile, Example 71: 7,8-dimethoxy-2,4-bis[(2-pyrrolidin-1-ylethyl)amino]-5H-chromeno[2,3-b]pyridine-3-carbonitrile, Example 72: 2,4-bis(glycinyl)-7,8-dimethoxy-5H-chromeno[2,3-b]pyridine-3-carbonitrile trifluoroacetate, Example 73: N-(2-amino-3-cyano-7,8-dimethoxy-5H-chromeno[2,3-b]pyridin-4-yl)glycine, Example 74: 7,8-dimethoxy-2,4-bis[(2-methoxyethyl)amino]-5H-chromeno[2,3-b]pyridine-3-carbonitrile, Example 75: 2-amino-7,8-dimethoxy-4-[(2-methoxyethyl)amino]-5H-chromeno[2,3-b]pyridine-3-carbonitrile, Example 76: 2,4-bis(butylamino)-7,8-dimethoxy-5H-chromeno[2,3-b]pyridine-3-carbonitrile Example 77: 2-amino-4-(butylamino)-7,8-dimethoxy-5H-chromeno[2,3-b]pyridine-3-carbonitrile, Example 78: 7,8-dimethoxy-2,4-bis(propylamino)-5H-chromeno[2,3-b]pyridine-3-carbonitrile, Example 79: 2-amino-7,8-dimethoxy-4-(propylamino)-5H-chromeno[2,3-b]pyridine-3-carbonitrile, Example 80: 2,4-bis(ethylamino)-7,8-dimethoxy-5H-chromeno[2,3-b]pyridine-3-carbonitrile, and Example 81: 2-amino-4-(ethylamino)-7,8-dimethoxy-5H-chromeno[2,3-b]pyridine-3-carbonitrile.

General Procedure for the Demethylation:

To a solution of the corresponding dimethoxy aryl analog (0.68 mmol) in dichloromethane (2 mL) is slowly added boron tribromide (1 M, dichloromethane, 3.38 mmol, 3.38 mL). The reaction mixture is stirred at room temperature for 4 hours, quenched with 5% aqueous sodium hydroxide, then neutralized with 5% aqueous HCl. The resulting solid is collected and the aqueous layer is extracted with dichloromethane. The organic layer is concentrated under vacuum and combined with the solid. The residue is purified by reverse phase chromatography.

EXAMPLE 82

This illustrates the production of 2-amino-4-(ethylamino)-7,8-dihydroxy-5H-chromeno[2,3-b]pyridine-3-carbonitrile.

2-amino-4-(ethylamino)-7,8-dihydroxy-5H-chromeno[2,3-b]pyridine-3-carbonitrile was prepared using the demethylation procedure described above starting with 2-amino-4-(ethylamino)-7,8-dimethoxy-5H-chromeno[2,3-b]pyridine-3-carbonitrile. $^1$H NMR (400 MHz, DMSO) δ 6.5(s, 1H), 6.4 (s, 1H), 3.65(q, 2H), 2.5 (s, 2H), 1.25 (t, 3H); m/z 299.15 (M+H); HRMS (M+H) calculated for $C_{15}H_{15}N_4O_3$ 299.1139, found 299.1113.

EXAMPLE 83

This illustrates the production of 2-amino-7,8-dihydroxy-4-(propylamino)-5H-chromeno[2,3-b]pyridine-3-carbonitrile.

2-amino-7,8-dihydroxy-4-(propylamino)-5H-chromeno[2,3-b]pyridine-3-carbonitrile is prepared using the demethylation procedure described above for Examples 66–81 starting with 2-amino-7,8-dimethoxy-4-(propylamino)-5H-chromeno[2,3-b]pyridine-3-carbonitrile. $^1$H NMR (400 MHz, DMSO) δ 6.5(s, 1H), 6.4 (s, 1H), 3.55(m, 2H), 2.5 (s, 2H), 1.6(m, 2H), 1.35 (t, 3H); m/z 313.16 (M+H); HRMS (M+H) calculated for $C_{16}H_{17}N_4O_3$ 313.1295, found 313.1325.

EXAMPLE 84

This illustrates the production of 2-amino-7,8-dihydroxy-4-[(2-hydroxyethyl)amino]-5H-chromeno[2,3-b]pyridine-3-carbonitrile.

2-amino-7,8-dihydroxy-4-[(2-hydroxyethyl)amino]-5H-chromeno[2,3-b]pyridine-3-carbonitrile was prepared using the demethylation procedure described above for Examples 66–81, starting with 2-amino-7,8-dimethoxy-4-[(2-methoxyethyl)amino]-5H-chromeno[2,3-b]pyridine-3-carbonitrile. $^1$H NMR (400 MHz, DMSO) δ 6.5(s, 1H), 6.4 (s, 1H), 3.65(m, 2H), 3.55(m, 2H), 2.5 (s, 2H); m/z 315.13 (M+H).

EXAMPLE 85

This illustrates the production of 2,4-bis(ethylamino)-7,8-dihydroxy-5H-chromeno[2,3-b]pyridine-3-carbonitrile.

2,4-bis(ethylamino)-7,8-dihydroxy-5H-chromeno[2,3-b]pyridine-3-carbonitrile was prepared by using the procedure described in Examples 66–81.

EXAMPLES 86–91

This illustrates the production of certain aminocyanopyridine compounds of the present invention.

General Procedure for the O-Alkylation of Phenol 2,4-diamino-9-hydroxy-5H-chromeno[2,3-b]pyridine-3-carbonitrile:

A solution of 2,4-diamino-9-hydroxy-5H-chromeno[2,3-b]pyridine-3-carbonitrile (0.73 mmol), and powdered sodium hydroxide (117 mg, 2.93 mmol)) in dimethyl sulfoxide (4 mL) is heated to 50° C. for five minutes. The corresponding halide is added and the reaction mixture is stirred at 50° C. or 75° C. until completion. The mixture is quenched with saturated aqueous ammonium chloride and directly purified by purified by reverse phase chromatography.

The following compounds were prepared using the above procedure:

Example 86: 2,4-diamino-9-(2-aminoethoxy)-5H-chromeno[2,3-b]pyridine-3-carbonitrile, Example 87: (2,4-diamino-3-cyano-5H-chromeno[2,3-b]pyridin-9-yl)oxy]acetic acid, Example 88: 2,4-diamino-9-(2-hydroxyethoxy)-5H-chromeno[2,3-b]pyridine-3-carbonitrile, Example 89: 2,4-diamino-9-[2-(dimethylamino)ethoxy]-5H-chromeno[2,3-b]pyridine-3-carbonitrile, Example 90: 2,4-diamino-9-(pyridin-4-ylmethoxy)-5H-chromeno[2,3-b]pyridine-3-carbonitrile, and Example 91: 2,4-diamino-9-(2-pyrrolidin-1-ylethoxy)-5H-chromeno[2,3-b]pyridine-3-carbonitrile.

EXAMPLES 92–120

This illustrates the production of certain aminocyanopyridine compounds of the present invention.

General Procedure for the Mannich Condensation:

To a solution of the corresponding phenol (0.92 mmol) in ethanol (5 mL) is added formic acid (37% solution, 76 μL, 1.01 mmol) and piperidine (100 μL, 1.01 mmol). The reaction mixture is stirred at 75° C. until completion. The mixture is quenched with saturated aqueous ammonium chloride and directly purified by purified by reverse phase chromatography and each regioisomer isolated.

The following compounds were prepared using the above procedure:

Example 92: 2,4-diamino-9-hydroxy-6,8-bis(piperidin-1-ylmethyl)-5H-chromeno[2,3-b]pyridine-3-carbonitrile, and Example 93: 2,4-diamino-9-hydroxy-8-(piperidin-1-ylmethyl)-5H-chromeno[2,3-b]pyridine-3-carbonitrile, were produced starting with 2,4-diamino-9-hydroxy-5H-chromeno[2,3-b]pyridine-3-carbonitrile, produced as described in Examples 66–81, and Example 94: 2,4-diamino-8-hydroxy-7,9-bis(piperidin-1-ylmethyl)-5H-chromeno[2,3-b]pyridine-3-carbonitrile, was produced starting with 2,4-diamino-8-hydroxy-5H-chromeno[2,3-b]pyridine-3-carbonitrile, produced as described in Example 8.

Other aminocyanopyridine compounds of the present invention can be produced by the same general method, and are shown in the table below along with NMR parameters, which were determined as described above.

| Ex. No. | Compound name | m/z (M + H) | HRMS Theor. | HRMS Found | Formula Calcd for |
|---|---|---|---|---|---|
| 95 | 2,4-diamino-9-hydroxy-8-(piperidin-1-ylmethyl)-5H-chromeno[2,3-b]pyridine-3-carbonitrile trifluoroacetate | 352.26 | 352.1768 | 352.1778 | $C_{19}H_{21}N_5O_2$ |
| 96 | 2,4-diamino-8-hydroxy-7,9-bis(piperidin-1-ylmethyl)-5H-chromeno[2,3-b]pyridine-3-carbonitrile trifluoroacetate | 449.33 | 449.266 | 449.2637 | $C_{25}H_{32}N_6O_2$ |
| 97 | 2,4-diamino-9-hydroxy-6,8-bis(piperidin-1-ylmethyl)-5H-chromeno[2,3-b]pyridine-3-carbonitrile trifluoroacetate | 449.32 | 449.266 | 449.2629 | $C_{25}H_{32}N_6O_2$ |
| 98 | 2,4-diamino-9-(2-pyrrolidin-1-ylethoxy)-5H-chromeno[2,3-b]pyridine-3-carbonitrile trifluoroacetate | 352.26 | 352.1768 | 352.1777 | $C_{19}H_{21}N_5O_2$ |
| 99 | 2,4-diamino-9-(pyridin-4-ylmethoxy)-5H-chromeno[2,3-b]pyridine-3-carbonitrile trifluoroacetate | 346.16 | 346.1299 | 346.1344 | $C_{19}H_{15}N_5O_2$ |
| 100 | 2,4-diamino-9-[2-(dimethylamino)ethoxy]-5H-chromeno[2,3-b]pyridine-3-carbonitrile trifluoroacetate | 326.24 | 326.1612 | 326.1607 | $C_{17}H_{19}N_5O_2$ |
| 101 | 2,4-diamino-9-(2-hydroxyethoxy)-5H-chromeno[2,3-b]pyridine-3-carbonitrile trifluoroacetate | 299.19 | 299.1139 | 299.1153 | $C_{15}H_{14}N_4O_3$ |
| 102 | [(2,4-diamino-3-cyano-5H-chromeno[2,3-b]pyridin-9-yl)oxy]acetic acid trifluoroacetate | 313.14 | 313.0931 | 313.0972 | $C_{15}H_{12}N_4O_4$ |
| 103 | 2,4-diamino-9-(2-aminoethoxy)-5H-chromeno[2,3-b]pyridine-3-carbonitrile trifluoroacetate | 298.18 | 298.1299 | 298.1303 | $C_{15}H_{15}N_5O_2$ |
| 104 | 2,4-bis(ethylamino)-7,8-dihydroxy-5H-chromeno[2,3-b]pyridine-3-carbonitrile trifluoroacetate | 327.2 | 327.1452 | 327.1493 | $C_{17}H_{18}N_4O_3$ |
| 105 | 2-amino-4-{[2-(dimethylamino)ethyl]amino}-7,8-dimethoxy-5H-chromeno[2,3-b]pyridine-3-carbonitrile trifluoroacetate | 370.27 | 370.1874 | 370.1869 | $C_{19}H_{23}N_5O_3$ |
| 106 | 2,4-bis{[2-(dimethylamino)ethyl]amino}-7,8-dimethoxy-5H-chromeno[2,3-b]pyridine-3-carbonitrile trifluoroacetate | 441.31 | 441.2609 | 411.2629 | $C_{23}H_{32}N_6O_3$ |
| 107 | 2-amino-4-[(2-aminoethyl)amino]-7,8-dimethoxy-5H-chromeno[2,3-b]pyridine-3-carbonitrile trifluoroacetate | 342.22 | 342.1561 | 342.1546 | $C_{17}H_{19}N_5O_3$ |
| 108 | 2-amino-4-{[2-(1,3-dioxo-1,3-dihydro-2H-isoindol-2-yl)ethyl]amino}-7,8-dimethoxy-5H-chromeno[2,3-b]pyridine-3-carbonitrile trifluoroacetate | 472.21 | | | $C_{25}H_{21}N_5O_5$ |
| 109 | 2-amino-7,8-dimethoxy-4-[(2-pyrrolidin-1-ylethyl)amino]-5H-chromeno[2,3-b]pyridine-3-carbonitrile | 396.32 | 396.203 | 396.2061 | $C_{21}H_{25}N_5O_3$ |
| 110 | 7,8-dimethoxy-2,4-bis[(2-pyrrolidin-1-ylethyl)amino]-5H-chromeno[2,3-b]pyridine-3-carbonitrile | 493.44 | | | $C_{27}H_{36}N_6O_3$ |
| 111 | 2,4-bis(glycinyl)-7,8-dimethoxy-5H-chromeno[2,3-b]pyridine-3-carbonitrile trifluoroacetate | 415.33 | | | $C_{19}H_{18}N_4O_7$ |
| 112 | N-(2-amino-3-cyano-7,8-dimethoxy-5H-chromeno[2,3-b]pyridin-4-yl)glycine | 357.26 | 357.1193 | 357.1818 | $C_{17}H_{16}N_4O_5$ |
| 113 | 7,8-dimethoxy-2,4-bis[(2-methoxyethyl)amino]-5H-chromeno[2,3-b]pyridine-3-carbonitrile | 415.3 | 415.1976 | 415.1972 | $C_{21}H_{26}N_4O_5$ |
| 114 | 2-amino-7,8-dimethoxy-4-[(2-methoxyethyl)amino]-5H-chromeno[2,3-b]pyridine-3-carbonitrile | 357.25 | 357.1557 | 357.2538 | $C_{18}H_{20}N_4O_4$ |

-continued

| Ex. No. | Compound name | m/z (M + H) | HRMS Theor. | HRMS Found | Formula Calcd for |
|---|---|---|---|---|---|
| 115 | 2,4-bis(butylamino)-7,8-dimethoxy-5H-chromeno[2,3-b]pyridine-3-carbonitrile | 411.35 | 411.2391 | 411.2391 | $C_{23}H_{30}N_4O_3$ |
| 116 | 2-amino-4-(butylamino)-7,8-dimethoxy-5H-chromeno[2,3-b]pyridine-3-carbonitrile | 355.26 | 355.1765 | 355.1763 | $C_{19}H_{22}N_4O_3$ |
| 117 | 7,8-dimethoxy-2,4-bis(propylamino)-5H-chromeno[2,3-b]pyridine-3-carbonitrile | 383.31 | 383.2078 | 383.2085 | $C_{21}H_{26}N_4O_3$ |
| 118 | 2-amino-7,8-dimethoxy-4-(propylamino)-5H-chromeno[2,3-b]pyridine-3-carbonitrile | 341.25 | 341.1608 | 341.1623 | $C_{18}H_{20}N_4O_3$ |
| 119 | 2,4-bis(ethylamino)-7,8-dimethoxy-5H-chromeno[2,3-b]pyridine-3-carbonitrile | 355.27 | 355.1765 | 355.1784 | $C_{19}H_{22}N_4O_3$ |
| 120 | 2-amino-4-(ethylamino)-7,8-dimethoxy-5H-chromeno[2,3-b]pyridine-3-carbonitrile | 327.21 | 327.1452 | 327.142 | $C_{17}H_{18}N_4O_3$ |

EXAMPLE 121

This illustrates the production of 2,4-diamino-7,8-dimethoxy-5H-chromeno[2,3-b]pyridine-3-carbonitrile.

To a stirred solution of 3,4-dimethoxyphenol (35.7 mmol, 5.5 g) and piperidine (40 mmol, 3.4 g) in ethanol (50 mL) was slowly added formaldehyde (37%, water, 39.5 mmol, 3.2 g). The mixture was stirred at room temperature for 4 hours and then evaporated in vacuo and the resultant residue was partitioned between ethyl acetate (100 mL) and water (100 mL). The organic layer was washed with water, dried (MgSO$_4$) and evaporated to give a colorless oily residue. To a solution of the above oily product in acetone was added methyl iodide (100 mmol, 14.2 g) and the mixture was stirred at room temperature overnight. The resultant white precipitate was collected by filtration, washed with ether and air-dried to give 8.14 g of a white solid.

To a slurry of the above solid (1 mmol, 390 mg) and 2-amino-1-propene-1,1,3-tricarbonitrile (1 mmol, 132 mg) in ethanol (10 mL) was added triethylamine (0.5 mL) and the resultant solution was heated at reflux for 30 minutes. After cooling to room temperature, the precipitate was collected by filtration, washed with ethanol and air-dried to give the product as a white solid (178 mg, 60% yield). $^1$H NMR (400 MHZ, DMSO) δ 6.582 (s, 1H), 6.574 (s, 1H), 6.406 (s, 2H), 6.241 (s, 2H), 3.686 (s, 3H), 3.671 (s, 3H), 3.524 (s, 2H); m/z 299 (M+H).

EXAMPLE 122

This illustrates the production of 2(2,4-diamino-3-cyano-8-methoxy-5H-chromeno[2,3-b]pyridin-5-yl)malononitrile.

To a solution of 2-hydroxy-4-methoxybenzaldehyde (10 mmol, 1.52 g) and malononitrile (40 mmol, 2.64 g) in ethanol (250 mL) was added six drops of piperidine. The mixture was heated at 50° C. for 10 minutes and then stirred at room temperature for 5 hours. The resultant precipitate was collected by filtration and recrystallized from methanol to give the product as a pale yellow solid (1.19 g, 36% yield). $^1$H NMR (400 MHz, DMSO) δ 7.274(d, 1H), 6.999 (s, 2H), 6.817 (dd, 1H), 6.733 (d, 1H), 6.619 (s, 2H), 4.804 (d, 1H), 4.734 (d, 1H), 3.757 (s, 3H); m/z 333 (M+H).

EXAMPLE 123

This illustrates the production of 2(2,4-diamino-3-cyano-7-bromo-5H-chromeno[2,3-b]pyridin-5-yl)malononitrile.

To a solution of 5-bromo-2-hydroxybenzaldehyde (10 mmol, 2 g) and malononitrile (35 mmol, 2.31 g) in ethanol (200 mL) was added six drops of piperidine and the mixture was stirred at room temperature for 30 hours. The resultant precipitate was collected by filtration and recrystallized from methanol to give the product as a white solid (1.68 g, 44% yield). $^1$H NMR (400 MHz, DMSO) δ 7.489 (dd, 1H), 7.344 (d, 1H), 7.230 (d, 1H), 7.063 (s, 2H), 6.686 (s, 2H), 4.876 (d, 1H), 4.850 (d, 1H); m/z 381, 383 (M+H).

EXAMPLE 124

This illustrates the production of 2(2,4-diamino-3-cyano-7-methoxy-5H-chromeno[2,3-b]pyridin-5-yl)malononitrile.

To a solution of 2-hydroxy-5-methoxybenzaldehyde (10 mmol, 1.52 g) and malononitrile (40 mmol, 2.64 g) in ethanol (350 mL) was added six drops of piperidine and the mixture was stirred at room temperature for 18 hours. The resultant precipitate was collected by filtration, successively washed with ethanol and ether and and air-dried to give the product as a grey solid (1.42 g, 43% yield). $^1$H NMR (400 MHz, DMSO) δ 7.107(d, 1H), 6.990 (m, 3H), 6.865 (d, 1H), 6.603 (s, 2H), 4.850 (d, 1H), 4.794 (d, 1H), 3.724 (s, 3H); m/z 333 (M+H).

EXAMPLE 125

This illustrates the production of 2(2,4-diamino-3-cyano-8-hydroxy-5H-chromeno[2,3-b]pyridin-5-yl)malononitrile.

To a solution of 2,4-dihydroxybenzaldehyde (10 mmol, 1.38 g) and malononitrile (40 mmol, 2.64 g) in ethanol (350 mL) was added six drops of piperidine and the mixture was stirred at room temperature for 5 hours. The resultant precipitate was collected by filtration, washed successively with ethanol and ether and air-dried to give the product as a yellow solid (1.62 g, 51% yield). $^1$H NMR (400 MHz, DMSO) δ 9.887 (s, 1H), 7.162 (d, 1H), 6.971 (s, 2H), 6.613 (dd, 1H), 6.597 (s, 2H), 6.497 (d, 1H), 4.743 (d, 1H), 4.687 (d, 1H); m/z 319 (M+H).

EXAMPLE 126–135

This illustrates the production of certain aminocyanopyridine compounds of the present invention.

The aminocyanopyridine compounds listed in the table below were produced according to the general method described in Example 123. NMR analysis was carried out for each material according to the method described above. The names and NMR data for each compound is provided in the table.

| Ex. No. | Compound name | m/z (M + H) |
|---|---|---|
| 126 | 2,4-diamino-7-methoxy-5H-chromeno[2,3-b]pyridine-3-carbonitrile | 269 |
| 127 | 2(2,4-diamino-3-cyano-7-hydroxy-5H-chromeno[2,3-b]pyridin-5-yl)malononitrile | 319 |
| 128 | 2,4-diamino-7-bromo-5H-chromeno[2,3-b]pyridine-3-carbonitrile | 317, 319 |
| 129 | 2(2,4-diamino-3-cyano-9-methoxy-5H-chromeno[2,3-b]pyridin-5-yl)malononitrile | 333 |
| 130 | 2,4-diamino-5-(2-fluoro-phenyl)-8-methoxy-5H-chromeno[2,3-b]pyridine-3-carbonitrile | 363 |
| 131 | 2(2,4-diamino-3-cyano-7-chloro-5H-chromeno[2,3-b]pyridin-5-yl)malononitrile | 337 |
| 132 | 2,4-diamino-5-phenyl-8-hydroxy-5H-chromeno[2,3-b]pyridine-3-carbonitrile | 331 |
| 133 | 2,4-diamino-5-(3-fluoro-phenyl)-8-methoxy-5H-chromeno[2,3-b]pyridine-3-carbonitrile | 363 |
| 134 | 2,4-diamino-7-bromo-8-methoxy-5H-chromeno[2,3-b]pyridine-3-carbonitrile | 347, 349 |
| 135 | 2,4-diamino-5-phenyl-8-methoxy-5H-chromeno[2,3-b]pyridine-3-carbonitrile | 345 |

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions without departing from the scope of the invention, it is intended that all matter contained in the above description shall be interpreted as illustrative and not in a limiting sense.

What is claimed is:

1. A method of making a tricyclic aminocyanopyridine compound, the method comprising:

reacting a substituted benzaldehyde having the structure:

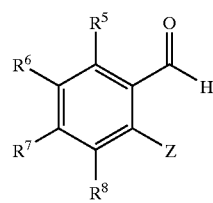

with a tricarbonitrile having the structure:

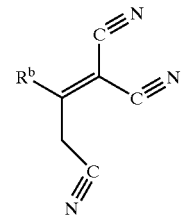

to form an aminocyanopyridine compound having the structure:

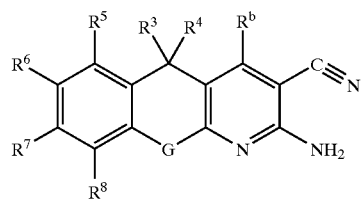

wherein:
Z is selected from the group consisting of —OH, —SH, and —NR$^a$Y;
R$^a$ is selected from the group consisting of alkyl, aryl, and heteroaryl;
Y is a protecting group for nitrogen that is selected from the group consisting of benzyl, allyl, alkyl carbamates and benzyl carbamate;
G is selected from the group consisting of oxygen, sulfur, and nitrogen;
when G is oxygen, it is unsubstituted;
when G is sulfur, it is either unsubstituted or is substituted with one or two oxo groups;
when G is nitrogen, it is substituted with $C_1$–$C_4$ alkyl;
R$^b$ is selected from the group consisting of furyl and —NH—R$^2$;

R² is selected from the group consisting of hydrogen, alkyl, alkenyl, alkynyl, alkoxy, hydroxyalkyl, alkylaryl, arylalkyl, alkoxyaryl, aminoalkyl, alkylaminoalkyl, arylaminoalkyl, alkoxyalkyl, alkylcarboxy, and carboxyalkyl;

R³ and R⁴ are each independently selected from the group consisting of hydrogen, dicyanoalkyl, and substituted or unsubstituted heterocyclyl and cyclyl, where substituents, if any, comprise halo moieties; and R⁵, R⁶, R⁷ and R⁸ are each independently selected from the group consisting of hydrogen, hydroxy, alkoxy, halo, alkyl, alkenyl, alkylyl, arylalkyl, alkylaryl, amino, alkylamino, arylamino, alkylaminoalkyl, carboxy, aminoalkoxy, alkylcarboxyalkyl, alkylamino, aminoalkyl, nitro, aryl, arylamino, alkenoxy, hydroxyalkoxy, alkoxyalkoxy, heterocyclylalkyl, heterocyclylalkoxy, carboxyalkoxy, alkylaminoalkoxy, alkylcarboxyalkoxy, pyrrolidylethoxy, hydroxyalkoxy, and alkylcarboxy, where R⁶ and R⁷ are such that they optionally join to form a six membered heterocyclic ring.

2. The method according to claim 1, wherein:

R² is selected from the group consisting of hydrogen, alkyl, alkenyl, alkynyl, alkoxy, hydroxyalkyl, alkylaryl, arylalkyl, alkoxyaryl, aminoalkyl, alkylaminoalkyl, arylaminoalkyl, alkoxyalkyl, alkylcarboxy, and carboxyalkyl;

R³ and R⁴ are each independently selected from the group consisting of hydrogen, dicyanoalkyl, and substituted or unsubstituted heterocyclyl and cyclyl, where substituents, if any, comprise halo moieties;

R⁵ is selected from the group consisting of hydrogen, alkoxy, halo, alkyl, alkenyl, alkylyl, arylalkyl, or alkylaryl;

R⁶ is selected from the group consisting of hydrogen, hydroxy, alkoxy, alkyl, alkenyl, alkynyl, amino, alkylamino, arylamino, alkylaminoalkyl, carboxy, aminoalkoxy, halo, alkylcarboxyalkyl, alkylamino, aminoalkyl, nitro, aryl, arylalkyl, alkylaryl, or arylamino;

R⁷ is selected from the group consisting of hydrogen, hydroxy, alkoxy, alkenoxy, hydroxyalkoxy, alkoxyalkoxy, aminoalkoxy, heterocyclylalkyl, heterocyclylalkoxy, carboxyalkoxy, alkylaminoalkoxy, and alkylcarboxyalkoxy;

where the R⁶ and R⁷ groups can join to form a six membered heterocyclic ring; and R⁸ is selected from the group consisting of hydrogen, hydroxy, halo, nitro, amino, alkyl, alkoxy, heterocyclylalkoxy, carboxyalkoxy, pyrrolidylethoxy, carboxymethoxy, hydroxyalkoxy, aminoalkoxy, alkylcarboxy, alkylaminoalkyl, carboxy, and heterocyclylalkyl.

3. The method according to claim 1, wherein the reacting step comprises heating the substituted benzaldehyde and the tricarbonitrile in a mixture of ethanol and acetic acid.

4. The method according to claim 3, wherein the mixture is heated to reflux temperature at atmospheric pressure.

5. The method according to claim 4, further comprising recovering the aminocyanopyridine compound.

6. The method according to claim 5, wherein the recovering step comprises concentrating the reaction product of the substituted benzaldehyde and the tricarbonitrile under vacuum; mixing the concentrated reaction product with trifluoroacetic acid; adding triethylsilane to the mixture of concentrated reaction product and trifluoroacetic acid; adding dichloromethane to the mixture of concentrated reaction product and trifluoroacetic acid; and collecting solids comprising the aminocyanopyridine compound.

7. The method according to claim 6, wherein the triethylsilane is added to the concentrated reaction product while the mixture is being stirred at 0° C. for about 1 hour.

8. The method according to claim 6, wherein the solids are collected by filtration and further comprising washing the solids with dichloromethane and ether.

9. The method according to claim 1, wherein the substituted benzaldehyde comprises salicaldehyde and the tricarbonitrile comprises 2-amino-1-propene-1,1,3-tricarbonitrile.

10. The method according to claim 1, wherein Y comprises tert-butylcarbamate.

11. A method of making a tricyclic aminocyanopyridine compound, the method comprising:

reacting a substituted benzaldehyde having the structure:

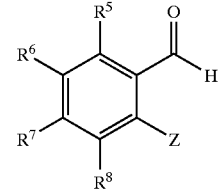

with a tricarbonitrile having the structure:

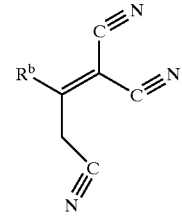

to form an aminocyanopyridine compound having the structure:

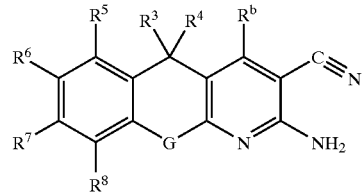

wherein:

Z is selected from the group consisting of —OH, —SH, and —NRᵃY;

Rᵃ is selected from the group consisting of alkyl, aryl, and heteroaryl;

Y is a protecting group for nitrogen that is selected from the group consisting of benzyl, allyl, alkyl carbamates and benzyl carbamate;

G is selected from the group consisting of oxygen, sulfur, and nitrogen;

when G is oxygen, it is unsubstituted;

when G is sulfur, it is either unsubstituted or is substituted with one or two oxo groups;

when G is nitrogen, it is substituted with $C_1$–$C_4$ alkyl;

Rᵇ is selected from the group consisting of furyl and —NH—R²;

$R^2$ is selected from the group consisting of hydrogen, alkyl, alkenyl, alkynyl, alkoxy, hydroxyalkyl, alkylaryl, arylalkyl, alkoxyaryl, aminoalkyl, alkylaminoalkyl, arylaminoalkyl, alkoxyalkyl, alkylcarboxy, and carboxyalkyl;

$R^3$ and $R^4$ are each independently selected from the group consisting of hydrogen, dicyanoalkyl, and substituted or unsubstituted heterocyclyl and cyclyl, where substituents, if any, comprise halo moieties; and $R^5$, $R^6$, $R^7$ and $R^8$ are each independently selected from the group consisting of:

hydrogen, hydroxy, amino, halo, nitro, branched or unbranched $C_1$–$C_6$ alkyl, $C_2$–$C_6$ alkenyl, $C_2$–$C_6$ alkynyl, $C_1$–$C_6$ alkoxy, hydroxy $C_1$–$C_6$ alkyl, hydroxy $C_1$–$C_6$ alkoxy, $C_1$–$C_6$ alkoxy $C_1$–$C_6$ alkoxy, $C_1$–$C_6$ alkoxy $C_1$–$C_6$ alkyl, $C_2$–$C_6$ alkenoxy, branched or unbranched amino $C_1$–$C_6$ alkyl, diamino $C_2$–$C_6$ alkyl, $C_1$–$C_6$ alkylamino $C_1$–$C_6$ alkyl, $C_1$–$C_6$ alkylamino, di-($C_1$–$C_6$ alkyl)amino, $C_1$–$C_4$ alkoxyarylamino, $C_1$–$C_4$alkoxyalkylamino, amino $C_1$–$C_6$ alkoxy, di-($C_1$–$C_4$alkylamino, $C_2$–$C_6$ alkoxy, di-($C_1$–$C_6$ alkyl)amino $C_1$–$C_6$ alkyl, $C_1$–$C_6$ alkylamino $C_1$–$C_6$ alkoxy, halo $C_1$–$C_6$ alkoxy, dihalo $C_1$–$C_6$ alkoxy, trihalo $C_1$–$C_6$alkoxy, cyano $C_1$–$C_6$ alkyl, dicyano $C_1$–$C_6$ alkyl, cyano $C_1$–$C_6$ alkoxy, dicyano $C_1$–$C_6$ alkoxy, carbamyl $C_1$–$C_4$ alkoxy, heterocyclyl $C_1$–$C_4$ alkoxy, heteroaryl $C_1$–$C_4$ alkoxy, sulfo, sulfamyl, $C_1$–$C_4$ alkylaminosulfonyl, hydroxy $C_1$–$C_4$ alkylaminosulfonyl, di-($C_1$–$C_4$ alkyl)aminosulfonyl, $C_1$–$C_4$ alkylthio, $C_1$–$C_4$ alkylsulfonyl, $C_1$–$C_4$ alkylsulfinyl, aryl, aryl $C_1$–$C_6$ alkyl, heterocyclyl $C_1$–$C_6$ alkyl, heteroaryl $C_1$–$C_6$ alkyl, heterocyclyl $C_1$–$C_6$ alkoxy, heteroaryl $C_1$–$C_6$ alkoxy, aryl $C_1$–$C_6$ alkoxy, where the aryl ring can be substituted or unsubstituted, and, if substituted, the substituent group is selected from one or more of the group consisting of $C_1$–$C_6$ alkyl, halo, amino, and $C_1$–$C_6$ alkoxy, substituted or unsubstituted $C_3$–$C_6$ cyclyl, $C_3$–$C_6$ heterocyclyl, and, if substituted, the substituent group is selected from one or more of the group consisting of $C_1$–$C_6$ alkyl, $C_1$–$C_6$ alkoxy, halo, amino, and where the $C_3$–$C_6$ heterocyclyl ring contains O, S, or N, branched or unbranched $C_1$–$C_6$ alkoxycarbonyl $C_1$–$C_6$ alkoxy, and carboxy, carboxy $C_1$–$C_6$ alkoxy, carboxy $C_1$–$C_6$ alkyl, hydroxy $C_1$–$C_4$ alkoxycarbonyl, $C_1$–$C_4$ alkoxycarbonyl.

12. The method according to claim 11, wherein:

$R^1$ is selected from the group consisting of hydrogen, branched or unbranched alkyl, alkenyl, alkynyl, alkoxy, alkylaryl, arylalkyl, carboxy, carboxyalkyl, hydroxyalkyl, alkylcarboxy, aryl, amino, aminoalkyl, alkylamino, halo, alkylaminoalkyl, alkoxy, alkoxyalkyl, monocyclyl, bicyclyl, polycyclyl, and heterocyclyl;

$R^2$ is selected from the group consisting of hydrogen, alkyl, alkenyl, alkynyl, alkoxy, hydroxyalkyl, alkylaryl, arylalkyl, alkoxyaryl, aminoalkyl, alkylaminoalkyl, arylaminoalkyl, alkoxyalkyl, alkylcarboxy, and carboxyalkyl;

$R^3$ is selected from the group consisting of hydrogen, dicyanoalkyl, and substituted or unsubstituted heterocyclyl and cyclyl, where substituents, if any, comprise halo moieties;

$R^4$ is selected from the group consisting of hydrogen, dicyanoalkyl, and substituted or unsubstituted heterocyclyl and cyclyl, where substituents, if any, comprise halo moieties;

$R^5$ is selected from the group consisting of hydrogen, alkoxy, halo, alkyl, alkenyl, alkylyl, arylalkyl, or alkylaryl;

$R^6$ is selected from the group consisting of hydrogen, hydroxy, alkoxy, alkyl, alkenyl, alkynyl, amino, alkylamino, arylamino, alkylaminoalkyl, carboxy, aminoalkoxy, halo, alkylcarboxyalkyl, alkylamino, aminoalkyl, nitro, aryl, arylalkyl, alkylaryl, or arylamino;

$R^7$ is selected from the group consisting of hydrogen, hydroxy, alkoxy, alkenoxy, hydroxyalkoxy, alkoxyalkoxy, aminoalkoxy, heterocyclylalkyl, heterocyclylalkoxy, carboxyalkoxy, alkylaminoalkoxy, and alkylcarboxyalkoxy;

where the $R^6$ and $R^7$ groups can join to form a six membered heterocyclic ring;

$R^8$ is selected from the group consisting of hydrogen, hydroxy, halo, nitro, amino, alkyl, alkoxy, heterocyclylalkoxy, carboxyalkoxy, pyrrolidylethoxy, carboxymethoxy; hydroxyalkoxy, aminoalkoxy, alkylcarboxy, alkylaminoalkyl, carboxy, and heterocyclylalkyl; and G is selected from the group consisting of oxygen, sulfur, and nitrogen;

when G is oxygen, it is unsubstituted;

when G is sulfur, it is unsubstituted or it is substituted with one or two oxo groups;

when G is nitrogen, it is substituted with $C_1$–$C_4$-alkyl.

13. The method according to claim 11, wherein:

$R^1$ is selected from the group consisting of hydrogen, ethyl, dimethylaminoethyl, butyl, propyl, methoxyethyl, tetramethylaminoethyl, and carboxymethyl;

$R^2$ is selected from the group consisting of hydrogen, hydroxyethyl, propyl, ethyl, methyl, 4-methoxyphenyl, ethoxyethyl, aminoethyl, phenylmethyl, dimethylaminoethyl, phthaloaminoethyl, butyl, methoxyethyl, tetramethylaminoethyl, and carboxymethyl;

$R^3$ is selected from the group consisting of hydrogen, dicyanomethyl, 2-fluorophenyl, phenyl, and 3-fluorophenyl, $R^4$ is selected from the group consisting of hydrogen, dicyanomethyl, 2-fluorophenyl, phenyl, and 3-fluorophenyl;

$R^5$ is selected from the group consisting of hydrogen, hydroxy, methoxy, bromo, and 2-pyridomethyl;

$R^6$ is selected from the group consisting of hydrogen, hydroxy, methoxy, amino, carboxy, diaminoethoxy, bromo, propoxy, isobutylcarboxymethoxy, dimethylamino, nitro, phenyl, chloro, pyridylmethyl, and fluoro;

$R^7$ is selected from the group consisting of hydrogen, hydroxy, methoxy, hydroxyethoxy, ethoxyethoxy, ethoxy, aminoethoxy, morpholinoethoxy, carboxymethoxy, N-pyrrolidylethoxy, dimethylaminoethoxy, pyridylmethyl, 2-propenoxy, and isobutylcarboxymethoxy, where the $R^6$ and $R^7$ groups can join to form a six membered heterocyclic ring;

$R^8$ is selected from the group consisting of hydrogen, hydroxy, fluoro, methoxy, nitro, amino, pyrrolidylethoxy, carboxymethoxy, methyl, hydroxyethoxy, aminoethoxy, 4-pyridylmethoxy, isobutyl, ethylcarboxy, dimethylaminoethoxy, carboxy, bromo, and pyrridylmethyl; and G is selected from the group consisting of oxygen, sulfur, and nitrogen;

when G is oxygen, it is unsubstituted;

when G is sulfur, it is unsubstituted or it is substituted with one or two oxo groups;

when G is nitrogen, it is substituted with —$CH_3$.

14. The method according to claim 11, wherein:

$R^1$ is selected from the group consisting of hydrogen, and $C_1$–$C_2$ alky;

$R^2$ is selected from the group consisting of hydrogen, $C_1$–$C_3$ alkyl, hydroxy $C_1$–$C_2$ alkyl, $C_1$–$C_2$ alkoxyphenyl, $C_1$–$C_2$ alkoxy $C_1$–$C_2$ alkyl, amino $C_1$–$C_2$ alkyl, phenyl $C_1$–$C_2$ alkyl, and di $C_1$–$C_2$ alkylamino $C_1$–$C_2$ alkyl;

$R^3$ and $R^4$ are each independently selected from the group consisting of hydrogen, dicyano $C_1$–$C_2$ alkyl, and halophenyl;

$R^5$ is selected from the group consisting of hydrogen, and hydroxy;

$R^6$ is selected from the group consisting of hydrogen, hydroxy, $C_1$–$C_3$ alkoxy, amino, nitro, carboxy, diamino $C_1$–$C_2$ alkoxy, halo, propenoxy, iso $C_3$–$C_4$ alkylcarboxy $C_1$–$C_2$ alkoxy, di $C_1$–$C_2$ alkylamino, and phenyl;

$R^7$ is selected from the group consisting of hydrogen, hydroxy, $C_1$–$C_3$ alkoxy, hydroxy $C_1$–$C_2$ alkoxy, $C_1$–$C_2$ alkoxy $C_1$–$C_2$ alkoxy, amino $C_1$–$C_2$ alkoxy, morpholino $C_1$–$C_2$ alkoxy, carboxyl $C_1$–$C_2$ alkoxy, pyrrolidyl $C_1$–$C_2$ alkoxy, di $C_1$–$C_2$ alkylamino $C_1$–$C_2$ alkoxy, pyrrolidyl $C_1$–$C_2$ alkyl, iso $C_3$–$C_4$ alkylcarboxy $C_1$–$C_2$ alkoxy, and $_2$-propenoxy, where the $R^6$ and $R^7$ groups can join to form a six membered heterocyclic ring;

$R^8$ is selected from the group consisting of hydrogen, hydroxy, halo, $C_1$–$C_2$ alkyl, $C_1$–$C_2$ alkoxy, nitro, amino, pyrrolidyl $C_1$–$C_2$ alkoxy, carboxy $C_1$–$C_2$ alkoxy, hydroxy $C_1$–$C_2$ alkoxy, and amino $C_1$–$C_2$ alkoxy; and G is selected from the group consisting of oxygen and sulfur;

when G is sulfur, it is unsubstituted or is substituted with one or two oxo groups;

when G is oxygen, it is unsubstituted.

15. The method according to claim 11, wherein:

$R^1$ is hydrogen;

$R^2$ is selected from the group consisting of hydrogen, $C_1$–$C_3$ alkyl, hydroxy $C_1$–$C_2$ alkyl, $C_1$–$C_2$ alkoxyphenyl, $C_1$–$C_2$ alkoxy $C_1$–$C_2$ alkyl, amino $C_1$–$C_2$ alkyl, phenyl $C_1$–$C_2$ alkyl, and di $C_1$–$C_2$ alkylamino $C_1$–$C_2$ alkyl;

$R^3$ and $R^4$ are each independently selected from the group consisting of hydrogen, and dicyano $C_1$–$C_2$ alkyl;

$R^5$ is selected from the group consisting of hydrogen, and hydroxy;

$R^6$ is selected from the group consisting of hydrogen, hydroxy, $C_1$–$C_2$ alkoxy, amino, carboxy, nitro, diamino $C_1$–$C_2$ alkoxy, halo, 2-propenoxy, iso $C_3$–$C_4$ alkylcarboxy $C_1$–$C_2$ alkoxy, di $C_1$–$C_2$ alkylamino, and phenyl;

$R^7$ is selected from the group consisting of hydrogen, hydroxy, $C_1$–$C_2$ alkoxy, hydroxy $C_1$–$C_2$ alkoxy, $C_1$–$C_2$ alkoxy $C_1$–$C_2$ alkoxy, amino $C_1$–$C_2$ alkoxy, morpholino $C_1$–$C_2$ alkoxy, carboxyl $C_1$–$C_2$ alkoxy, pyrrolidyl $C_1$–$C_2$ alkoxy, di $C_1$–$C_2$ alkylamino $C_1$–$C_2$ alkoxy, pyrrolidyl $C_1$–$C_2$ alkyl, iso $C_3$–$C_4$ alkylcarboxy $C_1$–$C_2$ alkoxy, and 2-propenoxy;

wherein the $R^6$ and $R^7$ groups can join to form a six membered heterocyclic ring;

$R^8$ is selected from the group consisting of hydrogen, hydroxy, halo, $C_1$–$C_2$ alkoxy, nitro, amino, pyrrolidyl $C_1$–$C_2$ alkoxy, and carboxy $C_1$–$C_2$ alkoxy; and G is selected from the group consisting of oxygen and sulfur;

when G is sulfur, it is unsubstituted or it is substituted with one or two oxo groups;

when G is oxygen, it is unsubstituted.

16. The method according to claim 11, wherein:

$R^1$ is hydrogen;

$R^2$ is selected from the group consisting of hydrogen, $C_1$–$C_3$ alkyl, hydroxy $C_1$–$C_2$ alkyl, $C_1$–$C_2$ alkoxyphenyl, $C_1$–$C_2$ alkoxy $C_1$–$C_2$ alkyl, amino $C_1$–$C_2$ alkyl, and phenyl $C_1$–$C_2$ alkyl;

$R^3$ and $R^4$ are each independently selected from the group consisting of hydrogen, and dicyano $C_1$–$C_2$ alkyl;

$R^5$ is selected from the group consisting of hydrogen, and hydroxy;

$R^6$ is selected from the group consisting of hydrogen, hydroxy, $C_1$–$C_2$ alkoxy, amino, carboxy, diamino $C_1$–$C_2$ alkoxy, halo, 2-propenoxy, iso $C_3$–$C_4$ alkylcarboxy $C_1$–$C_2$ alkoxy, and di $C_1$–$C_2$ alkylamino;

$R^7$ is selected from the group consisting of hydrogen, hydroxy, $C_1$–$C_2$ alkoxy, hydroxy $C_1$–$C_2$ alkoxy, $C_1$–$C_2$ alkoxy $C_1$–$C_2$ alkoxy, amino $C_1$–$C_2$ alkoxy, morpholino $C_1$–$C_2$ alkoxy, carboxyl $C_1$–$C_2$ alkoxy, pyrrolidyl $C_1$–$C_2$ alkoxy, di $C_1$–$C_2$ alkylamino $C_1$–$C_2$ alkoxy, pyrrolidyl $C_1$–$C_2$ alkyl, iso $C_3$–$C_4$ alkylcarboxy $C_1$–$C_2$ alkoxy, and 2-propenoxy;

where the $R^6$ and $R^7$ groups can join to form a six membered heterocyclic ring;

$R^8$ is selected from the group consisting of hydrogen, hydroxy, halo, $C_1$–$C_2$ alkoxy, nitro, amino, and pyrrolidyl $C_1$–$C_2$ alkoxy; and G is selected from the group consisting of oxygen and sulfur;

when G is sulfur, it is unsubstituted or it is substituted with one or two oxo groups;

when G is oxygen, it is unsubstituted there.

17. The method according to claim 11, wherein:

$R^1$ is hydrogen;

$R^2$ is selected from the group consisting of hydrogen, $C_1$–$C_3$ alkyl, hydroxy $C_1$–$C_2$ alkyl, $C_1$–$C_2$ alkoxyphenyl, $C_1$–$C_2$ alkoxy $C_1$–$C_2$ alkyl, and amino $C_1$–$C_2$ alkyl;

$R^3$ and $R^4$ are each independently selected from the group consisting of hydrogen, and dicyanoethyl;

$R^5$ is selected from the group consisting of hydrogen, and hydroxy;

$R^6$ is selected from the group consisting of hydrogen, hydroxy, $C_1$–$C_2$ alkoxy, amino, carboxy, diamino $C_1$–$C_2$ alkoxy, halo, 2-propenoxy, iso $C_3$–$C_4$ alkylcarboxy $C_1$–$C_2$ alkoxy, and di $C_1$–$C_2$ alkylamino;

$R^7$ is selected from the group consisting of hydrogen, hydroxy, $C_1$–$C_2$ alkoxy, hydroxy $C_1$–$C_2$ alkoxy, $C_1$–$C_2$ alkoxy $C_1$–$C_2$ alkoxy, amino $C_1$–$C_2$ alkoxy, morpholino $C_1$–$C_2$ alkoxy, carboxyl $C_1$–$C_2$ alkoxy, pyrrolidyl $C_1$–$C_2$ alkoxy, di $C_1$–$C_2$ alkylamino $C_1$–$C_2$ alkoxy, pyrrolidyl $C_1$–$C_2$ alkyl, iso $C_3$–$C_4$ alkylcarboxy $C_1$–$C_2$ alkoxy, and 2-propenoxy;

where the $R^6$ and $R^7$ groups can join to form a six membered heterocyclic ring;

$R^8$ is selected from the group consisting of hydrogen, hydroxy, halo, methoxy, nitro, and amino; and G is selected from the group consisting of oxygen and sulfur;

when G is sulfur, it is unsubstituted or it is substituted with one or two oxo groups;

when G is oxygen, it is unsubstituted.

\* \* \* \* \*